(12) United States Patent
Yoshimura et al.

(10) Patent No.: US 10,100,095 B2
(45) Date of Patent: Oct. 16, 2018

(54) RESISTANT MUTANT 90 KDA HEAT SHOCK PROTEIN

(71) Applicant: TAIHO PHARMACEUTICAL CO., LTD., Tokyo (JP)

(72) Inventors: Chihoko Yoshimura, Ibaraki (JP); Yasuo Kodama, Ibaraki (JP); Shuichi Ohkubo, Ibaraki (JP)

(73) Assignee: Taiho Pharmaceutical Co., Ltd., Tokyo (JP)

(*) Notice: Subject to any disclaimer, the term of this patent is extended or adjusted under 35 U.S.C. 154(b) by 6 days.

(21) Appl. No.: 15/026,413

(22) PCT Filed: Oct. 2, 2014

(86) PCT No.: PCT/JP2014/076473
§ 371 (c)(1),
(2) Date: Jun. 24, 2016

(87) PCT Pub. No.: WO2015/050235
PCT Pub. Date: Apr. 9, 2015

(65) Prior Publication Data
US 2016/0311871 A1    Oct. 27, 2016

(30) Foreign Application Priority Data
Oct. 2, 2013 (JP) .................... 2013-207743

(51) Int. Cl.
| | | |
|---|---|---|
| *C07K 14/47* | (2006.01) | |
| *A61K 31/437* | (2006.01) | |
| *C12N 15/09* | (2006.01) | |
| *G01N 33/15* | (2006.01) | |
| *G01N 33/50* | (2006.01) | |
| *G01N 33/68* | (2006.01) | |
| *C07K 16/18* | (2006.01) | |
| *A61K 47/55* | (2017.01) | |
| *A61K 38/00* | (2006.01) | |

(52) U.S. Cl.
CPC ............ *C07K 14/47* (2013.01); *A61K 31/437* (2013.01); *A61K 47/55* (2017.08); *C07K 16/18* (2013.01); *C12N 15/09* (2013.01); *G01N 33/15* (2013.01); *G01N 33/50* (2013.01); *G01N 33/6872* (2013.01); *G01N 33/6896* (2013.01); *A61K 38/00* (2013.01); *G01N 2333/47* (2013.01); *G01N 2500/04* (2013.01); *G01N 2800/52* (2013.01)

(58) Field of Classification Search
None
See application file for complete search history.

(56) References Cited

U.S. PATENT DOCUMENTS

| | | |
|---|---|---|
| 2011/0280881 A1 | 11/2011 | Udono et al. |
| 2012/0108589 A1 | 5/2012 | Kitade et al. |
| 2013/0289072 A1 | 10/2013 | Kitade et al. |
| 2013/0296320 A1 | 11/2013 | Kitade et al. |

FOREIGN PATENT DOCUMENTS

| | | |
|---|---|---|
| EP | 2452940 A1 | 5/2012 |
| EP | 2559762 A1 | 2/2013 |
| WO | 2007035620 A2 | 3/2007 |
| WO | 2008024978 A2 | 2/2008 |
| WO | 2011004610 A1 | 1/2011 |
| WO | 2011/129379 A1 | 10/2011 |
| WO | 2012051207 A2 | 4/2012 |
| WO | 2012/093707 A1 | 7/2012 |
| WO | 2012093708 A1 | 7/2012 |

OTHER PUBLICATIONS

HSP90, GenBank: AFN89572, submitted Mar. 26, 2012, pp. 1-2.*
Vallee et al., "Tricyclic Series of Heat Shock Protein 90 (Hsp90) Inhibitors Part I: Discovery of Tricyclic Imidazo [4,5-c] Pyridines as Potent Inhibitors of the Hsp90 Molecular Chaperone", Journal of Medicinal Chemistry, vol. 54, No. 20, Oct. 27, 2011, pp. 7206-7219.
European Extended Search Report dated Jul. 20, 2017, cited in Application No. 14850588.6-1410/3064582, 11 pages.
Plescia et al., "Rational design of shepherdin, a novel anticancer agent", Cancer Cell, 2005, vol. 7, No. 5, pp. 457-468.
Partial Supplementary European Search Report dated May 2, 2017 for corresponding EP Patent Application No. 14850588.6, 9 pages.
Millson et al., "Features of the Streptomyces hygroscopicus HtpG reveal how partial geldanamycin resistance can arise with mutation to the ATP binding pocket of a eukaryotic Hsp90", The FASEB Journal, 2011, vol. 25, pp. 3828-3837.
Stebbins et al., "Crystal Structure of an Hsp90-Geldanamycin Complex: Targeting of a Protein Chaperone by an Antitumor Agent", Cell, 1997, vol. 89, pp. 239-250.
Prodromou et al., "Identification and Structural Characterization of the ATP/ADP-Binding Site in the Hsp90 Molecular Chaperone", Cell, 1997, vol. 90, pp. 65-75.
Zurawska et al., "Mutations that increase both Hsp90 ATPase activity in vitro andHsp90 drug resistance in vivo", Biochimica et Biophysica Acta, 2010, vol. 1803, pp. 575-583.
Millson et al., "A simple yeast-based system for analyzing the inhibitor resistance in the human cancer drug targets Hsp90α/β", Biochemical Pharmacology, 2010, vol. 79, pp. 1581-1588.

(Continued)

*Primary Examiner* — Lianko G Garyu
(74) *Attorney, Agent, or Firm* — Rothwell, Figg, Ernst & Manbeck, P.C.

(57) ABSTRACT

An object to be solved by the present invention is to identify patients resistant to known HSP90 inhibitors, and to provide a novel therapeutic agent for treating the patients who have become resistant to known HSP90 inhibitors.
As a means for solving the above problems, the present invention provides identification of the patients based on a protein, which is an HSP90 family protein having a mutation in the site corresponding to F138 of HSP90α class A consisting of the amino acid sequence of SEQ ID NO: 1, and use of a substance that inhibits the protein as an active ingredient of a therapeutic agent.

11 Claims, 4 Drawing Sheets

Specification includes a Sequence Listing.

(56) References Cited

OTHER PUBLICATIONS

Whitesell et al., "HSP90 and teh Chaperoning of Cancer", Nature Reviews Cancer, 2005, vol. 5, pp. 761-772.
Kamal et al., "Therapeutic and diagnostic implications of HSp90 activation", Trends in Molecular Medicine, 2004, vol. 10, No. 6, pp. 283-290.
Banerji, "Heat Shock Protein 90 as a Drug Target: Some like it Hot", Clinical Cancer Research, 2009, vol. 15, pp. 9-14.
Taldone et al., "Targeting Hsp90: small-molecule inhibitors and their clinical development", Current Opinion in Pharmacology, 2008, vol. 8, pp. 370-374.
Li et al., "New developments in Hsp90 inhibitors as anti-cancer therapeutics: Mechanisms, clinical perspective and more potential", Drug Resistance Updates, 2009, vol. 12, pp. 17-27.
Luo et al., "Heat shock protein 90: translation from cancer to Alzheimer's disease treatment?", BMC Neuroscience, 2008, vol. 9, Supplement 2, S7.
Gupta et al., "Phylogenetic Analysis of the 90 kD Heat Shock Family of Protein Sequences and an Examination of the Relationship among Animals, Plants, and Fungi Species", Molecular Biology and Evolution, 1995, vol. 12, No. 6, pp. 1063-1073.
Japanese Office Action issued in JP 2015-540563 dated Aug. 16, 2018, including English language translation, 14 pages.

\* cited by examiner

RESISTANT MUTANT 90 KDA HEAT SHOCK PROTEIN

CROSS REFERENCE TO RELATED APPLICATION

This application is a 35 U.S.C. 371 National Phase Entry Application from PCT/JP2014/076473, filed Oct. 2, 2014, which claims the benefit of Japanese Patent Application No. 2013-207743 filed on Oct. 2, 2013, the disclosures of which are incorporated by reference in their entirety.

TECHNICAL FIELD

The present invention relates to a resistant mutant of 90-kDa heat-shock protein, an inhibitory substance thereof, and the like.

Background Art

A group of proteins called molecular chaperones are multifunctional. For example, they promote the formation of the functional structure of other proteins, maintain these structures, promote correct association, inhibit unnecessary aggregation, protect other proteins from degradation, and promote secretion (Non-patent Literature (NPL) 1). The 90-kDa heat-shock protein (heat-shock protein 90; HSP90) family consists of abundant molecular chaperones that account for about 1 to 2% of the total intracellular soluble proteins. Unlike other chaperon proteins, however, these abundant molecular chaperones are unnecessary for the biosynthesis of the majority of polypeptides (NPL 1). Known client proteins whose structure formation or stability are regulated by HSP90 through interaction with HSP90 mainly include signaling-related factors (e.g., ERBB1/EGFR, ERBB2/HER2, MET, IGF1R, KDR/VEGFR, FLT3, ZAP70, KIT, CHUK/IKK, BRAF, RAFI, SRC, and AKT), cell-cycle regulators (e.g., CDK4, CDK6, Cyclin D, PLK1, and BIRC5), and transcriptional regulators (e.g., HIF-1α, p53, androgen receptor, estrogen receptor, and progesterone receptor) (Non-patent Literature (NPL) 2 and Non-patent Literature (NPL) 3). By maintaining the normal functions of these proteins, HSP90 is deeply involved in cell proliferation or survival. For example, HSP90 is required for the functions of mutated or chimeric factors (e.g., BCR-ABL and NPM-ALK) that cause tumor formation or tumor exacerbation. This indicates the importance of HSP90, particularly in the processes of tumor formation, survival, growth, exacerbation, and metastasis (NPL 2). Further, HSP90 is known to be involved in diseases, such as neurodegenerative diseases, autoimmune diseases, and viral infections (NPL 6).

Human HSP90 has isoforms, i.e., HSP90α and HSP90β. HSP90α is further divided into class A and class B. Of these, HSP90α class A and class B show protein homology as high as 86%, and HSP90β also shows a high homology. Further, HSP90 is retained in the organisms of various species including yeasts and mammals, in addition to humans. Not only humans, but also vertebrates such as fish and birds, have HSP90α and HSP90β isoforms.

HSP90α class A is also referred to as HSP90AA1, and GenBank accession number: NP_005339.3 is registered as an example of the amino acid sequence thereof. HSP90α class B is also referred to as HSP90AB1, and GenBank accession number: NP_031381.2 is registered as an example of the amino acid sequence thereof. HSP90β is also referred to as HSP90B1, and GenBank accession number: NP_003290.1 is registered as an example of the amino acid sequence thereof. All of these are human HSP90s.

The inhibition of HSP90 chaperone functions with geldanamycin, i.e., an inhibitor specific to HSP90, causes the inactivation, destabilization, and degradation of the client proteins, and thus induces apoptosis or a halt in cell proliferation (NPL 4). In view of the physiological functions of HSP90, HSP90 inhibitors in the treatment of tumors are characterized in that they simultaneously inhibit a plurality of signaling pathways involved in tumor survival/growth. Thus, the HSP90 inhibitors can serve as drugs having extensive and effective antitumor activity. From the findings that tumor cell-derived HSP90 has higher activity and higher affinity for ATP or inhibitors than those of normal cell-derived HSP90, it has been expected that the HSP90 inhibitors would serve as drugs having high tumor selectivity (NPL 5). Examples of antitumor agents in which geldanamycin is adapted for use in human tumor treatment include 17-allylamino-17-desmethoxygeldanamycin (17-AAG), which is a derivative of geldanamycin, and the like. Further, at the present time, examples of HSP90 inhibitors that have a backbone different from that of geldanamycin include ganetespib, radicicol, novobiocin, and the like.

As described above, HSP90 inhibitors, such as geldanamycin and 17-AAG, are useful in the treatment of tumors, neurodegenerative diseases, autoimmune diseases, and viral infections, and are particularly useful as antitumor agents. At present, however, the resistance thereof is problematic, and the findings are still insufficient. Specifically, when HSP90 is mutated in a tumor, the antitumor effect of HSP90 inhibitors, such as geldanamycin, is reduced, possibly preventing the treatment or possibly worsening the prognosis of tumor patients. For example, when I123 of HSP90α class B, or I128 of HSP90α class A, which corresponds to I123 of HSP90α class B, is mutated, HSP90 thereof is known to become resistant to 17-AAG (Biochimica et Biophysica Acta 1803:575, 2010). However, the mechanism of the resistance of HPS90 against HSP90 inhibitors is not sufficiently known. To use HSP90 inhibitors as antitumor agents, the accumulation of further findings is required.

CITATION LIST

Patent Literature

PTL 1: WO 2007/035620
PTL 2: WO 2008/024978

Non-Patent Literature

NPL 1: Nature Reviews Cancer, 5, 761-772 (2005)
NPL 2: Trends in Molecular Medicine, Vol. 10, No. 6, 283-290 (2004)
NPL 3: Clin Can Res, 15, 9-14 (2009)
NPL 4: Current Opinion in Pharmacology, 8, 370-374 (2008)
NPL 5: Drug Resistance Updates, 12, 17-27 (2009)
NPL 6: BMC Neuroscience, 9 (Suppl 2), 2008

SUMMARY OF INVENTION

Technical Problem

An object to be solved by the present invention is to identify patients resistant to known HSP90 inhibitors, and to provide a novel therapeutic agent for treating the patients who have become resistant to known HSP90 inhibitors.

Solution to Problem

The present inventors conducted further research on a pathosis resistant to known HSP90 inhibitors, and conducted various studies regarding methods for treating the pathosis. As a result, the present inventors found that a specific residue of HSP90 family protein plays a critical role in the acquisition of the resistance to known HSP90 inhibitors. Based on this finding, the present inventors found that it is possible to identify patients resistant to known HSP90 inhibitors. The present inventors further found that it is possible to provide a novel therapeutic agent having therapeutic effects on patients who have become resistant to known HSP90 inhibitors. The present inventors made further improvements, and completed the present invention.

Specifically, the present invention encompasses, for example, the inventions of the following Items.

Item 1.

An HSP90 family protein having a mutation in the site corresponding to F138 of HSP90α class A consisting of the amino acid sequence of SEQ ID NO: 1; or a part of the protein having the mutation.

Item 2.

The protein or a part thereof according to Item 1, wherein the mutation is substitution, deletion, addition, or insertion of amino acid at the site corresponding to F138.

Item 3.

The protein or a part thereof according to Item 1 or 2, wherein the amino acid present in the site corresponding to F138 is substituted with an amino acid other than phenylalanine.

Item 4.

The protein or a part thereof according to any one of Items 1 to 3, wherein the HSP90 family protein is animal HSP90.

Item 5.

The protein or a part thereof according to Item 4, wherein the HSP90 family protein is human HSP90.

Item 6.

The protein or a part thereof according to Item 4 or 5, wherein the HSP90 family protein is HSP90α class A, HSP90α class B, or HSP90.

Item 7.

The protein or a part thereof according to Item 6, wherein the HSP90 family protein is (I) HSP90α class A consisting of the amino acid sequence of SEQ ID NO: 1, or an isoform, splicing variant, mutant, or derivative of the HSP90α class A;

(II) HSP90α class B consisting of the amino acid sequence of SEQ ID NO: 2, or an isoform, splicing variant, mutant, or derivative of the HSP90α class B; or (III) HSP90β consisting of the amino acid sequence of SEQ ID NO: 3, or an isoform, splicing variant, mutant, or derivative of the HSP90β.

Item 8a.

A protein consisting of the amino acid sequence of one protein selected from the protein according to any one of Items 1 to 7, wherein one or more amino acids are substituted, deleted, added, or inserted, in addition to the mutation in the site corresponding to F138.

Item 8b.

The protein according to Item 8a, wherein the protein consists of an amino acid sequence in which at least a tag peptide is added to the amino acid sequence of one protein selected from the protein according to any one of Items 1 to 7.

Item 8c.

The protein according to Item 8a or 8b, wherein the protein has inferior binding ability with respect to at least one kind of known HSP90 inhibitor, compared with a protein consisting of an amino acid sequence of the selected one protein that does not have the mutation in the site corresponding to F138.

Item 9.

A part of the protein according to any one of Items 8a to 8c, wherein the part of the protein has the mutation in the site corresponding to F138.

Item 10.

The protein or a part thereof according to Item 6, which is:

(i-1) an HSP90α class A protein having a mutation in the amino acid corresponding to F138 of HSP90α class A consisting of the amino acid sequence of SEQ ID NO: 1 in HSP90α class A;

(i-2) the HSP90α class A protein according to (i-1) which has a mutation at F138 in HSP90α class A consisting of the amino acid sequence of SEQ ID NO: 1;

(i-3) the HSP90α class A protein according to (i-1) or (i-2), wherein the mutation is substitution, deletion, addition, or insertion of amino acid;

(i-4) a protein consisting of an amino acid sequence of the HSP90α class A protein according to any one of (i-1) to (i-3), wherein one or more amino acids are substituted, deleted, added, or inserted at a site or sites other than the amino acid mutation in the site corresponding to F138;

(i-5) the protein according to (i-4), wherein the protein has inferior binding ability with respect to at least one kind of known HSP90 inhibitor, compared with HSP90α class A consisting of the amino acid sequence of SEQ ID NO: 1;

(ii-1) an HSP90α class B protein having a mutation in the amino acid corresponding to F133 of HSP90α class B consisting of the amino acid sequence of SEQ ID NO: 2 in HSP90α class B;

(ii-2) the HSP90α class B protein according to (ii-1) which has a mutation at F133 in HSP90α class B consisting of the amino acid sequence of SEQ ID NO: 2;

(ii-3) the HSP90α class B protein according to (ii-1) or (ii-2), wherein the mutation is substitution, deletion, addition, or insertion of amino acid;

(ii-4) a protein consisting of an amino acid sequence of the HSP90α class B protein according to any one of (ii-1) to (ii-3), wherein one or more amino acids are substituted, deleted, added, or inserted at a site or sites other than the amino acid mutation in the site corresponding to F133;

(ii-5) the protein according to (ii-4), wherein the protein has inferior binding ability with respect to at least one kind of known HSP90 inhibitor, compared with HSP90α class B consisting of the amino acid sequence of SEQ ID NO: 2;

(iii-1) an HSP90β protein having a mutation in the amino acid corresponding to F199 of HSP90 consisting of the amino acid sequence of SEQ ID NO: 3 in HSP90;

(iii-2) the HSP90β protein according to (iii-1) which is has a mutation at F199 in HSP90β consisting of the amino acid sequence of SEQ ID NO: 3;

(iii-3) the HSP90β protein according to (iii-1) or (iii-2), wherein the mutation is substitution, deletion, addition, or insertion of amino acid;

(iii-4) a protein consisting of the amino acid sequence of the HSP90β protein according to any one of (iii-1) to (iii-3), wherein one or more amino acids are substituted, deleted, added, or inserted at a site or sites other than the amino acid mutation in the site corresponding to F199;

(iii-5) the protein according to (iii-4), wherein the protein has inferior binding ability with respect to at least one kind of known HSP90 inhibitor, compared with HSP90β consisting of the amino acid sequence of SEQ ID NO: 3;

(iv-1) a protein having a mutation in the 137th amino acid in the amino acid sequence of SEQ ID NO: 4;

(iv-2) the protein according to (iv-1), wherein the mutation is substitution, deletion, addition, or insertion of amino acid;

(iv-3) a protein consisting of an amino acid sequence of the protein according to (iv-1) or (iv-2), wherein one or more amino acids are substituted, deleted, added, or inserted, in addition to the amino acid mutation in the 137th site of the amino acid sequence of SEQ ID NO: 4; or (iv-4) the protein according to (iv-3), wherein the protein has inferior binding ability with respect to at least one kind of known HSP90 inhibitor, compared with a protein consisting of the amino acid sequence of SEQ ID NO: 4.

Item 11.

The protein or a part thereof according to Item 6 which is:

(i) an HSP90α class A protein consisting of the amino acid sequence of SEQ ID NO: 9;

(ii) an HSP90α class B protein consisting of the amino acid sequence of SEQ ID NO: 10;

(iii) an HSP90β protein consisting of the amino acid sequence of SEQ ID NO: 11; or (iv) a protein consisting of the amino acid sequence of SEQ ID NO: 12.

Item 12.

A nucleic acid encoding the protein or a part thereof according to any one of Items 1 to 11.

Item 13a.

cDNA encoding the protein or a part thereof according to any one of Items 1 to 11.

Item 13b.

The nucleic acid according to Item 12, wherein the nucleic acid is:

(i-a) a polynucleotide, which is DNA consisting of a base sequence in which the 412th to 414th base sequence of SEQ ID NO: 5 is mutated to a sequence encoding an amino acid other than phenylalanine; or RNA consisting of a base sequence in which T in the base sequence of the DNA is substituted with U;

(i-b) a polynucleotide encoding an HSP90α class A gene-splicing variant having a part or a plurality of parts of the polynucleotide according to (i-a);

(i-c) a polynucleotide that hybridizes with a polynucleotide consisting of a base sequence complementary to the base sequence of the polynucleotide according to (i-a) or (i-b) under a stringent condition, and encodes a protein having inferior binding ability with respect to at least one kind of known HSP90 inhibitor, compared with HSP90α class A;

(i-d) a polynucleotide comprising a base sequence having identity of not less than 80% with the base sequence of the polynucleotide according to (i-a) or (i-b), and encodes a protein having inferior binding ability with respect to at least one kind of known HSP90 inhibitor, compared with HSP90α class A;

(ii-a) a polynucleotide, which is DNA consisting of a base sequence in which the 397th to 399th base sequence of SEQ ID NO: 6 is mutated to a sequence encoding an amino acid other than phenylalanine; or RNA consisting of a base sequence in which T in the base sequence of the DNA is substituted with U;

(ii-b) a polynucleotide encoding an HSP90α class B gene-splicing variant having a part or a plurality of parts of the polynucleotide according to (ii-a);

(ii-c) a polynucleotide that hybridizes with a polynucleotide consisting of a base sequence complementary to a base sequence of the polynucleotide according to (ii-a) or (ii-b) under a stringent condition, and encodes a protein having inferior binding ability with respect to at least one kind of known HSP90 inhibitor, compared with HSP90α class B;

(ii-d) a polynucleotide comprising a base sequence having identity of not less than 80% with the base sequence of the polynucleotide according to (ii-a) or (ii-b), and encodes a protein having inferior binding ability with respect to at least one kind of known HSP90 inhibitor, compared with HSP90α class B;

(iii-a) a polynucleotide, which is DNA consisting of a base sequence in which the 598th to 600th base sequence of SEQ ID NO: 7 is mutated to a sequence encoding an amino acid other than phenylalanine; or RNA consisting of a base sequence in which T in the base sequence of the DNA is substituted with U;

(iii-b) a polynucleotide encoding an HSP90β gene-splicing variant having a part or a plurality of parts of the polynucleotide according to (iii-a);

(iii-c) a polynucleotide that hybridizes with a polynucleotide consisting of a base sequence complementary to a base sequence of the polynucleotide according to (iii-a) or (iii-b) under a stringent condition, and encodes a protein having inferior binding ability with respect to at least one kind of known HSP90 inhibitor, compared with HSP90β;

(iii-d) a polynucleotide comprising a base sequence having identity of not less than 80% with the base sequence of the polynucleotide according to (iii-a) or (iii-b), and encodes a protein having inferior binding ability with respect to at least one kind of known HSP90 inhibitor, compared with HSP90β;

(iv-a) a polynucleotide, which is DNA consisting of a base sequence in which the 409th to 411th base sequence of SEQ ID NO: 8 is mutated to a sequence encoding an amino acid other than phenylalanine; or RNA consisting of a base sequence in which T in the base sequence of the DNA is substituted with U;

(iv-b) a polynucleotide that hybridizes with a polynucleotide consisting of a base sequence complementary to a base sequence of the polynucleotide according to (i-a) under a stringent condition, and encodes a protein having inferior binding ability with respect to at least one kind of known HSP90 inhibitor, compared with the protein consisting of the amino acid sequence of SEQ ID NO: 4; or (iv-c) a polynucleotide comprising a base sequence having identity of not less than 80% with the base sequence of the polynucleotide according to (i-a), and encodes a protein having inferior binding ability with respect to at least one kind of known HSP90 inhibitor, compared with the protein consisting of the amino acid sequence of SEQ ID NO: 4.

Item 13c.

The nucleic acid according to Item 12, wherein the nucleic acid is:

a polynucleotide encoding a polypeptide consisting of the amino acid sequence of SEQ ID NO: 9;

a polynucleotide encoding a polypeptide consisting of the amino acid sequence of SEQ ID NO: 10;

a polynucleotide encoding a polypeptide consisting of the amino acid sequence of SEQ ID NO: 11; or a polynucleotide encoding a polypeptide consisting of the amino acid sequence of SEQ ID NO: 12.

Item 14.
A probe or primer for recognizing a nucleic acid consisting of a base sequence that encodes an HSP90 family protein and has a mutation in the site corresponding to F138 of HSP90α class A consisting of the amino acid sequence of SEQ ID NO: 1.
Item 15.
A probe or primer for recognizing the nucleic acid or the cDNA according to any one of Items 12, and 13a to 13c.
Item 16.
A vector comprising the nucleic acid according to any one of Items 12, and 13a to 13c.
Item 17.
A cell comprising the vector according to Item 16.
Item 18.
An antibody for recognizing the protein or a part thereof according to any one of Items 1 to 11.
Item 19.
The antibody according to Item 18, wherein the antibody is:
(α-1) an antibody that specifically recognizes an HSP90α class A protein having a mutation in the amino acid corresponding to F138 of HSP90α class A consisting of the amino acid sequence of SEQ ID NO: 1 in HSP90α class A;
(β-1) an antibody that specifically recognizes an HSP90α class B protein having a mutation in the amino acid corresponding to F133 of HSP90α class B consisting of the amino acid sequence of SEQ ID NO: 2 in HSP90α class B;
(γ-1) an antibody that specifically recognizes an HSP90β protein having a mutation in the amino acid corresponding to F199 of HSP90β consisting of the amino acid sequence of SEQ ID NO: 3 in HSP90β; or
(δ-1) an antibody that specifically recognizes a protein consisting of the amino acid sequence of SEQ ID NO: 12.
Item 20.
The antibody according to Item 19, wherein the antibody is:
(α-2) the antibody according to (α-1), wherein the antibody has the mutation site in an epitope;
(β-2) the antibody according to (β-1), wherein the antibody has the mutation site in an epitope;
(γ-2) the antibody according to (γ-1), wherein the antibody has the mutation site in an epitope; or
(δ-2) the antibody according to (δ-1), wherein the antibody has Xaa site in SEQ ID NO: 12.
Item 21.
A method for screening an HSP90 family protein inhibitory substance, comprising:
applying a test substance with respect to the HSP90 family protein or a part thereof according to any one of Items 1 to 11; and
measuring the activity of the HSP90 family protein or the binding activity between the HSP90 family protein and the test substance.
Item 22.
The screening method according to Item 21, wherein in the HSP90 family protein or a part thereof, the HSP90 family protein inhibitory substance fills a cavity in the vicinity of at least one amino acid selected from the group consisting of 5 amino acids in sites corresponding to F170, F22, G108, Y139, or W162 of HSP90α class A consisting of the amino acid sequence of SEQ ID NO: 1.
Item 23.
The screening method according to Item 21 or 22, wherein, in the HSP90 family protein or a part thereof, the HSP90 family protein inhibitory substance interacts with at least one amino acid selected from the group consisting of 5 amino acids in sites corresponding to F170, F22, G108, Y139, or W162 of HSP90α class A consisting of the amino acid sequence of SEQ ID NO: 1.
Item 24.
A method for testing a biological sample, comprising: detecting the presence/absence of a mutation in the site corresponding to F138 of HSP90α class A consisting of the amino acid sequence of SEQ ID NO: 1 in an HSP90 family protein in a biological sample obtained from a test subject; and using the detection of the mutation as an index in determining a resistance to an HSP90 inhibitor.
Item 25.
The method according to Item 24, wherein the HSP90 inhibitor is geldanamycin, 17-AAG, 17-DMAG, ganetespib (STA-9090), radicicol, BIIB021, SNX-2112, SNX-5422, AT13387, IPI-504, IPI-493, KW-2478, DS-2248, XL888, CUDC-305 (Debio0932), PU-H71, NVP-AUY922, HSP990, or MPC-3100.
Item 26.
The method according to Item 24 or 25, wherein the mutation in the site corresponding to F138 is:
a mutation of the amino acid corresponding to F138 of HSP90α class A consisting of the amino acid sequence of SEQ ID NO: 1, in human HSP90α class A;
a mutation of the amino acid corresponding to F133 of HSP90α class B consisting of the amino acid sequence of SEQ ID NO: 2, in human HSP90α class B; or
a mutation of the amino acid corresponding to F199 of HSP90β consisting of the amino acid sequence of SEQ ID NO: 3, in human HSP90β.
Item 27.
A method for testing a test subject, comprising: detecting the presence/absence of a mutation in the site corresponding to F138 of HSP90α class A consisting of the amino acid sequence of SEQ ID NO: 1 in an HSP90 family protein in a biological sample obtained from a test subject; and using the detection of the mutation as an index in determining a resistance to an HSP90 inhibitor.
Item 28.
The method according to Item 27, wherein the HSP90 inhibitor is geldanamycin, 17-AAG, 17-DMAG, ganetespib (STA-9090), radicicol, BIIB021, SNX-2112, SNX-5422, AT13387, IPI-504, IPI-493, KW-2478, DS-2248, XL888, CUDC-305 (Debio0932), PU-H71, NVP-AUY922, HSP990, or MPC-3100.
Item 29.
The method according to Item 27 or 28, wherein the mutation in the site corresponding to F138 is:
a mutation of the amino acid corresponding to F138 of HSP90α class A consisting of the amino acid sequence of SEQ ID NO: 1, in human HSP90α class A;
a mutation of the amino acid corresponding to F133 of HSP90α class B consisting of the amino acid sequence of SEQ ID NO: 2, in human HSP90α class B; or
a mutation of the amino acid corresponding to F199 of HSP90β consisting of the amino acid sequence of SEQ ID NO: 3, in human HSP90β.
Item 30.
The method according to any one of Items 24 to 29, wherein the test subject is a tumor patient.
Item 31.
A therapeutic agent for neurodegenerative disorder, tumor, autoimmune disease, or viral infection for treating a patient in which, in HSP90 family protein, a protein having a mutation in the site corresponding to F138 of HSP90α class A consisting of the amino acid sequence of SEQ ID NO: 1 is expressed.

Item 32.

The therapeutic agent for neurodegenerative disorder, tumor, autoimmune disease, or viral infection according to Item 31, wherein the therapeutic agent comprises an HSP90 family inhibitory substance that, in an HSP90 family protein, fills a cavity in the vicinity of at least one amino acid selected from the group consisting of 5 amino acids in sites corresponding to F170, F22, G108, Y139, or W162 of HSP90α class A consisting of the amino acid sequence of SEQ ID NO: 1.

Item 33.

The therapeutic agent for neurodegenerative disorder, tumor, autoimmune disease, or viral infection according to Item 31 or 32, wherein the therapeutic agent comprises an HSP90 family inhibitory substance that interacts with, in an HSP90 family protein, at least one amino acid selected from the group consisting of 5 amino acids in sites corresponding to F170, F22, G108, Y139, or W162 of HSP90α class A consisting of the amino acid sequence of SEQ ID NO: 1.

Item 34.

The therapeutic agent for neurodegenerative disorder, tumor, autoimmune disease, or viral infection according to any one of Items 31 to 33, wherein the therapeutic agent comprises a compound represented by Formula (a), (b), or (c) below, or a salt thereof;

Formula (a):

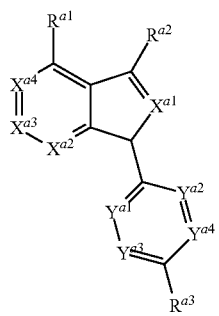

(a)

wherein $X^{a1}$ represents CH or N;
one of $X^{a2}$, $X^{a3}$, and $X^{a4}$ represents N, and the others each represent CH;
one or two of $Y^{a1}$, $Y^{a2}$, $Y^{a3}$, and $Y^{a4}$ represent C—$R^{a4}$, and the others are identical or different and each represents CH or N;
$R^{a1}$ represents an optionally substituted monocyclic or bicyclic unsaturated heterocyclic group having 1 to 4 heteroatoms selected from N, S, and O;
$R^{a2}$ represents hydrogen, optionally substituted $C_{1-6}$ alkyl, or optionally substituted $C_{2-6}$ alkenyl;
$R^{a3}$ represents cyano or —CO—$R^{a5}$;
$R^{a4}$s are identical or different and each represents hydrogen, halogen, cyano, optionally substituted $C_{1-6}$ alkyl, $C_{2-6}$ alkenyl, $C_{1-6}$ alkoxy, aromatic hydrocarbon, —N($R^{a6}$)($R^{a7}$), —S—$R^{a8}$, or —CO—$R^{a9}$;
$R^{a5}$ represents amino optionally having hydroxyl, or optionally substituted mono- or dialkylamino;
$R^{a6}$ and $R^{a7}$ are identical or different and each represents hydrogen, optionally substituted $C_{1-6}$ alkyl, $C_{1-6}$ halogenoalkyl, optionally substituted $C_{3-7}$ cycloalkyl, optionally substituted aralkyl, optionally substituted aromatic hydrocarbon, an optionally substituted saturated heterocyclic group, or an optionally substituted unsaturated heterocyclic group, or
$R^{a6}$ and $R^{a7}$, taken together with the nitrogen to which they are attached, may form a saturated heterocyclic group;
$R^{a8}$ represents optionally substituted $C_{3-7}$ cycloalkyl or optionally substituted aromatic hydrocarbon; and
$R^{a9}$ represents hydrogen, hydroxyl, amino optionally having hydroxyl, or optionally substituted mono- or dialkylamino, Formula (b):

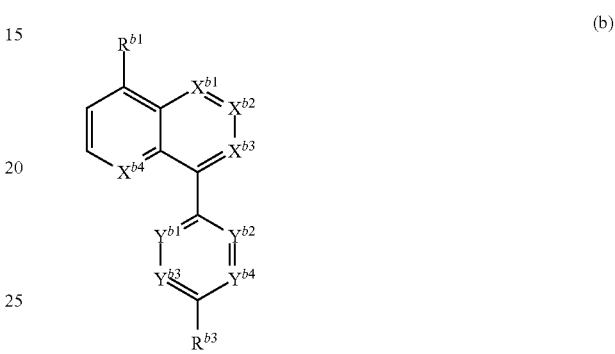

(b)

wherein at least one of $X^{b1}$, $X^{b2}$, $X^{b3}$, and $X^{b4}$ represents N or N-oxide, and the others are identical or different and each represents C—$R^{b2}$;
one or two of $Y^{b1}$, $Y^{b2}$, $Y^{b3}$, and $Y^{b4}$ represents C—$R^{b4}$, and the others are identical or different and each represents CH or N;
$R^{b1}$ represents an optionally substituted monocyclic or bicyclic unsaturated heterocyclic group having 1 to 4 heteroatoms selected from N, S, and O;
$R^{b2}$ represents hydrogen, optionally substituted $C_{1-6}$ alkyl, optionally substituted $C_{3-7}$ cycloalkyl, or optionally substituted $C_{2-6}$ alkenyl;
$R^{b3}$ represents hydrogen, halogen, cyano, $C_{1-6}$ alkyl, $C_{1-6}$ alkoxy, or —CO—$R^{b5}$;
$R^{b4}$ represents hydrogen, halogen, $C_{1-6}$ alkyl, $C_{1-6}$ alkoxy, —CO—$R^{b6}$, —N($R^{b7}$)($R^{b8}$), or —S—$R^{b9}$;
$R^{b5}$ represents hydroxyl, amino, or optionally substituted $C_{1-6}$ alkylamino;
$R^{b6}$ represents hydroxyl, amino optionally having hydroxyl, or optionally substituted $C_{1-6}$ alkylamino;
$R^{b7}$ and $R^{b8}$ are identical or different and each represents hydrogen, optionally substituted $C_{1-6}$ alkyl, optionally substituted $C_{3-7}$ cycloalkyl, optionally substituted aromatic hydrocarbon, an optionally substituted saturated heterocyclic group, or an optionally substituted unsaturated heterocyclic group, or
$R^{b7}$ and $R^{b8}$, taken together with the nitrogen to which they are attached, may form a saturated heterocyclic group; and
$R^{b9}$ represents optionally substituted $C_{3-7}$ cycloalkyl or optionally substituted aromatic hydrocarbon, or Formula (c):

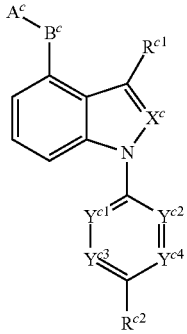

wherein $X^c$ represents CH or N;

one or two of $Y^{c1}$, $Y^{c2}$, $Y^{c3}$, and $Y^{c4}$ represent C—$R^{c3}$ or N, and the others each represent CH;

$A^c$ and $B^c$ are identical or different and each represents an optionally substituted monocyclic unsaturated heterocyclic group having 1 to 4 heteroatoms selected from N, S, and O;

$R^{c1}$ represents hydrogen, optionally substituted $C_{1-6}$ alkyl, optionally substituted $C_{3-7}$ cycloalkyl, or optionally substituted $C_{2-6}$ alkenyl;

$R^{c2}$ represents hydrogen, halogen, cyano, or —CO—$R^{c4}$;

$R^{c3}$ represents hydrogen, halogen, $C_{1-6}$ alkyl, $C_{1-6}$ alkoxy, —CO—$R^{c5}$, —N($R^{c6}$)($R^{c7}$), or —S—$R^{c8}$;

$R^{c4}$ and $R^{c5}$ are identical or different and each represents hydroxyl, amino, or $C_{1-6}$ alkylamino;

$R^{c6}$ and $R^{c7}$ are identical or different and each represents hydrogen, $C_{1-6}$ alkyl, $C_{3-7}$ cycloalkyl optionally having hydroxyl, aromatic hydrocarbon, a saturated heterocyclic group, or an unsaturated heterocyclic group, or $R^{c6}$ and $R^{c7}$, taken together with the nitrogen to which they are attached, may form a saturated heterocyclic group; and $R^{c8}$ represents optionally substituted $C_{3-7}$ cycloalkyl or optionally substituted aromatic hydrocarbon.

Item 35.

The therapeutic agent for neurodegenerative disorder, tumor, autoimmune disease, or viral infection according to Item 34, wherein the therapeutic agent comprises a compound represented by Formula (a) or a salt thereof.

Item 36.

The therapeutic agent for neurodegenerative disorder, tumor, autoimmune disease, or viral infection according to Item 35, wherein the therapeutic agent comprises a compound represented by Formula (d) below or a salt thereof.

Formula (d):

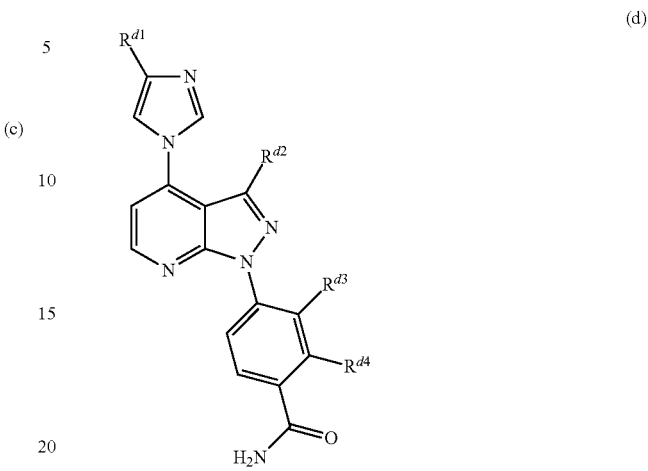

wherein $R^{d1}$ represents 1H-pyrazol-4-yl, 1-methyl-1H-pyrazol-4-yl, 1-ethyl-1H-pyrazol-4-yl, 1-isopropyl-1H-pyrazol-4-yl, pyridin-3-yl, pyridin-4-yl, or pyrimidin-5-yl;

$R^{d2}$ represents methyl, ethyl, n-propyl, isopropyl, n-butyl, isobutyl, sec-butyl, tert-butyl, or trifluoromethyl; and $R^{d3}$ and $R^{d4}$ are such that $R^{d3}$ represents hydrogen, and $R^{d4}$ represents methyl, ethyl, n-propyl, amino, methylamino ($CH_3NH$—), or ethylamino ($CH_3CH_2NH$—), or that $R^{d4}$ represents hydrogen, and $R^{d3}$ represents methyl, ethyl, n-propyl, amino, methylamino ($CH_3NH$—), or ethylamino ($CH_3CH_2NH$—).

Item 37.

The therapeutic agent for neurodegenerative disorder, tumor, autoimmune disease, or viral infection according to any one of Items 31 to 36, wherein the HSP90 family protein having a mutation in the site corresponding to F138 of HSP90α class A consisting of the amino acid sequence of SEQ ID NO: 1 is the protein according to any one of Items 1 to 11.

Item 38.

Therapeutic agent according to any one of Items 31 to 37 which is for treating tumors.

Item 39.

A therapeutic method for neurodegenerative disorder, tumor, autoimmune disease or viral infection, comprising administering the therapeutic agent according to any one of Items 31 to 38 to a patient in which an HSP90 family protein having a mutation in the site corresponding to F138 of HSP90α class A consisting of the amino acid sequence of SEQ ID NO: 1 is expressed.

Item 40.

The therapeutic method for neurodegenerative disorder, tumor, autoimmune disease or viral infection according to Item 39, wherein the patient is resistant to geldanamycin, 17-AAG, 17-DMAG, ganetespib (STA-9090), radicicol, BIIB021, SNX-2112, SNX-5422, AT13387, IPI-504, IPI-493, KW-2478, DS-2248, XL888, CUDC-305 (Debio0932), PU-H71, NVP-AUY922, HSP990, or MPC-3100.

Item 41.

The therapeutic method for neurodegenerative disorder, tumor, autoimmune disease or viral infection according to Item 39 or 40, wherein the patient is a patient in which the protein according to any one of Items 1 to 11 is expressed.

Item 42.

The therapeutic method according to any one of Items 39 to 41 for treating tumors, wherein the patient is a tumor patient.

Item 43.

An HSP90 inhibition method comprising applying the compound represented by Formula (a), (b), or (c) according to Item 34, the compound represented by Formula (d) according to Item 36, or a salt thereof with respect to a protein, which is an HSP90 family protein consisting of the amino acid sequence of SEQ ID NO: 1 and has a mutation in the site corresponding to F138 of HSP90α class A.

Item 44.

A complex comprising:
(1) the protein or a part thereof according to any one of Items 1 to 11; and
(2) a compound bonded to the protein or a part thereof.

Item 45.

The complex according to Item 44, wherein, in the HSP90 family protein or a part thereof, the compound fills a cavity in the vicinity of at least one amino acid selected from the group consisting of 5 amino acids in sites corresponding to F170, F22, G108, Y139, or W162 of HSP90α class A consisting of the amino acid sequence of SEQ ID NO: 1.

Item 46.

The complex according to Item 44 or 45, wherein, in the HSP90 family protein or a part thereof, the compound interacts with at least one amino acid selected from the group consisting of 5 amino acids in sites corresponding to F170, F22, G108, Y139, or W162 of HSP90α class A consisting of the amino acid sequence of SEQ ID NO: 1.

Item 47.

The complex according to any one of Items 44 to 46, wherein the compound is geldanamycin, 17-AAG, 17-DMAG, ganetespib (STA-9090), radicicol, BIIB021, SNX-2112, SNX-5422, AT13387, IPI-504, IPI-493, KW-2478, DS-2248, XL888, CUDC-305 (Debio0932), PU-H71, NVP-AUY922, HSP990, or MPC-3100.

Item 48.

The complex according to any one of Items 44 to 47, wherein the compound is the compound represented by Formula (a), (b) or (c) according to Item 34, the compound represented by Formula (d) according to Item 36, or a salt thereof.

Item 49.

The complex according to any one of Items 44 to 48, wherein the compound is a substance capable of inhibition of binding of the protein or a part thereof to geldanamycin.

Item 50.

The complex according to any one of Items 44 to 49, wherein the protein or a part thereof has chaperone functions, and the chaperone functions are inhibited by the compound.

Item 31C.

Use of a compound or a salt thereof, which is an HSP90 family inhibitory substance, in the manufacture of a therapeutic agent for neurodegenerative disorder, tumor, autoimmune disease, or viral infection of a patient in which, in HSP90 family protein, a protein having a mutation in the site corresponding to F138 of HSP90α class A consisting of the amino acid sequence of SEQ ID NO: 1 is expressed.

Item 32C.

Use of the compound or a salt thereof according to Item 31C for the manufacture of a therapeutic agent for neurodegenerative disorder, tumor, autoimmune disease, or viral infection of a patient in which, in HSP90 family protein, a protein having a mutation in the site corresponding to F138 of HSP90α class A consisting of the amino acid sequence of SEQ ID NO: 1 is expressed, wherein the compound or a salt thereof is an HSP90 family inhibitory substance that, in HSP90 family protein, fills a cavity in the vicinity of at least one amino acid selected from the group consisting of 5 amino acids in sites corresponding to F170, F22, G108, Y139, or W162 of HSP90α class A consisting of the amino acid sequence of SEQ ID NO: 1.

Item 33C.

Use of the compound or a salt thereof according to Item 31C or 32C for the manufacture of a therapeutic agent for neurodegenerative disorder, tumor, autoimmune disease, or viral infection of a patient in which, in HSP90 family protein, a protein having a mutation in the site corresponding to F138 of HSP90α class A consisting of the amino acid sequence of SEQ ID NO: 1 is expressed, wherein the compound or a salt thereof is an HSP90 family inhibitory substance that interacts with, in HSP90 family protein, at least one amino acid selected from the group consisting of 5 amino acids in sites corresponding to F170, F22, G108, Y139, or W162 of HSP90α class A consisting of the amino acid sequence of SEQ ID NO: 1.

Item 34C.

The use of a compound represented by Formula (a), (b), or (c) below or a salt thereof according to any one Items 31C to 33C for the manufacture of a therapeutic agent for neurodegenerative disorder, tumor, autoimmune disease, or viral infection of a patient in which, in HSP90 family protein, a protein having a mutation in the site corresponding to F138 of HSP90α class A consisting of the amino acid sequence of SEQ ID NO: 1 is expressed.

Formula (a):

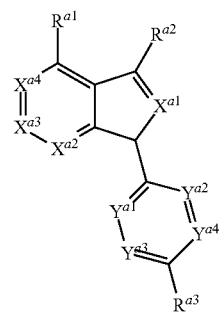

(a)

wherein $X^{a1}$ represents CH or N;
one of $X^{a2}$, $X^{a3}$, and $X^{a4}$ represents N, and the others each represent CH;
one or two of $Y^{a1}$, $Y^{a2}$, $Y^{a3}$, and $Y^{a4}$ represent C—$R^{a4}$, and the others are identical or different and each represents CH or N;
$R^{a1}$ represents an optionally substituted monocyclic or bicyclic unsaturated heterocyclic group having 1 to 4 heteroatoms selected from N, S, and O;
$R^{a2}$ represents hydrogen, optionally substituted $C_{1-6}$ alkyl, or optionally substituted $C_{2-6}$ alkenyl;
$R^{a3}$ represents cyano or —CO—$R^{a5}$;
$R^{a4}$s are identical or different and each represents hydrogen, halogen, cyano, optionally substituted $C_{1-6}$ alkyl, $C_{2-6}$ alkenyl, $C_{1-6}$ alkoxy, aromatic hydrocarbon, —N($R^{a6}$)($R^{a7}$), —S—$R^{a8}$, or —CO—$R^{a9}$; $R^{a5}$ represents amino optionally having hydroxyl, or optionally substituted mono- or dialkylamino;
$R^{a6}$ and $R^{a7}$ are identical or different and each represents hydrogen, optionally substituted $C_{1-6}$ alkyl, $C_{1-6}$ halogenoalkyl, optionally substituted $C_{3-7}$ cycloalkyl, optionally substituted aralkyl, optionally substituted aromatic hydrocarbon, an optionally substituted saturated heterocyclic group, or an optionally substituted unsaturated heterocyclic group, or $R^{a6}$ and $R^{a7}$, taken together with the nitrogen to which they are attached, may form a saturated heterocyclic group;

$R^{a8}$ represents optionally substituted $C_{3-7}$ cycloalkyl or optionally substituted aromatic hydrocarbon; and $R^{a9}$ represents hydrogen, hydroxyl, amino optionally having hydroxyl, or optionally substituted mono- or dialkylamino, Formula (b):

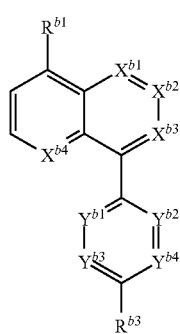

(b)

wherein at least one of $X^{b1}$, $X^{b2}$, $X^{b3}$, and $X^{b4}$ represents N or N-oxide, and the others are identical or different and each represents $C-R^{b2}$;

one or two of $Y^{b1}$, $Y^{b2}$, $Y^{b3}$, and $Y^{b4}$ represents $C-R^{b4}$, and the others are identical or different and each represents CH or N;

$R^{b1}$ represents an optionally substituted monocyclic or bicyclic unsaturated heterocyclic group having 1 to 4 heteroatoms selected from N, S, and O;

$R^{b2}$ represents hydrogen, optionally substituted $C_{1-6}$ alkyl, optionally substituted $C_{3-7}$ cycloalkyl, or optionally substituted $C_{2-6}$ alkenyl;

$R^{b3}$ represents hydrogen, halogen, cyano, $C_{1-6}$ alkyl, $C_{1-6}$ alkoxy, or $-CO-R^{b5}$;

$R^{b4}$ represents hydrogen, halogen, $C_{1-6}$ alkyl, $C_{1-6}$ alkoxy, $-CO-R^{b6}$, $-N(R^{b7})(R^{b8})$, or $-S-R^{b9}$;

$R^{b5}$ represents hydroxyl, amino, or optionally substituted $C_{1-6}$ alkylamino;

$R^{b6}$ represents hydroxyl, amino optionally having hydroxyl, or optionally substituted $C_{1-6}$ alkylamino;

$R^{b7}$ and $R^{b8}$ are identical or different and each represents hydrogen, optionally substituted $C_{1-6}$ alkyl, optionally substituted $C_{3-7}$ cycloalkyl, optionally substituted aromatic hydrocarbon, an optionally substituted saturated heterocyclic group, or an optionally substituted unsaturated heterocyclic group, or $R^{b7}$ and $R^{b8}$, taken together with the nitrogen to which they are attached, may form a saturated heterocyclic group; and $R^{b9}$ represents optionally substituted $C_{3-7}$ cycloalkyl or optionally substituted aromatic hydrocarbon, or Formula (c):

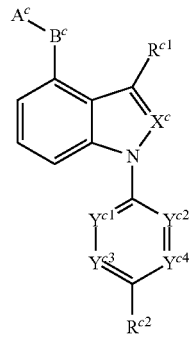

(c)

wherein $X^c$ represents CH or N;

one or two of $Y^{c1}$, $Y^{c2}$, $Y^{c3}$, and $Y^{c4}$ represent $C-R^{c3}$ or N, and the others each represent CH;

$A^c$ and $B^c$ are identical or different and each represents an optionally substituted monocyclic unsaturated heterocyclic group having 1 to 4 heteroatoms selected from N, S, and O;

$R^{c1}$ represents hydrogen, optionally substituted $C_{1-6}$ alkyl, optionally substituted $C_{3-7}$ cycloalkyl, or optionally substituted $C_{2-6}$ alkenyl;

$R^{c2}$ represents hydrogen, halogen, cyano, or $-CO-R^4$;

$R^{c3}$ represents hydrogen, halogen, $C_{1-6}$ alkyl, $C_{1-6}$ alkoxy, $-CO-R^{c5}$, $-N(R^{c6})(R^{c7})$, or $-S-R^{c8}$;

$R^{c4}$ and $R^{c5}$ are identical or different and each represents hydroxyl, amino, or $C_{1-6}$ alkylamino;

$R^{c6}$ and $R^{c7}$ are identical or different and each represents hydrogen, $C_{1-6}$ alkyl, $C_{3-7}$ cycloalkyl optionally having hydroxyl, aromatic hydrocarbon, a saturated heterocyclic group, or an unsaturated heterocyclic group, or $R^{c6}$ and $R^{c7}$, taken together with the nitrogen to which they are attached, may form a saturated heterocyclic group; and $R^{c8}$ represents optionally substituted $C_{3-7}$ cycloalkyl or optionally substituted aromatic hydrocarbon.

Item 35C.

The use according to Item 34C, wherein the compound represented by Formula (a), (b), or (c) or a salt thereof is a compound represented by Formula (a) or a salt thereof.

Item 36C.

The use according to Item 35C, wherein the compound represented by Formula (a) or a salt thereof is a compound represented by Formula (d) below or a salt thereof;

Formula (d):

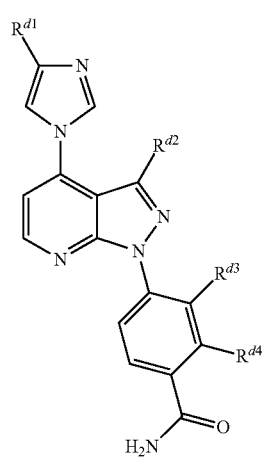

(d)

wherein $R^{d1}$ represents 1H-pyrazol-4-yl, 1-methyl-1H-pyrazol-4-yl, 1-ethyl-1H-pyrazol-4-yl, 1-isopropyl-1H-pyrazol-4-yl, pyridin-3-yl, pyridin-4-yl, or pyrimidin-5-yl;
$R^{d2}$ represents methyl, ethyl, n-propyl, isopropyl, n-butyl, isobutyl, sec-butyl, tert-butyl, or trifluoromethyl; and
$R^{d3}$ and $R^{d4}$ are such that $R^{d3}$ represents hydrogen, and $R^{d4}$ represents methyl, ethyl, n-propyl, amino, methylamino ($CH_3NH$—), or ethylamino ($CH_3CH_2NH$—), or that $R^{d4}$ represents hydrogen, and $R^{d3}$ represents methyl, ethyl, n-propyl, amino, methylamino ($CH_3NH$—), or ethylamino ($CH_3CH_2NH$—).

Item 37C.

The use according to any one of Items 32C to 36C, wherein the HSP90 family protein having a mutation in the site corresponding to F138 of HSP90α class A consisting of the amino acid sequence of SEQ ID NO: 1 is the protein according to any one of Items 1 to 11.

Item 38C.

The use according to any one of Items 32C to 37C, wherein the therapeutic agent is a therapeutic agent for tumors.

Item 31E.

A compound or a salt thereof, which is an HSP90 family inhibitory substance for use in the treatment of neurodegenerative disorder, tumor, autoimmune disease, or viral infection of a patient in which, in HSP90 family protein, a protein having a mutation in the site corresponding to F138 of HSP90α class A consisting of the amino acid sequence of SEQ ID NO: 1 is expressed.

Item 32E.

The compound or a salt thereof according to Item 31E for use in the treatment of neurodegenerative disorder, tumor, autoimmune disease, or viral infection of a patient in which, in HSP90 family protein, a protein having a mutation in the site corresponding to F138 of HSP90α class A consisting of the amino acid sequence of SEQ ID NO: 1 is expressed, wherein the compound or a salt thereof is an HSP90 family inhibitory substance that, in HSP90 family protein, fills a cavity in the vicinity of at least one amino acid selected from the group consisting of 5 amino acids in sites corresponding to F170, F22, G108, Y139, or W162 of HSP90α class A consisting of the amino acid sequence of SEQ ID NO: 1.

Item 33E.

The compound or a salt thereof according to Item 31E or Item 32E for use in the treatment of neurodegenerative disorder, tumor, autoimmune disease or viral infection of a patient in which, in HSP90 family protein, a protein having a mutation in the site corresponding to F138 of HSP90α class A consisting of the amino acid sequence of SEQ ID NO: 1 is expressed, wherein the compound or a salt thereof is an HSP90 family inhibitory substance that interacts with, in HSP90 family protein, at least one amino acid selected from the group consisting of 5 amino acids in sites corresponding to F170, F22, G108, Y139, or W162 of HSP90α class A consisting of the amino acid sequence of SEQ ID NO: 1.

Item 34E.

The compound represented by Formula (a), (b), or (c) below or a salt thereof according to any one of Items 31E to 33E, for use in the treatment of neurodegenerative disorder, tumor, autoimmune disease or viral infection of a patient in which, in HSP90 family protein, a protein having a mutation in the site corresponding to F138 of HSP90α class A consisting of the amino acid sequence of SEQ ID NO: 1 is expressed.

Formula (a):

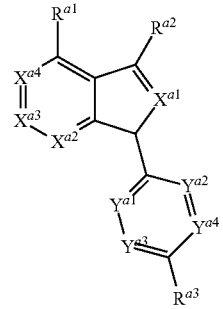

(a)

wherein $X^{a1}$ represents CH or N;
one of $X^{a2}$, $X^{a3}$, and $X^{a4}$ represents N, and the others each represent CH;
one or two of $Y^{a1}$, $Y^{a2}$, $Y^{a3}$, and $Y^{a4}$ represent C—$R^{a4}$, and the others are identical or different and each represents CH or N;
$R^{a1}$ represents an optionally substituted monocyclic or bicyclic unsaturated heterocyclic group having 1 to 4 heteroatoms selected from N, S, and O;
$R^{a2}$ represents hydrogen, optionally substituted $C_{1-6}$ alkyl, or optionally substituted $C_{2-6}$ alkenyl;
$R^{a3}$ represents cyano or —CO—$R^{a5}$;
$R^{a4}$s are identical or different and each represents hydrogen, halogen, cyano, optionally substituted $C_{1-6}$ alkyl, $C_{2-6}$ alkenyl, $C_{1-6}$ alkoxy, aromatic hydrocarbon, —N($R^{a6}$)($R^{a7}$), —S—$R^{a8}$, or —CO—$R^{a9}$;
$R^{a5}$ represents amino optionally having hydroxyl, or optionally substituted mono- or dialkylamino;
$R^{a6}$ and $R^{a7}$ are identical or different and each represents hydrogen, optionally substituted $C_{1-6}$ alkyl, $C_{1-6}$ halogenoalkyl, optionally substituted $C_{3-7}$ cycloalkyl, optionally substituted aralkyl, optionally substituted aromatic hydrocarbon, an optionally substituted saturated heterocyclic group, or an optionally substituted unsaturated heterocyclic group, or
$R^{a6}$ and $R^{a7}$, taken together with the nitrogen to which they are attached, may form a saturated heterocyclic group;
$R^{a8}$ represents optionally substituted $C_{3-7}$ cycloalkyl or optionally substituted aromatic hydrocarbon; and
$R^{a9}$ represents hydrogen, hydroxyl, amino optionally having hydroxyl, or optionally substituted mono- or dialkylamino, Formula (b):

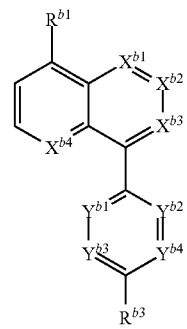

(b)

wherein at least one of $X^{b1}$, $X^{b2}$, $X^{b3}$, and $X^{b4}$ represents N or N-oxide, and the others are identical or different and each represents C—$R^{b2}$;

one or two of $Y^{b1}$, $Y^{b2}$, $Y^{b3}$, and $Y^{b4}$ represents C—$R^{b4}$, and the others are identical or different and each represents CH or N;

$R^{b1}$ represents an optionally substituted monocyclic or bicyclic unsaturated heterocyclic group having 1 to 4 heteroatoms selected from N, S, and O;

$R^{b2}$ represents hydrogen, optionally substituted $C_{1-6}$ alkyl, optionally substituted $C_{3-7}$ cycloalkyl, or optionally substituted $C_{2-6}$ alkenyl;

$R^{b3}$ represents hydrogen, halogen, cyano, $C_{1-6}$ alkyl, $C_{1-6}$ alkoxy, or —CO—$R^{b5}$;

$R^{b4}$ represents hydrogen, halogen, $C_{1-6}$ alkyl, $C_{1-6}$ alkoxy, —CO—$R^{b6}$, —N($R^{b7}$)($R^{b8}$), or —S—$R^{b9}$;

$R^{b5}$ represents hydroxyl, amino, or optionally substituted $C_{1-6}$ alkylamino;

$R^{b6}$ represents hydroxyl, amino optionally having hydroxyl, or optionally substituted $C_{1-6}$ alkylamino;

$R^{b7}$ and $R^{b8}$ are identical or different and each represents hydrogen, optionally substituted $C_{1-6}$ alkyl, optionally substituted $C_{3-7}$ cycloalkyl, optionally substituted aromatic hydrocarbon, an optionally substituted saturated heterocyclic group, or an optionally substituted unsaturated heterocyclic group, or $R^{b7}$ and $R^{b}$, taken together with the nitrogen to which they are attached, may form a saturated heterocyclic group; and $R^{b9}$ represents optionally substituted $C_{3-7}$ cycloalkyl or optionally substituted aromatic hydrocarbon, or Formula (c):

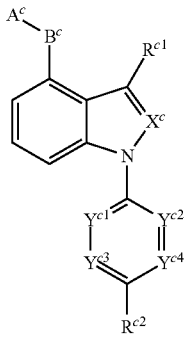

(c)

wherein $X^c$ represents CH or N;

one or two of $Y^{c1}$, $Y^{c2}$, $Y^{c3}$, and $Y^{c4}$ represent C—$R^{c3}$ or N, and the others each represent CH;

$A^c$ and $B^c$ are identical or different and each represents an optionally substituted monocyclic unsaturated heterocyclic group having 1 to 4 heteroatoms selected from N, S, and O;

$R^{c1}$ represents hydrogen, optionally substituted $C_{1-6}$ alkyl, optionally substituted $C_{3-7}$ cycloalkyl, or optionally substituted $C_{2-6}$ alkenyl;

$R^{c2}$ represents hydrogen, halogen, cyano, or —CO—$R^{c4}$;

$R^{c3}$ represents hydrogen, halogen, $C_{1-6}$ alkyl, $C_{1-6}$ alkoxy, —CO—$R^{c5}$, —N($R^{c6}$)($R^{c7}$), or —S—$R^{c8}$;

$R^{c4}$ and $R^{c5}$ are identical or different and each represents hydroxyl, amino, or $C_{1-6}$ alkylamino;

$R^{c6}$ and $R^{c7}$ are identical or different and each represents hydrogen, $C_{1-6}$ alkyl, $C_{3-7}$ cycloalkyl optionally having hydroxyl, aromatic hydrocarbon, a saturated heterocyclic group, or an unsaturated heterocyclic group, or $R^{c6}$ and $R^{c7}$, taken together with the nitrogen to which they are attached, may form a saturated heterocyclic group; and $R^{c8}$ represents optionally substituted $C_{3-7}$ cycloalkyl or optionally substituted aromatic hydrocarbon.

Item 35E.

The compound or a salt thereof according to Item 34E, wherein the compound or a salt thereof is the compound represented by Formula (a) or a salt thereof.

Item 36E.

The compound or a salt thereof according to Item 35E, wherein the compound or a salt thereof is the compound represented by Formula (d) below or a salt thereof.

Formula (d):

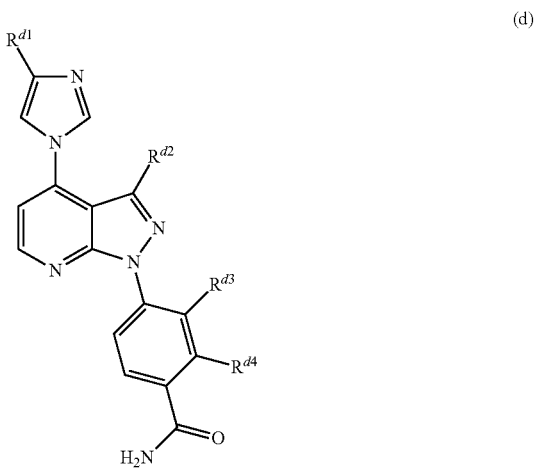

(d)

wherein $R^{d1}$ represents 1H-pyrazol-4-yl, 1-methyl-1H-pyrazol-4-yl, 1-ethyl-1H-pyrazol-4-yl, 1-isopropyl-1H-pyrazol-4-yl, pyridin-3-yl, pyridin-4-yl, or pyrimidin-5-yl;

$R^{d2}$ represents methyl, ethyl, n-propyl, isopropyl, n-butyl, isobutyl, sec-butyl, tert-butyl, or trifluoromethyl; and $R^{d3}$ and $R^{d4}$ are such that $R^{d3}$ represents hydrogen, and $R^{d4}$ represents methyl, ethyl, n-propyl, amino, methylamino ($CH_3NH$—), or ethylamino ($CH_3CH_2NH$—), or that $R^{d4}$ represents hydrogen, and $R^{d3}$ represents methyl, ethyl, n-propyl, amino, methylamino ($CH_3NH$—), or ethylamino ($CH_3CH_2NH$—).

Item 37E.

The compound or a salt thereof according to any one of Items 32E to 36E, wherein the HSP90 family protein having a mutation in the site corresponding to F138 of HSP90α class A consisting of the amino acid sequence of SEQ ID NO: 1 is the protein according to any one of Items 1 to 11.

Item 38E.

The compound or a salt thereof according to any one of Items 32E to 37E, wherein the treatment is treatment of tumor.

Item 51C.

Use of the therapeutic agent according to any one of Items 31 to 38, in the manufacture of a therapeutic agent for neurodegenerative disorder, tumor, autoimmune disease, or viral infection of a patient in which an HSP90 family protein having a mutation in the site corresponding to F138 of HSP90α class A consisting of the amino acid sequence of SEQ ID NO: 1 is expressed.

Item 52C.

The use according to Item 51C, wherein the patient is resistant to geldanamycin, 17-AAG, 17-DMAG, ganetespib (STA-9090), radicicol, BIIB021, SNX-2112, SNX-5422, AT13387, IPI-504, IPI-493, KW-2478, DS-2248, XL888, CUDC-305 (Debio0932), PU-H71, NVP-AUY922, HSP990, or MPC-3100.

Item 53C.

The use according to Item 51C or 52C, wherein the patient is a patient in which the protein according to any one of Items 1 to 11 is expressed.

Item 51E.

The therapeutic agent according to any one of Items 31 to 38, for use in the treatment of neurodegenerative disorder, tumor, autoimmune disease or viral infection of a patient in which an HSP90 family protein having a mutation in the site corresponding to F138 of HSP90α class A consisting of the amino acid sequence of SEQ ID NO: 1 is expressed.

Item 52E.

The therapeutic agent according to Item 51E, wherein the patient is resistant to geldanamycin, 17-AAG, 17-DMAG, ganetespib (STA-9090), radicicol, BIIB021, SNX-2112, SNX-5422, AT13387, IPI-504, IPI-493, KW-2478, DS-2248, XL888, CUDC-305 (Debio0932), PU-H71, NVP-AUY922, HSP990, or MPC-3100.

Item 53E.

The therapeutic agent according to Item 51E or 52E, wherein the patient is a patient in which the protein according to any one of Items 1 to 11 is expressed.

Advantageous Effects of Invention

The present invention enables screening of inhibitors against HSP90 that is resistant to known HSP90 inhibitors. Further, the present invention provides compounds having an inhibitory activity against HSP90 that is resistant to known HSP90 inhibitors. Since HSP90 inhibitors are considered effective as an antitumor agent, the present invention also provides antitumor agents, and methods for treating tumors, which are particularly effective for tumor patients resistant to known HSP90 inhibitors. The present invention also provides methods and agents for treating neurodegenerative disorders, autoimmune diseases, and viral infections. Further, the present invention enables a test for detecting patients resistant to known HSP90 inhibitors. The patients found by the test are expected to be effectively treated by the treatment using, in particular, the therapeutic agent or the therapeutic method of the present invention, and expected to improve the prognosis. Therefore, further effective personalized medical care becomes possible.

DESCRIPTION OF EMBODIMENTS

Figure 1:
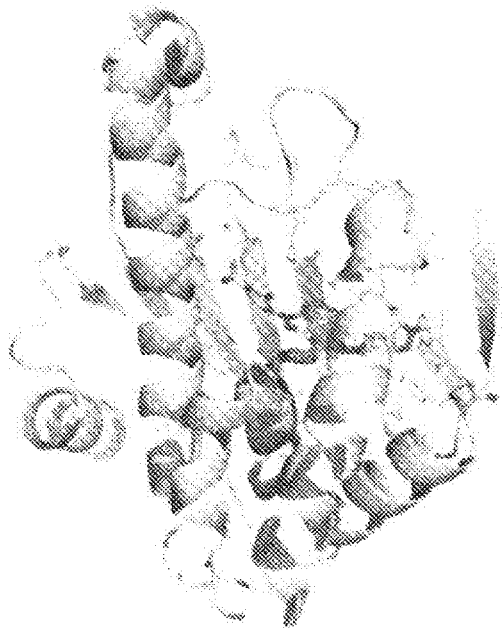
FIG. 1 is a diagram showing the binding mode of Synthesis Example 1 with respect to human wild-type HSP90α class A, clarified by X-ray co-crystal structural analysis.

The present invention encompasses a protein that is an HSP90 family protein having a mutation at a site corresponding to F138 of HSP90α class A consisting of the amino acid sequence of SEQ ID NO: 1. The present invention also encompasses a part (preferably a polypeptide) of the protein having the mutation.

HSP90 can be found in many species in nature, from *Escherichia coli* and yeasts to vertebrates (including mammals). Therefore, in this specification, the term "HSP90 family protein" encompasses all HSP90 of various biological species. The proteins included in the HSP90 family are not particularly limited, and may be any proteins of various species from prokaryotes to higher organisms, insofar as the protein is a molecular chaperone protein having a molecular weight of around 90 kDa and multiple functions including promotion of the formation of functional structures of other proteins and retention of the structures, promotion of correct association, inhibition of unnecessary aggregation, protection of other proteins from degradation, and promotion of secretion. Examples of the proteins include those disclosed in Gupta, R. S. (1995) Phylogenetic analysis of the 90 kD heat shock family of protein sequences and an examination of the relationship among animals, plants, and fungi species, Mol. Biol. Evol. 12: 1063-1073. In the present invention, eukaryotic HSP90 is particularly preferable, animal HSP90 is more preferable, vertebrate HSP90 is further preferable, vertebrate mammal HSP90 is still further preferable, rodent (such as rats or mice) HSP90 or primate (such as apes or humans) HSP90 is yet further preferable, and human HSP90 is particularly preferable.

Further, in this specification, HSP90 encompasses isoforms, splicing variants, mutants (including point mutation, insertion mutation, and deletion mutation), and derivatives of HSP90 protein; proteins cleaved from HSP90 precursor proteins; and proteins expressed by a fusion of HSP90 gene and another gene, insofar as they have the functions of HSP90.

In this specification, a particular site of the amino acid sequence of human HSP90 is indicated based on the amino acid sequences of the above accession numbers. For example, the 138th amino acid in the amino acid sequence (SEQ ID NO: 1) of human HSP90α class A (accession number: NP_005339.3) is phenylalanine, and is referred to as "F138." In this specification, "F138 of HSP90α class A" refers to F138 of HSP90α class A consisting of the amino acid sequence of SEQ ID NO: 1. Further, in this specification, "a site corresponding to F138 of HSP90α class A" refers to a site corresponding to F138 of HSP90α class A consisting of the amino acid sequence of SEQ ID NO: 1. This "site" is preferably an amino acid.

Further, the site corresponding to F138 of HSP90α class A consisting of the amino acid sequence of SEQ ID NO: 1 of an HSP90 family protein encompasses all sites corresponding to F138 of HSP90α class A consisting of the amino acid sequence of SEQ ID NO: 1 in the amino acid sequences of isoforms, splicing variants, mutants, and derivatives of HSP90 proteins; proteins cleaved from HSP90 precursor proteins; and proteins expressed by a fusion of HSP90 gene and another gene of various species from prokaryotes to higher organisms. In particular, specific preferable examples of the site corresponding to F138 of HSP90α class A in HSP90 family proteins include, in addition to the aforementioned F138 of HSP90α class A consisting of the amino acid sequence of SEQ ID NO: 1, phenylalanine (F133), which is the 133rd amino acid in the amino acid sequence (SEQ ID NO: 2) of human HSP90α class B (GenBank accession number NP_031381.2), and phenylalanine (F199), which is the 199th amino acid in the amino acid sequence (SEQ ID NO: 3) of human HSP90β (GenBank accession number NP_003290.1). In this specification, "F133 of HSP90α class B" refers to F133 of HSP90α class A consisting of the amino acid sequence of SEQ ID NO: 2, and "F199 of HSP90β" refers to F199 of HSP90β consisting of the amino acid sequence of SEQ ID NO: 3. Expressions such as "site corresponding to F138 of HSP90α class A (consisting of the amino acid sequence of SEQ ID NO: 1) in the HSP90 family proteins," "site corresponding to F133 of HSP90α class B (consisting of the amino acid sequence of SEQ ID NO: 2) in the HSP90 family proteins," and "site corresponding to F199 of HSP90β (consisting of the amino acid sequence of SEQ ID NO: 3) in the HSP90 family proteins" can have the same meaning.

Further, expressions such as "HSP90α class A," "HSP90α class B," or "HSP90β" mean specific HSP90. As explained above, since HSP90 encompasses isoforms, splicing variants, mutants (including point mutation, insertion mutation, and deletion mutation), and derivatives of HSP90 protein, proteins cleaved from HSP90 precursor proteins, and proteins expressed by a fusion of HSP90 gene and another gene (these proteins preferably have, in particular, the functions of HSP90), "HSP90α class A" also encompasses, for example, isoforms, splicing variants, mutants (including point mutation, insertion mutation, and deletion mutation), and derivatives of HSP90α class A protein, proteins cleaved from HSP90α class A precursor proteins, and proteins expressed by a fusion of HSP90α class A gene and another gene.

The HSP90 family protein having a mutation in the site corresponding to F138 of HSP90α class A consisting of the amino acid sequence of SEQ ID NO: 1 is preferably a protein in which the amino acid originally present in the site (i.e., the amino acid originally present in the site of wild-type) has a different mutation. Examples include an HSP90 protein having a structure in which the amino acid originally presents in the site is substituted with another amino acid or deleted; or another amino acid is added or inserted into the site. An HSP90 protein in which the amino acid originally presents in the site is phenylalanine and the amino acid has a mutation is preferable. The mutation in the site is preferably substitution, deletion, addition, or insertion, more preferably substitution. The mutation in the site may be a combination of substitution, deletion, addition, or insertion. The number of amino acids with substitution, deletion, addition, and/or insertion is preferably 1 to 20, more preferably 1 to 10, further preferably 1 to 5, further more preferably 1, 2, or 3, according to a counting method in which the number of amino acid mutations are minimally counted. The most preferable mutation is 1 amino acid substitution.

The mutated amino acid is not particularly limited insofar as it is an amino acid other than the amino acid originally present in the site. Preferable examples include 20 amino acids: glycine (G), alanine (A), valine (V), leucine (L), isoleucine (I), serine (S), threonine (T), cysteine (C), methionine (M), asparagine (N), glutamine (Q), proline (P), phenylalanine (F), thyrosine (Y), tryptophan (W), arginine (R), aspartic acid (D), glutamic acid (E), histidine (H), and lysine (K) (the capital letters in parenthesis are single-letter indications of the corresponding amino acid)). For example, when the amino acid originally present in the site is phenylalanine, the amino acid is preferably an amino acid other than phenylalanine, more preferably one of 19 amino acids resulting from excluding phenylalanine from the above 20 kinds of amino acids. For example, in the case where F138 is mutated to another amino acid, a capital letter showing the mutated amino acid is added after F138. For example, if F138 is mutated to leucine, it is referred to as "F138L."

Further, in the present invention, the HSP90 family protein having a mutation in the site corresponding to F138 of HSP90α class A consisting of the amino acid sequence of SEQ ID NO: 1 also encompasses a protein having substitution, deletion, addition, or insertion of another or more amino acids, in addition to the mutation in the site corresponding to F138. The number of amino acids with substitution, deletion, addition, or insertion is preferably 1 to 80, more preferably 1 to 60, further preferably 1 to 40, further more preferably 1 to 20, still further preferably 1 to 10, particularly preferably 1 to 5, and most preferably 1, 2, or 3, according to a counting method in which the number of amino acid mutations are minimally counted.

A preferable example of these proteins is a protein in which a known useful peptide is added to an HSP90 family protein having a mutation in the site corresponding to F138 of HSP90α class A consisting of the amino acid sequence of SEQ ID NO: 1. Examples of known useful peptides include tag peptide, linker peptide, and signal peptide. The linker peptide is not particularly limited, and may suitably be arranged. Known linker peptides may be used. Known tag peptides may be used as the tag peptide. For example, His-tag or FLAG-tag may be preferably used. Known signal peptides may be used as the signal peptide. The peptides may be added singly, or in a combination of two or more. The protein in which a known useful peptide or peptides are added may also have further substitution, deletion, addition, or insertion.

Regarding such an HSP90 family protein having a mutation in the site corresponding to F138 of HSP90α class A consisting of the amino acid sequence of SEQ ID NO: 1, the protein having substitution, deletion, addition, or insertion of one or more amino acids in addition to the mutation in F138 preferably has inferior binding ability with respect to at least one kind of known HSP90 inhibitor, compared with a protein consisting of an amino acid sequence of the specific HSP90 family protein without a mutation in the site corresponding to F138.

Examples of HSP90 family protein having a mutation in the site corresponding to F138 of HSP90α class A consisting of the amino acid sequence of SEQ ID NO: 1, or a part thereof include the following proteins.

(i-1) an HSP90α class A protein having a mutation in the amino acid corresponding to F138 of HSP90α class A consisting of the amino acid sequence of SEQ ID NO: 1 in HSP90α class A;

(i-2) the HSP90α class A protein according to (i-1) which the protein has a mutation at F138 in HSP90α class A consisting of the amino acid sequence of SEQ ID NO: 1;

(i-3) the HSP90α class A protein according to (i-1) or (i-2), wherein the mutation is substitution, deletion, addition, or insertion of amino acid;
(i-4) a protein consisting of an amino acid sequence of the HSP90α class A protein according to any one of (i-1) to (i-3), wherein one or more amino acids are substituted, deleted, added, or inserted at a site or sites other than the amino acid mutation in the site corresponding to F138;
(i-5) the protein according to (i-4), wherein the protein has inferior binding ability with respect to at least one kind of known HSP90 inhibitor, compared with HSP90α class A consisting of the amino acid sequence of SEQ ID NO: 1;
(ii-1), an HSP90α class B protein having a mutation in the amino acid corresponding to F133 of HSP90α class B consisting of the amino acid sequence of SEQ ID NO: 2 in HSP90α class B;
(ii-2) the HSP90α class B protein according to (ii-1) which the protein has a mutation at F133 in HSP90α class B consisting of the amino acid sequence of SEQ ID NO: 2;
(ii-3) the HSP90α class B protein according to (ii-1) or (ii-2), wherein the mutation is substitution, deletion, addition, or insertion of amino acid;
(ii-4) a protein consisting of the amino acid sequence of the HSP90α class B protein according to any one of (ii-1) to (ii-3), wherein one or more amino acids are substituted, deleted, added, or inserted at a site or sites other than the amino acid mutation in the site corresponding to F133;
(ii-5) the protein according to (ii-4), wherein the protein has inferior binding ability with respect to at least one kind of known HSP90 inhibitor, compared with HSP90α class B consisting of the amino acid sequence of SEQ ID NO: 2;
(iii-1) an HSP90β protein having a mutation in the amino acid corresponding to F199 of HSP90β consisting of the amino acid sequence of SEQ ID NO: 3 in HSP90β;
(iii-2) the HSP90β protein according to (iii-1) which is has a mutation at F199 in HSP90β consisting of the amino acid sequence of SEQ ID NO: 3;
(iii-3) the HSP90β protein according to (iii-1) or (iii-2), wherein the mutation is substitution, deletion, addition, or insertion of amino acid;
(iii-4) a protein consisting of the amino acid sequence of the HSP90β protein according to any one of (iii-1) to (iii-3), wherein one or more amino acids are substituted, deleted, added, or inserted at a site or sites other than the amino acid mutation in the site corresponding to F199;
(iii-5) the protein according to (iii-4), wherein the protein has inferior binding ability with respect to at least one kind of known HSP90 inhibitor, compared with HSP90β consisting of the amino acid sequence of SEQ ID NO: 3;
(iv-1) a protein having a mutation in the 137th amino acid in the amino acid sequence of SEQ ID NO: 4;
(iv-2) the protein according to (iv-1), wherein the mutation is substitution, deletion, addition, or insertion of amino acid;
(iv-3) a protein consisting of the amino acid sequence of the protein according to (iv-1) or (iv-2), wherein one or more amino acids are substituted, deleted, added, or inserted, in addition to the amino acid mutation in the 137th site of the amino acid sequence of SEQ ID NO: 4; or
(iv-4) the protein according to (iv-3), wherein the protein has inferior binding ability with respect to at least one kind of known HSP90 inhibitor, compared with a protein consisting of the amino acid sequence of SEQ ID NO: 4; and a part of these proteins.

The examples also include:
(i) an HSP90α class A protein consisting of the amino acid sequence of SEQ ID NO: 9;
(ii) an HSP90α class B protein consisting of the amino acid sequence of SEQ ID NO: 10;
(iii) an HSP90β protein consisting of the amino acid sequence of SEQ ID NO: 11; or
(iv) a protein consisting of the amino acid sequence of SEQ ID NO: 12.

The "Xaa" in SEQ ID NOS: 9 to 12 refers to one of 19 kinds of amino acid resulting from excluding phenylalanine from the above 20 kinds of amino acid.

The examples of proteins or a part thereof listed above preferably has the functions of HSP90. The above proteins according to (i-1) to (i-5), (ii-1) to (ii-5), (iii-1) to (iii-5), (i), (ii), and (iii) are examples of HSP90 family protein having a mutation in the site corresponding to F138 of HSP90α class A consisting of the amino acid sequence of SEQ ID NO: 1, and the proteins according to (iv-1) to (iv-5), and (iv) are examples of a part of the proteins.

Examples of known HSP90 inhibitors include geldanamycin, 17-AAG, 17-DMAG, ganetespib (STA-9090), radicicol, BIIB021, SNX-2112, SNX-5422, AT13387, IPI-504, IPI-493, KW-2478, DS-2248, XL888, CUDC-305 (Debio0932), PU-H71, NVP-AUY922, HSP990, MPC-3100, and the like. Of these, geldanamycin, NVP-AUY922, 17-AAG, BIIB021, and SNX-2112 are particularly preferable.

In this specification, "at least one kind of known HSP90 inhibitor" refers to at least one kind of HSP90 inhibitor selected from the group consisting of the known HSP90 inhibitors exemplified above, and is preferably at least one kind of HSP90 inhibitor selected from the group consisting of geldanamycin, NVP-AUY922, 17-AAG, BIIB021, and SNX-2112. Some of the structural formulas of these known HSP90 inhibitors are shown below.

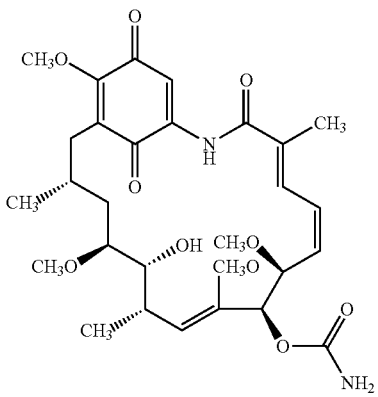

<Geldanamycin>

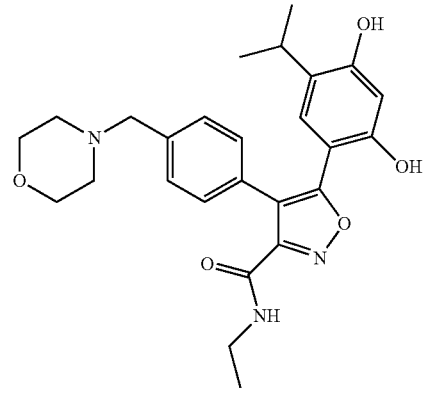

<NVP-AUY922>

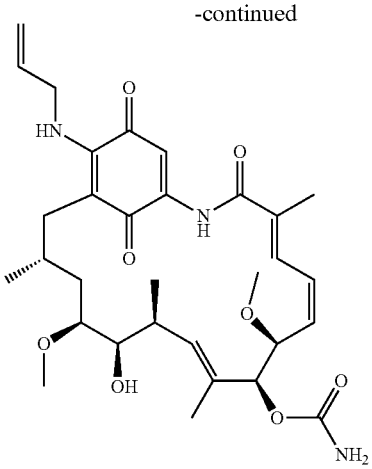

<17-AAG>

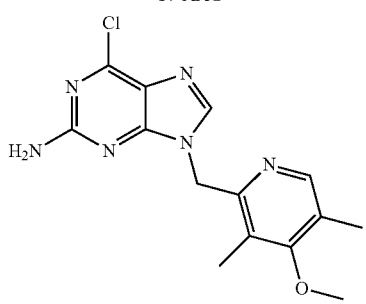

<BIIB021>

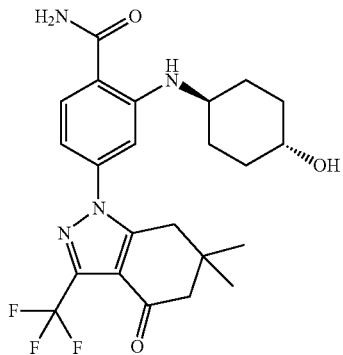

<SNX-2112>

The ability of each protein to bind to HSP90 inhibitors may be measured by comparing a fluorescence intensity upon the binding of each HSP90 family protein to a fluorescently labeled known HSP90 inhibitory substance with a fluorescence intensity upon the binding of each HSP90 family protein to a wild-type protein for comparison. However, the method for measuring the binding ability is not limited to this method. In the present invention, as long as the measurement of at least one method confirmed a decrease in binding ability, the binding ability with respect to HSP90 inhibitors can be regarded as decreased.

More specifically, for example, a competitive assay may be performed using 9th to 236th of the N-terminus domain of HSP90 (Anal. Biochem. 350 (2006) 202-213). This region in an HSP90 protein corresponds to a part around the ATP pocket of the N-terminus domain that is known to bind to a known HSP90 inhibitory substance.

As another example, an assay using an HSP90 function of folding the protein using ATP may also be used.

As still another example, an HSP90-dependent refolding assay that measures a denatured protein refolding ability, which is an ability of HSP90, may also be used. In this assay, a fluorescence signal intensity is measured using a fluorescent dye bonded to a hydrophobic surface based on a phenomenon such that more hydrophobic surfaces are exposed in a unfolded protein compared with a folded protein, thereby evaluating HSP90 functions (Bioorg. Med. Chem. 2007 Mar. 1; 15(5): 1939-1946.).

Further, as yet another example, an ATPase assay that measures the amount of the product resulting from hydrolysis of ATP by the ATPase activity of HSP90 (J. Biomol. Screen., 2010, 15: 279) may also be used. There is a report that the ATPase activity of HSP90 is retained even after deletion of the first 16 residues in the N-terminus domain of yeast HSP90 (J. Biol. Chem. 2002, 277:44905-44910).

For these evaluations of HSP90 inhibitors, the full length of HSP90 protein is not necessarily required, and the 9th to 236th are preferably included.

The present invention also encompasses a nucleic acid encoding the above protein or a part thereof, and a nucleic acid having a base sequence similar to the base sequence of the nucleic acid. In the explanation of the bases of a nucleic acid, A represents adenine, T represents thymine, G represents guanine, C represents cytosine, and U represents uracil. The nucleic acid of the present invention is preferably a polynucleotide (DNA or RNA). Although it is not particularly limited, DNA may preferably be cDNA, and RNA may preferably be mRNA. Preferable examples of nucleic acid of the present invention are shown below.

(i-a) a polynucleotide, which is DNA consisting of a base sequence in which the 412th to 414th base sequence of SEQ ID NO: 5 is mutated to a sequence encoding an amino acid other than phenylalanine; or RNA consisting of a base sequence in which T in the base sequence of the DNA is substituted with U;

(i-b) a polynucleotide encoding an HSP90α class A gene-splicing variant having a part or a plurality of parts of the polynucleotide according to (i-a);

(i-c) a polynucleotide that hybridizes with a polynucleotide consisting of a base sequence complementary to the base sequence of the polynucleotide according to (i-a) or (i-b) under a stringent condition, and encodes a protein having inferior binding ability with respect to at least one kind of known HSP90 inhibitor, compared with HSP90α class A;

(i-d) a polynucleotide comprising a base sequence having identity of not less than 80% with the base sequence of the polynucleotide according to (i-a) or (i-b), and encodes a protein having inferior binding ability with respect to at least one kind of known HSP90 inhibitor, compared with HSP90α class A;

(ii-a) a polynucleotide that is DNA consisting of a base sequence in which the 397th to 399th base sequence of SEQ ID NO: 6 is mutated to a sequence encoding an amino acid other than phenylalanine; or RNA consisting of a base sequence in which T in the base sequence of the DNA is substituted with U;

(ii-b) a polynucleotide encoding an HSP90α class B gene-splicing variant having a part or a plurality of parts of the polynucleotide according to (ii-a);

(ii-c) a polynucleotide that hybridizes with a polynucleotide consisting of a base sequence complementary to the base sequence of the polynucleotide according to (ii-a) or (ii-b) under a stringent condition, and encodes a protein having inferior binding ability with respect to at least one kind of known HSP90 inhibitor, compared with HSP90α class B;

(ii-d) a polynucleotide comprising a base sequence having identity of not less than 80% with the base sequence of the polynucleotide according to (ii-a) or (ii-b), and encodes a protein having inferior binding ability with respect to at least one kind of known HSP90 inhibitor, compared with HSP90α class B;

(iii-a) a polynucleotide, which is DNA consisting of a base sequence in which the 598th to 600th base sequence of SEQ ID NO: 7 is mutated to a sequence encoding an amino acid other than phenylalanine; or RNA consisting of a base sequence in which T in the base sequence of the DNA is substituted with U;

(iii-b) a polynucleotide encoding an HSP90β gene-splicing variant having a part or a plurality of parts of the polynucleotide according to (iii-a);

(iii-c) a polynucleotide that hybridizes with a polynucleotide consisting of a base sequence complementary to a base sequence of the polynucleotide according to (iii-a) or (iii-b) under a stringent condition, and encodes a protein having inferior binding ability with respect to at least one kind of known HSP90 inhibitor, compared with HSP90β;

(iii-d) a polynucleotide comprising a base sequence having identity of not less than 80% with the base sequence of the polynucleotide according to (iii-a) or (iii-b), and encodes a protein having inferior binding ability with respect to at least one kind of known HSP90 inhibitor, compared with HSP90β;

(iv-a) a polynucleotide, which is DNA consisting of a base sequence in which the 409th to 411th base sequence of SEQ ID NO: 8 is mutated to a sequence encoding an amino acid other than phenylalanine; or RNA consisting of a base sequence in which T in the base sequence of the DNA is substituted with U;

(iv-b) a polynucleotide that hybridizes with a polynucleotide consisting of a base sequence complementary to a base sequence of the polynucleotide according to (i-a) under a stringent condition, and encodes a protein having inferior binding ability with respect to at least one kind of known HSP90 inhibitor, compared with the protein consisting of the amino acid sequence of SEQ ID NO: 4; or (iv-c) a polynucleotide comprising a base sequence having identity of not less than 80% with the base sequence of the polynucleotide according to (i-a), and encodes a protein having inferior binding ability with respect to at least one kind of known HSP90 inhibitor, compared with the protein consisting of the amino acid sequence of SEQ ID NO: 4.

The "sequence encoding an amino acid other than phenylalanine" is a codon (in DNA, U in a codon is read as T) encoding an amino acid other than phenylalanine, and is preferably a codon other than a stop codon Further, the codon may be any codon known as a eukaryotic codon. Typical examples are shown in the table below.

TABLE 1

| Ala/A | Alanine GCU, GCC GCA, GCG | Leu/L | Leucine UUA UUG, CUU CUC, CUA, CUG |
|---|---|---|---|
| Arg/R | Arginine CGU, CGC, CGA, CGG, AGA, AGG | Lys/K | Lysine AAA, AAG |
| Asn/N | Asparagine AAU, AAC | Met/M | Methionine AUG |
| Asp/D | Aspartic acid GAU, GAC | Phe/F | Phenylalanine UUU, UUC |
| Cys/C | Cysteine UGU, UGC | Pro/P | Proline CCU, CCC, CCA, CCG |

TABLE 1-continued

| Gln/Q | Glutamine CAA, CAG | Ser/S | Serine UCU, UCC, UCA, UCG, AGU, AGC |
|---|---|---|---|
| Glu/E | Glutamic acid GAA, GAG | Thr/T | Threonine ACU, ACC, ACA, ACG |
| Gly/G | Glycine GGU, GGC, GGA, GGG | Trp/W | Tryptophan UGG |
| His/H | Histidine CAU, CAC | Tyr/Y | Thyrosine UAU, UAC |
| Ile/I | Isoleucine AUU, AUC, AUA | Val/V | Valine GUU, GUC, GUA, GUG |
| Start | AUG, (AUA), (GUG) | Stop | UAG, UGA, UAA |

Further, in this specification, "hybridization under a stringent condition" refers to a condition in which hybridization is performed at 50° C. in 2×SSC containing 0.1% SDS, and in which detachment does not occur upon washing at 60° C. in 1×SSC containing 0.1% SDS.

The protein or the nucleic acid of the present invention may be produced by a known method. For example, the nucleic acid may be produced by extracting DNA encoding HSP90 from an organism, and artificially mutating the DNA; the nucleic acid may also be produced by chemical synthesis. Examples of the artificial mutation method include, but are not particularly limited to, genetic engineering methods such as site-specific mutagenesis (Methods in Enzymology, 154, 350, 367-382 (1987) and 100, 468 (1983); Nucleic Acids Res., 12, 9441 (1984); Zoku seika-gaku jikken koza 1, "Idenshi kenkyu-ho II" [Continuation of biochemistry experiment lecture 1, "Gene study method II"], edited by The Japanese Biochemical Society, p. 105 (1986)); chemical synthesis means such as a phosphotriester method or phosphoramidite method (J. Am. Chem. Soc., 89, 4801 (1967) and 91, 3350 (1969); Science, 150, 178 (1968); Tetrahedron Lett., 22, 1859 (1981), and 24, 245 (1983)); and combinations of these methods. Further, for example, chemical synthesis may be performed by a phosphoramidite method or a phosphotriester method, or synthesis may be performed using an automated oligonucleotide synthesizer.

Further, the present invention also encompasses an antibody that recognizes an HSP90 family protein having a mutation in the site corresponding to F138 of HSP90α class A consisting of the amino acid sequence of SEQ ID NO: 1. The antibody may be a monoclonal antibody, a polyclonal antibody, or an antibody fragment (for example, F(ab) or F(ab')$_2$, camelid sdAb, peptides produced by phage display, or the like) having an antigen recognition site. Further, the antibody is preferably an antibody that specifically recognizes the protein.

Preferable examples of these antibodies include an antibody that recognizes the protein according to Item 10.

In particular, (α-1) an antibody that specifically recognizes an HSP90α class A protein having a mutation in the amino acid corresponding to F138 of HSP90α class A consisting of the amino acid sequence of SEQ ID NO: 1 in HSP90α class A; (β-1) an antibody that specifically recognizes an HSP90α class B protein having a mutation in the amino acid corresponding to F133 of HSP90α class B consisting of the amino acid sequence of SEQ ID NO: 2 in HSP90α class B;

(γ-1) an antibody that specifically recognizes an HSP90β protein having a mutation in the amino acid corresponding to F199 of HSP90β consisting of the amino acid sequence of SEQ ID NO: 3 in HSP90β; and (δ-1) an antibody that specifically recognizes a protein consisting of the amino acid sequence of SEQ ID NO: 12 are preferable. Of these, (α-2) the antibody according to (α-1), wherein the antibody has the mutation site in an epitope;
(β-2) the antibody according to (β-1), wherein the antibody has the mutation site in an epitope;
(γ-2) the antibody according to (γ-1), wherein the antibody has the mutation site in an epitope; or
(δ-2) the antibody according to (δ-1), wherein the antibody has Xaa site in SEQ ID NO: 12;
are preferable.

Such an antibody can be produced by a known method using, for example, an HSP90 family protein having a mutation in the site corresponding to F138 of HSP90α class A consisting of the amino acid sequence of SEQ ID NO: 1 (or, a part of polypeptides of the protein including the mutation site) as an antigen (immunogen). When the protein is used as an immunogen, it may be used with an adjuvant such as Freund's Complete Adjuvant or Lipid A. For example, it is possible that the immunogen is subcutaneously injected into a rodent, a house rabbit, or chicken with several boosters every 3 or 4 days, blood drawing is performed a week after the final immunization, and a polyclonal antibody is purified. Further, for example, it is also possible that an immunogen is intraperitoneally administered to several rodents (such as mice) with several boosters every 3 or 4 days, blood drawing is performed a week after the final immunization, the antibody titer of the blood serum is measured by ELISA, a mouse with the highest titer is selected, the splenocyte is extracted from the mouse and fused with myeloma cells using a PEG (polyethylene glycol) method or the like, the fused cells are cultured with hybridoma selection medium (HAT medium), hybridoma is selected, and that positive clone screening, cloning, antibody titer measurement and the like are performed, thereby selecting a hybridoma that produces the target monoclonal antibody.

As described below, the antibody of the present invention can be used to detect the presence/absence of a mutation in the site corresponding to F138 of HSP90α class A consisting of the amino acid sequence of SEQ ID NO: 1 in an HSP90 family protein, and may also be used as an inhibitor against HSP90 having the mutation. In particular, antibodies (for example, the antibodies according to (α-2) to (δ-2)) that bind to the mutation site are preferable as such an inhibitor. Therefore, the antibody may be used as an active ingredient of the therapeutic agent of the present invention, which is described later.

Further, the present invention also encompasses a probe or a primer for recognizing a nucleic acid consisting of a base sequence that encodes an HSP90 family protein and has a mutation in the site corresponding to F138 of HSP90α class A consisting of the amino acid sequence of SEQ ID NO: 1. Preferably, the present invention also encompasses a probe or a primer for recognizing the above nucleic acids (for example, the nucleic acid according to any one of Items 12 and 13a to 13c). The expression "a base sequence having a mutation in the site corresponding to F138" preferably means a base sequence having a base mutation encoding an amino acid different from wild-type amino acid (preferably phenylalanine) at three bases encoding the amino acid corresponding to F138.

The probe is preferably a probe consisting of a nucleic acid that hybridizes with these polynucleotides under a stringent condition. The probe is preferably a nucleic acid (for example, DNA, RNA, or PNA). Further, since the nucleic acid to be detectable by the probe has a mutation in the site corresponding to F138 of HSP90α class A consisting of the amino acid sequence of SEQ ID NO: 1, the probe is preferably a polynucleotide having a structure that enables highly sensitive detection of the mutation. Examples of such a structure include a known structure used for a probe for detecting single-nucleotide polymorphism (SNPs). Preferable examples of polynucleotide having such a structure include an oligonucleotide with the 5' end modified with a fluorescent material (for example, FAM or VIC), and the 3' end modified with a quencher of the fluorescent material. The oligonucleotide contains a base that is not complementary to the mutation site. The probe having such a structure is known as a TaqMan® probe. Further, preferable examples of the primer include sequence primers for sequencing the mutation site and PCR primers. The primer is preferably a polynucleotide having a structure that enables highly sensitive detection of a mutation in the site corresponding to F138 of HSP90α class A consisting of the amino acid sequence of SEQ ID NO: 1, as in the probes. Examples of the sequence primer include a primer capable of sequencing the mutation site. Further, preferable examples of PCR primer include a primer having a base sequence, by which the primer can hybridize in a way its 3' end oppose to the mutation site, while the base at the 3' end is not complementary to the base of the mutation site. The base chain of such a primer does not elongate by PCR in some conditions; thus, it is possible to detect the mutation according to the presence/absence of amplification by PCR. A PCR primer set having a forward primer and a reverse primer, one of which has the above structure, is preferable. The above probes and primers are only examples, and the present invention is not limited to these probes and primers.

The present invention also provides a method for screening a substance for inhibiting HSP90 (preferably an HSP90 family protein having a mutation in the site corresponding to F138 of HSP90α class A consisting of the amino acid sequence of SEQ ID NO: 1).

The screening method comprises applying a test substance to an HSP90 family protein having a mutation in the site corresponding to F138 of HSP90α class A consisting of the amino acid sequence of SEQ ID NO: 1, and measuring the activity of the HSP90 family protein or the binding activity between the HSP90 family protein and the test substance. After the test substance is applied, if the activity of the HSP90 family protein is weakened, or if the binding activity between the HSP90 family protein and the test substance is found to be greater than the binding activity when the same test substance is applied to the HSP90 family protein that does not have the mutation, the test substance is selected as the target inhibitory substance.

The activity of the HSP90 family protein to be measured in the above method is not limited, insofar as it is an activity of known HSP90. For example, in view of ease of measurement, ATP degradation activity is preferable. This activity can be measured by a known method. For example, ATP degradation activity can be measured by quantitative determination of inorganic phosphate (Pi) generated by ATP→ADP+Pi hydrolysis reaction (the larger the Pi amount, the higher the activity).

The binding activity between the HSP90 family protein and the test substance measured by the above method can be determined by, for example, measuring a fluorescence intensity at the binding of a fluorescently labeled known HSP90 inhibitory substance with an HSP90 family protein as an index, and then measuring the extent of a decrease in fluorescence intensity when the test substance is added to the system (the greater decrease in fluorescence intensity, the higher the binding activity of the test substance). Preferable examples of known HSP90 inhibitory substances used herein include the known HSP90 inhibitors listed above. Geldanamycin, NVP-AUY922, 17-AAG, BIIB021, and SNX-2112 are more preferable, and geldanamycin is further preferable. The fluorescent label is not particularly limited, and any known fluorescent labels, such as various CyDyes, may be used according to the known HSP90 inhibitory substance to be used.

For the HSP90 family protein having a mutation in the site corresponding to F138 of HSP90α class A consisting of the amino acid sequence of SEQ ID NO: 1, for example, the proteins or a part thereof according to Items 1 to 11 (preferably Item 10 or 11) may be used. These proteins or a part thereof preferably have the functions of HSP90.

Further, in this screening method, the test substance may be applied to a purified HSP90 family protein having a mutation in the site corresponding to F138 of HSP90α class A consisting of the amino acid sequence of SEQ ID NO: 1; the test substance may otherwise be applied to cells expressing the protein. Additionally, when the test substance is applied to the cells, the activity of the HSP90 family protein may be measured based on the cell growth suppression rate or the cell decrease rate after the test substance was applied. This is because many of the proteins in which HSP90 is involved as molecular chaperone is relevant to cell growth; therefore, if the activity of HSP90 is inhibited, cell growth is suppressed, or cell death may even occur.

The cells may be cultured cells, or transplanted cells implanted into an animal (for example, mice, rats, rabbits, or apes). The cells are preferably tumor cells. The transplanted cells may be cells implanted to an internal part of the body, or cells implanted to an external part (epidermis) of the body. The transplanted cells are preferably derived from the same kind of animal.

In the case of using cultured cells, the test substance may be applied, for example, by being added to culture medium. Further, in the case of using transplanted cells, the test substance may be applied directly to the transplanted cells. It is also possible to apply the test substance through administration (for example, oral administration, or intravenous administration) to an animal in which the cells were transplanted.

The HSP90 family protein having a mutation in the site corresponding to F138 of HSP90α class A consisting of the amino acid sequence of SEQ ID NO: 1 may be expressed in cells by incorporating a polynucleotide encoding the protein (for example, the polynucleotide according to (i-a) to (i-d), (ii-a) to (ii-d), (iii-a) to (iii-d), and (iv-a) to (iv-d); DNA is particularly preferable) into an appropriate expression vector, and transfecting the vector to appropriate cells, thereby causing the protein to be expressed in the cells. Examples of cells include, although it depends on the expression vector, *Escherichia coli*, yeasts, insect cells, and mammal-derived cultured cells. Further, instead of using an expression vector, it is also possible to synthesize the protein by using a cell-free protein synthesizing system (for example, a rabbit reticulocyte-derived synthesizing system, wheat germ-derived synthesizing system, or *Escherichia coli*-derived synthesizing system). Further, it is also possible to purify the expressed protein or synthesized protein using a known method. For example, when a vector that causes expression by fusing a tag peptide (such as His-tag or FLAG-tag) with the target protein is used as the expression vector, the protein may be purified using the tag peptide.

Further, the polynucleotide encoding the HSP90 family protein having a mutation in the site corresponding to F138 of HSP90α class A may be designed and produced based on the base sequences of HSP90 genes in various known organisms. For example, it is possible that DNA consisting of a base sequence encoding HSP90α class A is incorporated in an appropriate vector, and a mutation is inserted into the base sequence by using a PCR primer or a commercially available kit for mutating the sequence encoding F138. The polynucleotide may otherwise be produced by chemical synthesis.

The present invention also encompasses a vector including such a polynucleotide, cells including the vector, cells (for example, *Escherichia coli*, yeasts, insect cells, or mammal-derived cultured cells) expressing an HSP90 family protein having a mutation in the site corresponding to F138 of HSP90α class A, and an animal into which these cells were transplanted (in particular, a mammal).

The present invention also encompasses a test method comprising detecting the presence/absence of a mutation in the site corresponding to F138 of HSP90α class A consisting of the amino acid sequence of SEQ ID NO: 1 in HSP90 family protein in a biological sample obtained from a test subject, and determining that the biological sample from which the mutation was detected is a test subject-derived sample resistant to known HSP90 inhibitors.

Examples of the test subject for obtaining a biological sample include biological species, which are not only limited to humans. The test subject is preferably a mammal, and more preferably a rodent (such as mice or rats) or a primate (such as humans or apes), and further preferably a human. Further, preferable examples of the biological sample include blood and tumors (preferably tumor cells or tumor lump).

Further, examples of the method for detecting the presence/absence of a mutation in the site corresponding to F138 of HSP90α class A consisting of the amino acid sequence of SEQ ID NO: 1 in HSP90 family protein include the above methods using an antibody, a probe, or a primer. Among them, for example, the antibodies according to (α-2) to (6-2) are particularly preferable, as they are capable of specifically recognizing the mutation. Further, for example, the probe according to Item 15 or 16 is preferable.

More specifically, after a protein or a nucleic acid is extracted from a biological sample, it is possible that, for a protein, the presence/absence of the mutation is detected using the above antibody through, for example, Western blotting, ELISA (Enzyme-Linked ImmunoSorbent Assay), an immunostaining method, or the like; and for a nucleic acid, the presence/absence of the mutation is detected using the above antibody through, for example, various hybridization methods (including Southern blots and Northern blots), PCR, or the like.

When the test subject from which the biological sample is obtained is a human, in particular, detection of the presence/absence of a mutation in the amino acid corresponding to F138 in HSP90α class A consisting of the amino acid sequence of SEQ ID NO: 1 in human HSP90α class A; a mutation in the amino acid corresponding to F133 of HSP90α class A consisting of the amino acid sequence of SEQ ID NO: 2 in human HSP90α class B; or a mutation in the amino acid corresponding to F199 of HSP90β consisting of the amino acid sequence of SEQ ID NO: 3 in human HSP90β is performed. Then, the biological sample from which the mutation was detected is determined to be resistant to known HSP90 inhibitors.

As another example, a method of measuring mutation of the polynucleotide encoding the protein may be used as a method for detecting the presence/absence of a mutation in the site corresponding to F138 of HSP90α class A consisting of the amino acid sequence of SEQ ID NO: 1 in HSP90 family protein. The method of measuring mutation of the polynucleotide is not particularly limited, and known methods may be used. For example, in view of simplicity, determination of the base sequence using sequencing, detection of mutation by a FISH method, a SNP detection method, or the like may be used. More specifically, for example, the presence of the mutation may be detected by extracting a nucleic acid (in particular, DNA) from a biological sample, determining a base sequence encoding HSP90, and comparing the base sequence with the base sequence of a wild-type. The presence of the mutation can be determined when the site corresponding to F138 of HSP90α class A encodes an amino acid other than phenylalanine, or when the site corresponding to F138 is deleted. The mutation may also be detected using the probes or primers described above.

The present invention also encompasses a determination that, when the sample is determined to be derived from a subject resistant to known HSP90 inhibitors, the test subject from which the sample was obtained is resistant to known HSP90 inhibitors. This method detects the presence/absence of a mutation in the site corresponding to F138 of HSP90α class A consisting of the amino acid sequence of SEQ ID NO: 1 in HSP90 family protein in a biological sample obtained from a test subject, and determines that the biological sample is resistant to known HSP90 inhibitors when the mutation is detected.

In particular, for biological samples of patients with neurodegenerative disorders, autoimmune diseases, viral infections, or tumors (in particular, biological samples obtained from tumor patients or malignant tumors), the method of determining that the sample is derived from a subject resistant to known HSP90 inhibitors, and the method of determining that the subject is a subject resistant to known HSP90 inhibitors are useful for personalized medical care. More specifically, for example, in tumor treatments, although HSP90 inhibitors can be used as a therapeutic agent (antitumor agent) that ensures an effective antitumor potency as described above, such an antitumor effect of the known HSP90 inhibitors will hardly take effect if the patient is resistant to known HSP90 inhibitors. Accordingly, if the subject or the biological sample can be determined to be resistant to known HSP90 inhibitors, unnecessary administration of known HSP90 inhibitors that actually provide no effect can be avoided during tumor treatments. Further, it is also a benefit for tumor patients, as they can avoid side effects of known HSP90 inhibitors. Further, as described below in detail, the present invention also includes a therapeutic agent to be used for patients in which an HSP90 family protein having a mutation in the site corresponding to F138 of HSP90α class A consisting of the amino acid sequence of SEQ ID NO: 1 is expressed in HSP90 family protein. Since the therapeutic agent is particularly useful for patients resistant to known HSP90 inhibitors, the method is also useful as a method for selecting patients treatable by the therapeutic agent.

Further, the present invention also encompasses a kit to be used for the above method. The kit includes a reagent for detecting the presence/absence of a mutation in the site corresponding to F138 of HSP90α class A in HSP90 family protein. Examples of the reagent include antibodies, probes, and primers (in particular, polynucleotides) for detecting the mutation. Examples of the antibodies include, but are not particularly limited to, the antibodies according to (α-1) to (δ-1), and (α-2) to (δ-2). Examples of the probes and the primers include, but are not particularly limited to, sequence primers for sequencing the mutation site, primers capable of detecting the mutation site by real-time PCR, and TaqMan probes.

The present invention also encompasses a therapeutic agent to be used for patients in which a protein having a mutation in the site corresponding to F138 of HSP90α class A consisting of the amino acid sequence of SEQ ID NO: 1 is expressed in HSP90 family protein; the therapeutic agent comprises a compound or a salt thereof for inhibiting a protein having a mutation in the site corresponding to F138 of HSP90α class A consisting of the amino acid sequence of SEQ ID NO: 1 in HSP90 family protein. The present invention preferably also encompasses a therapeutic agent comprising a compound or a salt thereof that fills a cavity in the vicinity of at least one amino acid selected from the group consisting of 5 amino acids in sites corresponding to F170, F22, G108, Y139, or W162 of HSP90α class A consisting of the amino acid sequence of SEQ ID NO: 1, in the proteins belonging to the HSP90 family or a part thereof. The present invention further preferably also encompasses a therapeutic agent comprising a compound or a salt thereof that interacts with at least one amino acid selected from the group consisting of 5 amino acids in sites corresponding to F170, F22, G108, Y139, or W162 of HSP90α class A consisting of the amino acid sequence of SEQ ID NO: 1, in the proteins belonging to the HSP90 family. The "interaction" means, for example, covalent bonds or noncovalent bonds. Examples of noncovalent bonds include intermolecular van der Waals binding, π-π interaction, hydrophobic bonds, hydrogen bonds, and electrostatic interaction. The five described amino acids are amino acids that desirably interact with a compound represented by Formula (a), (b), or (c) below, when the compound binds to an HSP90 family protein. Further, the above method for screening an HSP90 inhibitory substance is capable of desirably screening the compound that fills a cavity in the vicinity of the amino acid, or the compound that interacts with the amino acid.

The therapeutic agent is particularly effective for diseased cells in which the HSP90 family protein having a mutation in the site corresponding to F138 of HSP90α class A consisting of the amino acid sequence of SEQ ID NO: 1 is expressed. For example, when the therapeutic agent is an antitumor agent, the agent is particularly effective for tumor cells.

Specifically, the present invention encompasses a therapeutic agent for treating a patient in which, in an HSP90 family protein, a protein having a mutation in the site corresponding to F138 of HSP90α class A consisting of the amino acid sequence of SEQ ID NO: 1 is expressed, the therapeutic agent comprising a compound represented by Formula (a), (b), or (c) below, or a salt thereof;

Formula (a):

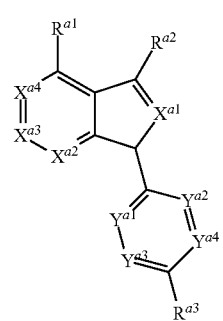

(a)

wherein $X^a$ represents CH or N;
one of $X^a$, $X^{a3}$, and $X^{a4}$ represents N, and the others each represent CH;

one or two of $Y^{a1}$, $Y^{a2}$, $Y^{a3}$, and $Y^{a4}$ represent C—$R^{a4}$, and the others are identical or different and each represents CH or N; and $R^{a1}$, $R^{a2}$, $R^{a3}$, $R^{a4}$, $R^{a6}$, $R^{a7}$, $R^{a8}$, and $R^{a9}$ are not particularly defined, Formula (b):

(b)

[Chemical structure showing $R^{b1}$, $X^{b1}$, $X^{b2}$, $X^{b3}$, $X^{b4}$, $Y^{b1}$, $Y^{b2}$, $Y^{b3}$, $Y^{b4}$, $R^{b3}$]

wherein at least one of $X^{b1}$, $X^{b2}$, $X^{b3}$, and $X^{b4}$ represents N or N-oxide, and the others are identical or different and each represents C—$R^{b2}$;

one or two of $Y^{b1}$, $Y^{b2}$, $Y^{b3}$, and $Y^{b4}$ represent C—$R^{b4}$, and the others are identical or different and each represents CH or N; and $R^{b1}$, $R^{b2}$, $R^{b3}$, $R^{b4}$, $R^{b5}$, $R^{b6}$, $R^{b7}$, $R^{b8}$, and $R^{b9}$ are not particularly defined, or Formula (c):

(c)

[Chemical structure showing $A^c$, $B^c$, $R^{c1}$, $X^c$, $Y^{c1}$, $Y^{c2}$, $Y^{c3}$, $Y^{c4}$, $R^{c2}$]

wherein $X^c$ represents CH or N;

one or two of $Y^{c1}$, $Y^{c2}$, $Y^{c3}$, and $Y^{c4}$ represent C—$R^{c3}$ or N, and the others each represent CH;

$A^c$ and $B^c$ are identical or different and each represents an optionally substituted monocyclic unsaturated heterocyclic group having 1 to 4 heteroatoms selected from N, S, and O; and $R^{c1}$, $R^{c2}$, $R^{c3}$, $R^{c4}$, $R^{c5}$, $R^{c6}$, $R^{c7}$, and $R^{c8}$ are not particularly defined. More preferably, the present invention encompasses a therapeutic agent for treating a patient in which, in an HSP90 family protein, a protein having a mutation in the site corresponding to F138 of HSP90α class A consisting of the amino acid sequence of SEQ ID NO: 1 is expressed, the therapeutic agent comprising a compound represented by Formula (a), (b), or (c) below, or a salt thereof;

Formula (a):

(a)

[Chemical structure showing $R^{a1}$, $R^{a2}$, $X^{a1}$, $X^{a2}$, $X^{a3}$, $X^{a4}$, $Y^{a1}$, $Y^{a2}$, $Y^{a3}$, $Y^{a4}$, $R^{a3}$]

wherein $X^{a1}$ represents CH or N;

one of $X^a$, $X^{a3}$, and $X^{a4}$ represents N, and the others each represent CH;

one or two of $Y^{a1}$, $Y^{a2}$, $Y^{a3}$, and $Y^{a4}$ represent C—$R^{a4}$, and the others are identical or different and each represents CH or N;

$R^{a1}$ represents an optionally substituted monocyclic or bicyclic unsaturated heterocyclic group having 1 to 4 heteroatoms selected from N, S, and O;

$R^{a2}$ represents hydrogen, optionally substituted $C_{1-6}$ alkyl, or optionally substituted $C_{2-6}$ alkenyl;

$R^{a3}$ represents cyano or —CO—$R^5$;

$R^{a4}$s are identical or different and each represents hydrogen, halogen, cyano, optionally substituted $C_{1-6}$ alkyl, $C_{2-6}$ alkenyl, $C_{1-6}$ alkoxy, aromatic hydrocarbon, —N($R^{a6}$)($R^{a7}$), —S—$R^{a8}$, or —CO—$R^{a9}$;

$R^{a5}$ represents amino optionally having hydroxyl, or optionally substituted mono- or dialkylamino;

$R^{a6}$ and $R^{a7}$ are identical or different and each represents hydrogen, optionally substituted $C_{1-6}$ alkyl, $C_{1-6}$ halogenoalkyl, optionally substituted $C_{3-7}$ cycloalkyl, optionally substituted aralkyl, optionally substituted aromatic hydrocarbon, an optionally substituted saturated heterocyclic group, or an optionally substituted unsaturated heterocyclic group, or $R^{a6}$ and $R^{a7}$, taken together with the nitrogen to which they are attached, may form a saturated heterocyclic group;

$R^{a8}$ represents optionally substituted $C_{3-7}$ cycloalkyl or optionally substituted aromatic hydrocarbon; and $R^{a9}$ represents hydrogen, hydroxyl, amino optionally having hydroxyl, or optionally substituted mono- or dialkylamino, Formula (b):

(b)

[Chemical structure showing $R^{b1}$, $X^{b1}$, $X^{b2}$, $X^{b3}$, $X^{b4}$, $Y^{b1}$, $Y^{b2}$, $Y^{b3}$, $Y^{b4}$, $R^{b3}$]

wherein at least one of $X^{b1}$, $X^{b2}$, $X^{b3}$, and $X^{b4}$ represents N or N-oxide, and the others are identical or different and each represents C—$R^{b2}$;

one or two of $Y^{b1}$, $Y^{b2}$, $Y^{b3}$, and $Y^{b4}$ represents C—$R^{b4}$, and the others are identical or different and each represents CH or N;

$R^{b1}$ represents an optionally substituted monocyclic or bicyclic unsaturated heterocyclic group having 1 to 4 heteroatoms selected from N, S, and O;

$R^{b2}$ represents hydrogen, optionally substituted $C_{1-6}$ alkyl, optionally substituted $C_{3-7}$ cycloalkyl, or optionally substituted $C_{2-6}$ alkenyl;

$R^{b3}$ represents hydrogen, halogen, cyano, $C_{1-6}$ alkyl, $C_{1-6}$ alkoxy, or —CO—$R^{b5}$;

$R^{b4}$ represents hydrogen, halogen, $C_{1-6}$ alkyl, $C_{1-6}$ alkoxy, —CO—$R^{b6}$, —N($R^{b7}$)($R^{b8}$), or —S—$R^{b9}$;

$R^{b5}$ represents hydroxyl, amino, or optionally substituted $C_{1-6}$ alkylamino;

$R^{b6}$ represents hydroxyl, amino optionally having hydroxyl, or optionally substituted $C_{1-6}$ alkylamino;

$R^{b7}$ and $R^{b8}$ are identical or different and each represents hydrogen, optionally substituted $C_{1-6}$ alkyl, optionally substituted $C_{3-7}$ cycloalkyl, optionally substituted aromatic hydrocarbon, an optionally substituted saturated heterocyclic group, or an optionally substituted unsaturated heterocyclic group, or $R^{b7}$ and $R^{b8}$, taken together with the nitrogen to which they are attached, may form a saturated heterocyclic group; and $R^{b9}$ represents optionally substituted $C_{3-7}$ cycloalkyl or optionally substituted aromatic hydrocarbon, or Formula (c):

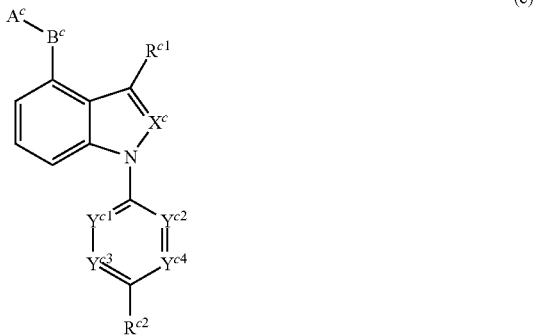

(c)

wherein $X^c$ represents CH or N;

one or two of $Y^{c1}$, $Y^{c2}$, $Y^{c3}$, and $Y^{c4}$ represent C—$R^{c3}$ or N, and the others each represent CH;

$A^c$ and $B^c$ are identical or different and each represents an optionally substituted monocyclic unsaturated heterocyclic group having 1 to 4 heteroatoms selected from N, S, and O;

$R^{c1}$ represents hydrogen, optionally substituted $C_{1-6}$ alkyl, optionally substituted $C_{3-7}$ cycloalkyl, or optionally substituted $C_{2-6}$ alkenyl;

$R^{c2}$ represents hydrogen, halogen, cyano, or —CO—$R^{c4}$;

$R^{c3}$ represents hydrogen, halogen, $C_{1-6}$ alkyl, $C_{1-6}$ alkoxy, —CO—$R^{c5}$, —N($R^{c6}$)($R^{c7}$), or —S—$R^{c8}$;

$R^{c4}$ and $R^{c5}$ are identical or different and each represents hydroxyl, amino, or $C_{1-6}$ alkylamino;

$R^{c6}$ and $R^{c7}$ are identical or different and each represents hydrogen, $C_{1-6}$ alkyl, $C_{3-7}$ cycloalkyl optionally having hydroxyl, aromatic hydrocarbon, a saturated heterocyclic group, or an unsaturated heterocyclic group, or $R^{c6}$ and $R^{c7}$, taken together with the nitrogen to which they are attached, may form a saturated heterocyclic group; and $R^{c8}$ represents optionally substituted $C_{3-7}$ cycloalkyl or optionally substituted aromatic hydrocarbon.

The following sequentially describes the compounds represented by Formulas (a), (b), and (c).

First, the compounds represented by Formula (a) are described. Examples of substituents for Formula (a) include halogen, hydroxyl, cyano, nitro, alkyl, halogenoalkyl, cycloalkyl, cycloalkyl-alkyl, aralkyl, hydroxyalkyl, alkenyl, alkynyl, alkoxy, halogenoalkoxy, alkoxy-alkyl, cycloalkoxy, cycloalkyl-alkoxy, aralkyloxy, aralkyloxy-alkyl, alkylthio, cycloalkyl-alkylthio, amino, mono- or dialkylamino, cycloalkyl-alkylamino, acyl, acyloxy, oxo, carboxyl, alkoxycarbonyl, aralkyloxycarbonyl, carbamoyl, saturated or unsaturated heterocyclic group, aromatic hydrocarbon, saturated heterocyclic oxy group, and the like. The number of the substituents, if any, is typically 1 to 3.

Examples of the halogen included in the substituents include chlorine, bromine, fluorine, and iodine.

The alkyl or halogenoalkyl included in the substituents preferably refers to a straight or branched $C_{1-6}$ alkyl group or a group in which one to all of the hydrogen atoms of the alkyl group are substituted with the halogen mentioned above. Examples thereof include alkyl groups such as methyl, ethyl, n-propyl, isopropyl, n-butyl, isobutyl, sec-butyl, tert-butyl, pentyl, and hexyl; halogenoalkyl groups such as trifluoromethyl; and the like.

The cycloalkyl included in the substituents preferably refers to a $C_{3-7}$ cycloalkyl group. Examples thereof include cyclopropyl, cyclobutyl, cyclopentyl, cyclohexyl, cycloheptyl, and the like.

The cycloalkyl-alkyl included in the substituents preferably refers to a $C_{1-6}$ alkyl group that is substituted with a $C_{3-7}$ cycloalkyl group. Examples thereof include cyclopropylmethyl, cyclopropylethyl, cyclobutylmethyl, cyclopentylmethyl, cyclohexylmethyl, and the like.

The aralkyl included in the substituents preferably refers to a straight or branched $C_{1-6}$ alkyl group that is substituted with a $C_{6-14}$ aromatic hydrocarbon group. Examples thereof include benzyl, phenylethyl, phenylpropyl, naphthylmethyl, naphthylethyl, and the like.

The hydroxyalkyl included in the substituents preferably refers to the straight or branched $C_{1-6}$ alkyl mentioned above having a hydroxyl group. Examples thereof include hydroxymethyl, hydroxyethyl, and the like.

The alkenyl included in the substituents preferably refers to a $C_{2-6}$ alkenyl group containing a carbon-carbon double bond. Examples thereof include vinyl, allyl, methylvinyl, propenyl, butenyl, pentenyl, hexenyl, and the like.

The alkynyl included in the substituents preferably refers to a $C_{2-6}$ alkynyl group containing a carbon-carbon triple bond. Examples thereof include ethynyl, propargyl, and the like.

The alkoxy or halogenoalkoxy included in the substituents preferably refers to a straight or branched $C_{1-6}$ alkoxy group or such a straight or branched $C_{1-6}$ alkoxy group that is substituted with the halogen mentioned above. Examples thereof include methoxy, ethoxy, n-propoxy, isopropoxy, 1-methylpropoxy, n-butoxy, isobutoxy, tert-butoxy, 2-methylbutoxy, neopentyloxy, pentan-2-yloxy, fluoromethoxy, difluoromethoxy, trifluoromethoxy, 1,1-difluoroethoxy, 2,2-difluoroethoxy, 2,2,2-trifluoroethoxy, 1,1,2,2-tetrafluoroethoxy, perfluoroethoxy, 3-fluoro-2-(fluoromethyl)-propoxy, 1,3-difluoropropan-2-yloxy, 2,2,3,3,3-pentafluoro-1-propoxy, and the like. The cycloalkoxy included in the substituents preferably refers to a $C_{3-7}$ cycloalkoxy group. Examples thereof include cyclopropoxy, cyclobutoxy, cyclopenthyloxy, cyclohexyloxy, cycloheptyloxy, and the like.

The alkoxy-alkyl included in the substituents preferably refers to the $C_{1-6}$ alkyl mentioned above that is substituted with the straight or branched $C_{1-6}$ alkoxy mentioned above. Examples thereof include methoxymethyl, ethoxymethyl, and the like.

The cycloalkyl-alkoxy included in the substituents preferably refers to a $C_{1-6}$ alkoxy group that is substituted with a $C_{3-7}$ cycloalkyl group. Examples thereof include cyclopropylmethoxy, cyclopropylethoxy, cyclobutylmethoxy, cyclopentylmethoxy, cyclohexylmethoxy, and the like.

The aralkyloxy included in the substituents preferably refers to an oxy group that has the aralkyl mentioned above. Examples thereof include benzyloxy, phenethyloxy, phenylpropyloxy, naphthylmethyloxy, naphthylethyloxy, and the like.

The aralkyloxy-alkyl included in the substituents preferably refers to the straight or branched $C_{1-6}$ alkyl mentioned above that has the aralkyloxy mentioned above. Examples thereof include benzyloxymethyl, benzyloxyethyl, and the like.

The alkylthio included in the substituents preferably refers to a $(C_{1-6})$ alkylthio group representing a straight or branched $C_{1-6}$ alkylthio group. Examples thereof include methylthio, ethylthio, n-propylthio, isopropylthio, n-butylthio, isobutylthio, sec-butylthio, tert-butylthio, pentylthio, hexylthio, and the like.

The cycloalkyl-alkylthio included in the substituents preferably refers to a $C_{1-6}$ alkylthio group that is substituted with a $C_{3-7}$ cycloalkyl group. Examples thereof include cyclopropylmethylthio, cyclopropylethylthio, cyclobutylmethylthio, cyclopentylmethylthio, cyclohexylmethylthio, and the like.

The mono- or dialkylamino included in the substituents refers to a mono- or di($C_{1-6}$ alkyl)amino group representing an amino group that is mono- or disubstituted with the straight or branched $C_{1-6}$ alkyl mentioned above. Examples thereof include methylamino, dimethylamino, ethylamino, diethylamino, methylethylamino, and the like.

The cycloalkyl-alkylamino included in the substituents refers to an alkylamino group that is substituted with the cycloalkyl mentioned above. Examples thereof include cyclopropylmethylamino, cyclobutylmethylamino, cyclopentylmethylamino, and the like.

Examples of the acyl included in the substituents include straight or branched $C_{1-6}$ acyl groups, such as formyl, acetyl, propionyl, n-butyryl, isobutyryl, valeryl, isovaleryl, and pivaloyl; benzoyl; and the like.

Examples of the acyloxy included in the substituents include straight or branched $C_{1-6}$ acyloxy groups, such as formyloxy, acetoxy, propionyloxy, n-butyryloxy, isobutyryloxy, valeryloxy, isovaleryloxy, and pivaloyloxy; benzoyloxy; amino acid-derived acyloxy groups, such as glycyloxy, alanyloxy, and leucyloxy; and the like The alkoxycarbonyl included in the substituents refers to, for example, a carbonyl group that is substituted with the alkoxy mentioned above. Examples thereof include methoxycarbonyl, ethoxycarbonyl, n-propoxycarbonyl, isopropoxycarbonyl, 1-methylpropoxycarbonyl, n-butoxycarbonyl, isobutoxycarbonyl, tert-butoxycarbonyl, 2-methylbutoxycarbonyl, neopentyloxycarbonyl, pentan-2-yloxycarbonyl, and the like.

The aralkyloxycarbonyl included in the substituents preferably refers to a carbonyl group that is substituted with the aralkyloxy mentioned above. Examples thereof include benzyloxycarbonyl, phenethyloxycarbonyl, phenylpropyloxycarbonyl, naphthylmethyloxycarbonyl, naphthylethyloxycarbonyl, and the like.

Examples of the carbamoyl included in the substituents include —$CONH_2$, (mono- or dialkyl)carbamoyl, (mono- or diaryl)carbamoyl, (N-alkyl-N-aryl)carbamoyl, pyrrolidinocarbamoyl, piperidinocarbamoyl, piperazinocarbamoyl, morpholinocarbamoyl, and the like.

The saturated or unsaturated heterocyclic group included in the substituents preferably refers to a monocyclic or bicyclic saturated or 5- to 10-membered unsaturated heterocyclic group having preferably 1 to 4 heteroatoms selected from N, S, and O. Examples thereof include pyrrolidinyl, piperidinyl, piperazinyl, hexamethyleneimino, morpholino, thiomorpholino, homopiperazinyl, tetrahydrofuranyl, tetrahydropyranyl, imidazolyl, thienyl, furyl, pyrrolyl, oxazolyl, isoxazolyl, thiazolyl, isothiazolyl, pyrazolyl, triazolyl, tetrazolyl, pyridyl, pyrazyl, pyrimidinyl, pyridazinyl, indolyl, isoindolyl, indazolyl, methylenedioxyphenyl, ethylenedioxyphenyl, benzofuranyl, dihydrobenzofuranyl, benzoimidazolyl, benzoxazolyl, benzothiazolyl, purinyl, quinolyl, isoquinolyl, quinazolinyl, quinoxalyl, and the like.

The aromatic hydrocarbon included in the substituents preferably refers to a $C_{6-14}$ aromatic hydrocarbon group. Examples thereof include phenyl, naphthyl, and the like.

The saturated heterocyclic oxy group included in the substituents refers to an oxy group that has a 5- to 7-membered monocyclic saturated heterocyclic group having one or two heteroatoms selected from N, S, and O, such as pyrrolidinyl, piperidinyl, piperazinyl, hexamethyleneimino, morpholino, thiomorpholino, and homopiperazinyl. Examples thereof include tetrahydrofuranyloxy, tetrahydropyranyloxy, and the like.

In Formula (a), $X^{a1}$ represents CH or N. Further, in the formula, one of $X^{a2}$, $X^{a3}$, and $X^{a4}$ represents N, and the others each represent CH. Based on these definitions of $X^{a1}$ to $X^{a4}$, examples of the azabicyclo skeleton in Formula (a) include the following structural formulas:

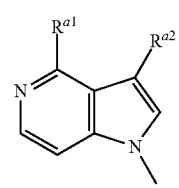

(A-1a)

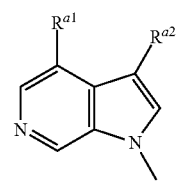

(A-2a)

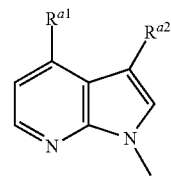

(A-3a)

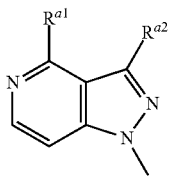

(A-4a)

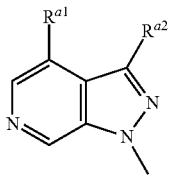

(A-5a)

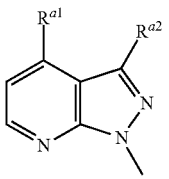

(A-6a)

wherein $R^{a1}$ and $R^{a2}$ are as defined above.

Of these skeletons, (A-3a) and (A-6a) are particularly preferable.

In Formula (a), the "monocyclic or bicyclic unsaturated heterocyclic group having 1 to 4 heteroatoms selected from N, S, and O" in the "optionally substituted monocyclic or bicyclic unsaturated heterocyclic group having 1 to 4 heteroatoms selected from N, S, and O," represented by $R^{a1}$ is preferably a monocyclic or bicyclic 5- to 10-membered unsaturated heterocyclic group having 1 to 3 heteroatoms selected from N, S and O, and more preferably a monocyclic 5- to 6-membered unsaturated heterocyclic group having 1 to 3 heteroatoms selected from N, S and O, or a bicyclic 9- to 10-membered unsaturated heterocyclic group having 1 to 3 heteroatoms selected from N, S, and O. The heterocyclic group is preferably a group having imidazole, pyrazole, thiophene, furan, pyrrole, oxazole, isoxazole, thiazole, isothiazole, triazole, tetrazole, pyridine, pyrazine, pyrimidine, pyridazine, indole, isoindole, pyrrolopyridine, indazole, methylenedioxyphenyl, ethylenedioxyphenyl, benzofuran, dihydrobenzofuran, benzimidazole, benzoxazole, benzothiazole, purine, quinoline, tetrahydroquinoline, isoquinoline, quinazoline or quinoxaline. The heterocyclic group is more preferably a group having imidazole, pyrazole, thiophene, furan, pyridine, indole, pyrrolopyridine, benzofuran, quinoline, or tetrahydroquinoline, and particularly preferably a group having imidazole, pyridine or quinoline.

Specific examples include 1H-imidazol-1-yl, 1H-imidazol-2-yl, 1H-imidazol-4-yl, 1H-pyrazol-1-yl, 1H-pyrazol-3-yl, 1H-pyrazol-4-yl, thiophen-2-yl, thiophen-3-yl, furan-2-yl, furan-3-yl, pyrrol-1-yl, pyrrol-2-yl, pyrrol-3-yl, oxazol-2-yl, oxazol-4-yl, oxazol-5-yl, isoxazol-3-yl, isoxazol-4-yl, isoxazol-5-yl, thiazol-2-yl, thiazol-3-yl, thiazol-4-yl, thiazol-5-yl, isothiazol-2-yl, isothiazol-4-yl, isothiazol-5-yl, pyrazol-1-yl, pyrazol-3-yl, pyrazol-4-yl, 1,2,3-triazol-1-yl, 1,2,3-triazol-4-yl, 1,2,4-triazol-1-yl, 1,2,4-triazol-3-yl, 1,2,4-triazol-4-yl, tetrazol-1-yl, tetrazol-5-yl, pyridin-2-yl, pyridin-3-yl, pyridin-4-yl, pyrazin-2-yl, pyrazin-3-yl, pyrimidin-2-yl, pyrimidin-4-yl, pyrimidin-5-yl, pyrimidin-6-yl, pyridazin-3-yl, pyridazin-4-yl, indol-1-yl, indol-2-yl, indol-3-yl, indol-4-yl, indol-5-yl, indol-6-yl, indol-7-yl, isoindol-1-yl, isoindol-2-yl, isoindol-4-yl, isoindol-5-yl, 1H-pyrrolo[2,3-b]pyridin-1-yl, 1H-pyrrolo[2,3-b]pyridin-2-yl, 1H-pyrrolo[2,3-b]pyridin-3-yl, 1H-pyrrolo[2,3-b]pyridin-4-yl, 1H-pyrrolo[2,3-b]pyridin-5-yl, 1H-pyrrolo[2,3-b]pyridin-6-yl, 1H-indazol-1-yl, 1H-indazol-3-yl, 1H-indazol-4-yl, 1H-indazol-5-yl, 1H-indazol-6-yl, 1H-indazol-7-yl, methylenedioxyphenyl, ethylenedioxyphenyl, benzofuran-2-yl, benzofuran-3-yl, benzofuran-4-yl, benzofuran-5-yl, benzofuran-6-yl, benzofuran-7-yl, 2,3-dihydrobenzofuran-2-yl, 2,3-dihydrobenzofuran-3-yl, benzimidazol-1-yl, benzimidazol-2-yl, benzimidazol-4-yl, benzimidazol-5-yl, benzoxazol-2-yl, benzoxazol-4-yl, benzoxazol-5-yl, benzothiazol-2-yl, benzothiazol-4-yl, benzothiazol-5-yl, purin-2-yl, purin-6-yl, purin-7-yl, purin-8-yl, quinolin-2-yl, quinolin-3-yl, quinolin-4-yl, quinolin-5-yl, quinolin-6-yl, quinolin-7-yl, quinolin-8-yl, 5,6,7,8-tetrahydroquinolin-2-yl, 5,6,7,8-tetrahydroquinolin-3-yl, 5,6,7,8-tetrahydroquinolin-4-yl, isoquinolin-1-yl, isoquinolin-3-yl, isoquinolin-4-yl, isoquinolin-5-yl, isoquinolin-6-yl, isoquinolin-7-yl, isoquinolin-8-yl, quinazolin-4-yl, quinoxalin-2-yl, quinoxalin-5-yl, quinoxalin-6-yl, and the like. The heterocyclic group is preferably 1H-imidazol-1-yl, pyrazol-4-yl, thiophen-3-yl, furan-2-yl, pyridin-3-yl, pyridin-4-yl, indol-5-yl, 1H-pyrrolo[2,3-b]pyridin-5-yl, benzofuran-2-yl, quinolin-3-yl, or 5,6,7,8-tetrahydroquinolin-3-yl, more preferably 1H-imidazol-1-yl, pyridin-3-yl, pyridin-4-yl, indol-5-yl, 1H-pyrrolo[2,3-b]pyridin-5-yl, benzofuran-2-yl, quinolin-3-yl, or 5,6,7,8-tetrahydroquinolin-3-yl, and particularly preferably 1H-imidazol-1-yl, pyridin-3-yl, or quinolin-3-yl.

In Formula (a), examples of substituents for the unsaturated heterocyclic group represented by $R^{a1}$ include the substituents mentioned above. The substituent is preferably selected from alkyl, alkoxy, alkoxy-alkyl, aralkyl, aralkyloxy-alkyl, halogen, halogenoalkyl, acyl, optionally substituted saturated or unsaturated heterocyclic group, and optionally substituted aromatic hydrocarbon. The number of substituents is 1 to 3. The substituent is more preferably selected from alkyl; alkoxy; unsaturated heterocyclic groups optionally having alkyl, halogenoalkyl, aralkyl or hydroxyalkyl; and an aromatic hydrocarbon group optionally having alkyl, alkoxy, or carbamoyl. The number of substituents is 1 to 3. Examples of unsaturated heterocyclic groups that may be substituted on the unsaturated heterocyclic ring represented by $R^{a1}$ include pyrazole, imidazole, pyridine, pyrimidine, furan, thiophene, and the like. Examples of aromatic hydrocarbon include phenyl and naphthyl.

Specific examples of substituents for the unsaturated heterocyclic group represented by $R^{a1}$ include methyl, ethyl, n-propyl, isopropyl, n-butyl, isobutyl, sec-butyl, tert-butyl, methoxy, ethoxy, n-propoxy, isopropoxy, 1-methylpropoxy, n-butoxy, isobutoxy, tert-butoxy, 1H-pyrazol-4-yl, 1-methyl-1H-pyrazol-4-yl, 1-ethyl-1H-pyrazol-4-yl, 1-isopropyl-1H-pyrazol-4-yl, 1-benzyl-1H-pyrazol-4-yl, 1-(difluoromethyl)-1H-pyrazol-4-yl, 1-(hydroxyethyl)-1H-pyrazol-4-yl, 1H-imidazol-1-yl, pyridin-3-yl, pyridin-4-yl, pyrimidine-5-yl, furan-2-yl, furan-3-yl, thiophen-3-yl, phenyl, 4-methoxyphenyl, 4-carbamoylphenyl, 4-isopropylcarbamoylphenyl, 4-dimethylcarbamoylphenyl, and the like.

Specific examples of preferable $R^{a1}$ include 1H-imidazol-1-yl, 4-phenyl-1H-imidazol-1-yl, 4-(4-carbamoylphenyl)-1H-imidazol-1-yl, 4-(4-methoxyphenyl)-1H-imidazol-1-yl, 4-(thiophen-3-yl)-1H-imidazol-1-yl, 4-(pyridin-3-yl)-1H-imidazol-1-yl, 4-(pyridin-4-yl)-1H-imidazol-1-yl, 5-methyl-4-(pyridin-3-yl)-1H-imidazol-1-yl, 4-(pyrimidin-5-yl)-1H-imidazol-1-yl, 4-(furan-2-yl)-1H-imidazol-1-yl, 4-(furan-3-yl)-1H-imidazol-1-yl, 4-(1H-pyrazol-4-yl)-1H-imidazol-1-yl, 4-(1-methyl-1H-pyrazol-4-yl)-1H-imidazol-1-yl, 4-(1-ethyl-1H-pyrazol-4-yl)-1H-imidazol-1-yl, 4-(1-isopropyl- 1H-pyrazol-4-yl)-1H-imidazol-1-yl, 4-(1-hydroxymethyl)-(1H-pyrazol-4-yl)-1H-imidazol-1-yl, 4-(1-(difluoromethyl)-1H-pyrazol-4-yl)-1H-imidazol-1-yl, 4-(1-(hydroxyethyl)-1H-pyrazol-4-yl)-1H-imidazol-1-yl, 4-(1-(hydroxymethyl)-1H-pyrazol-4-yl)-1H-imidazol-1-yl, 4-(1-benzyl-1H-pyrazol-4-yl)-1H-imidazol-1-yl, 4-(1-(benzyloxyethyl)-1H-pyrazol-4-yl)-1H-imidazol-1-yl, 1'H-1,4'-biimidazol-1'-yl, pyridin-3-yl, pyridin-4-yl, 5-methoxypyridin-3-yl, 6-methoxypyridin-3-yl, 1-benzyl-1H-pyrazol-4-yl, 1-methyl-1H-indol-5-yl, 1H-pyrrolo[2,3-b]pyridin-5-yl, 1-methyl-1H-pyrrolo[2,3-b]pyridin-5-yl, 1-methoxymethyl-1H-pyrrolo[2,3-b]pyridin-5-yl, 5,6,7,8-tetrahydroquinolin-3-yl, quinolin-3-yl, thiophen-3-yl, furan-2-yl, and benzofuran-2-yl. $R^{a1}$ is more preferably 1H-imidazol-1-yl, 4-(pyridin-3-yl)-1H-imidazol-1-yl, 4-(pyridin-4-yl)-1H-imidazol-1-yl, 4-(1H-pyrazol-4-yl)-1H-imidazol-1-yl, 4-(1-methyl-1H-pyrazol-4-yl)-1H-imidazol-1-yl, 4-(1-ethyl-1H-pyrazol-4-yl)-1H-imidazol-1-yl, 4-(1-isopropyl-1H-pyrazol-4-yl)-1H-imidazol-1-yl, 4-(1-benzyl-1H-pyrazol-4-yl)-1H-imidazol-1-yl, quinolin-3-yl, or 4-(1H-pyrazol-4-yl)-1H-imidazol-1-yl, and particularly preferably 4-(1-methyl-1H-pyrazol-4-yl)-1H-imidazol-1-yl, 4-(pyridin-3-yl)-1H-imidazol-1-yl, or quinolin-3-yl.

In Formula (a), the "$C_{1-6}$ alkyl" in the "optionally substituted $C_{1-6}$ alkyl" represented by $R^2$ refers to a straight or branched $C_{1-6}$ alkyl group, such as methyl, ethyl, n-propyl, isopropyl, n-butyl, isobutyl, sec-butyl, tert-butyl, pentyl, and hexyl, and is preferably methyl, ethyl, n-propyl, or isopropyl.

Examples of substituents for the "optionally substituted $C_{1-6}$ alkyl" represented by $R^2$ include the substituents mentioned above. Of these, the substituent is preferably halogen.

The halogen-substituted alkyl group is preferably $C_{1-6}$ halogenoalkyl, and more preferably trifluoromethyl.

The "$C_{2-6}$ alkenyl" represented by $R^{a2}$ refers to the $C_{2-6}$ alkenyl mentioned above, and is preferably vinyl. Examples of substituents for the alkenyl include the substituents mentioned above.

$R^{a2}$ is more preferably optionally substituted $C_{1-6}$ alkyl or optionally substituted $C_{2-6}$ alkenyl, even more preferably $C_{1-6}$ alkyl optionally having halogen or $C_{2-6}$ alkenyl optionally having halogen, and particularly preferably $C_{1-4}$ alkyl optionally having halogen.

One or two of $Y^{a1}$, $Y^{a2}$, $Y^{a3}$ and $Y^{a4}$ represent C—$R^{a4}$, and the others are identical or different and each represents CH or N. Of these, it is preferable that one or two of $Y^{a1}$, $Y^{a2}$, $Y^{a3}$, and $Y^{a4}$ represent C—$R^{a4}$, and the others each represent CH. It is more preferable that $Y^{a1}$ and $Y^{a3}$ each represent CH, and one or two of $Y^{a2}$ and $Y^{a4}$ represent C—$R^{a4}$, and the other represents CH. These preferable embodiments are represented by the following structural formulas:

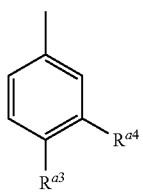

(B-1a)

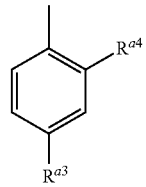

(B-2a)

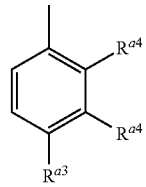

(B-3a)

wherein $R^{a3}$ and $R^{a4}$ are as defined above.

Of the above, (B-1a) and (B-2a) are particularly preferable.

In Formula (a), $R^{a3}$ represents cyano or —CO—$R^{a5}$. Of these, —CO—$R^{a5}$ is particularly preferable.

In Formula (a), $R^{a4}$s are identical or different and each represents hydrogen, halogen, cyano, optionally substituted $C_{1-6}$ alkyl, $C_{3-7}$ cycloalkyl, $C_{2-6}$ alkenyl, $C_{1-6}$ alkoxy, aromatic hydrocarbon, —N($R^{a6}$)($R^{a7}$), —S$R^{a8}$, or —CO—$R^{a9}$. Of these, each $R^{a4}$ preferably represents halogen; $C_{1-6}$ alkyl optionally having mono- or di($C_{1-6}$ alkyl)amino or a monocyclic 5- to 7-membered saturated heterocyclic group having 1 or 2 heteroatoms selected from N, S and O; $C_{1-6}$ alkoxy; —N($R^{a6}$)($R^{a7}$); —S$R^{a8}$; or —CO—$R^{a9}$, and more preferably halogen, $C_{1-6}$ alkyl, or —N($R^{a6}$)($R^{a7}$).

In Formula (a), the "halogen" represented by $R^{a4}$ refers to the halogen mentioned above, and is preferably chlorine.

In Formula (a), the "$C_{1-6}$ alkyl" in the "optionally substituted $C_{1-6}$ alkyl" represented by $R^{a4}$ refers to the $C_{1-6}$ alkyl mentioned above and is preferably methyl, ethyl, n-propyl, or isopropyl. Examples of substituents for "optionally substituted $C_{1-6}$ alkyl" represented by $R^{a4}$ include the substituents mentioned above. The substituent is preferably a mono- or di($C_{1-6}$ alkyl)amino group (e.g., ethylamino and dimethylamino) or a monocyclic 5- to 7-membered saturated heterocyclic group having 1 or 2 heteroatoms selected from N, S, and O (e.g., pyrrolidyl and morpholino).

In Formula (a), the "$C_{3-7}$ cycloalkyl" represented by $R^{a4}$ refers to the $C_{3-7}$ cycloalkyl mentioned above, and is preferably cyclopropyl.

In Formula (a), the "$C_{2-6}$ alkenyl" represented by $R^{a4}$ refers to the $C_{2-6}$ alkenyl mentioned above, and is preferably vinyl or prop-1-en-2-yl.

In Formula (a), the "$C_{1-6}$ alkoxy" represented by $R^{a4}$ refers to the $C_{1-6}$ alkoxy mentioned above, and is preferably methoxy.

In Formula (a), the "mono- or dialkylamino" in the "optionally substituted mono- or dialkylamino" represented by $R^{a5}$ refers to the mono- or dialkylamino mentioned above, and is preferably mono- or di($C_{1-6}$ alkyl)amino. Examples of substituents for the "optionally substituted mono- or dialkylamino" represented by $R^{a5}$ include the substituents mentioned above.

$R^{a5}$ is more preferably amino, hydroxylamino, or mono- or di($C_{1-6}$ alkyl)amino, and particularly preferably amino.

In Formula (a), the "$C_{1-6}$ alkyl" in the "optionally substituted $C_{1-6}$ alkyl" represented by $R^{a6}$ or $R^{a7}$ refers to the $C_{1-6}$ alkyl mentioned above and is preferably ethyl, n-propyl, n-butyl, isobutyl, sec-butyl, or pentyl. Examples of substituents for the "optionally substituted $C_{1-6}$ alkyl" represented by $R^{a6}$ or $R^{a7}$ include the substituents mentioned above. The substituent is preferably hydroxyl, $C_{3-7}$ cycloalkyl (e.g., cyclohexyl), saturated heterocyclic groups (e.g., pyrrolidyl and morpholino), unsaturated heterocyclic groups (e.g., pyridyl), mono- or di($C_{1-6}$ alkyl)amino (e.g., ethylamino and dimethylamino), ($C_{1-6}$ alkyl)thio (e.g., methylthio), or $C_{1-6}$ alkoxy optionally having hydroxyl.

In Formula (a), the "$C_{1-6}$ halogenoalkyl" represented by $R^{a6}$ or $R^{a7}$ refers to the $C_{1-6}$ halogenoalkyl mentioned above, and is preferably 2,2-difluoroethyl or 2,2,2-trifluoroethyl.

In Formula (a), examples of the "$C_{3-7}$ cycloalkyl" in the "optionally substituted $C_{3-7}$ cycloalkyl" represented by $R^{a6}$ or $R^{a7}$ include cyclopropyl, cyclobutyl, cyclopentyl, cyclohexyl, and cycloheptyl. The $C_{3-7}$ cycloalkyl is preferably cyclopropyl, cyclopentyl, or cyclohexyl. Examples of substituents for the "optionally substituted $C_{3-7}$ cycloalkyl" represented by $R^{a6}$ or $R^{a7}$ include the substituents mentioned above. The substituent is preferably hydroxyl, amino, amino acid-derived acyloxy, alkanoylamino, alkylsulfonylamino, or the like.

In Formula (a), the "aralkyl" in the "optionally substituted aralkyl" represented by $R^{a6}$ or $R^{a7}$ refers to the aralkyl mentioned above and is preferably $C_{7-12}$ aralkyl, specifically benzyl. Examples of substituents for the "optionally substituted aralkyl" represented by $R^{a6}$ or $R^{a7}$ include the substituents mentioned above. Specific examples of the substituents include saturated heterocyclic groups such as pyrrolidinyl.

In Formula (a), the "aromatic hydrocarbon" in the "optionally substituted aromatic hydrocarbon" represented by $R^{a6}$ or $R^{a7}$ refers to the $C_{6-14}$ aromatic hydrocarbon mentioned above, and is preferably phenyl. Examples of substituents in the "optionally substituted aromatic hydrocarbon" represented by $R^{a6}$ or $R^{a7}$ include the substituents mentioned above. The substituent is preferably halogen, alkylthio (e.g., methylthio), saturated heterocyclic groups (e.g., morpholino), or substituted carbamoyl (e.g., pyrrolidine-carbonyl).

In Formula (a), the "saturated heterocyclic group" in the "optionally substituted saturated heterocyclic group" represented by $R^{a6}$ or $R^{a7}$ refers to the saturated heterocyclic group mentioned above, and is preferably piperidinyl or tetrahydropyranyl. Examples of substituents for the "optionally substituted saturated heterocyclic group" represented by $R^{a6}$ or $R^{a7}$ include the substituents mentioned above. The substituent is preferably $C_{1-6}$ alkyl (e.g., methyl), acyl (e.g., acetyl), carbonyl having a saturated heterocyclic group (e.g., 2,6-dihydroxypyrimidinyl-4-carbonyl), or aminoalkylcarbonyl (e.g., 2-aminoacetyl).

In Formula (a), the "unsaturated heterocyclic group" in the "optionally substituted unsaturated heterocyclic group" represented by $R^{a6}$ or $R^{a7}$ refers to the unsaturated heterocyclic group mentioned above, and is preferably pyridyl or oxazolyl. Examples of substituents for the "optionally substituted unsaturated heterocyclic group" represented by $R^{a6}$ or $R^{a7}$ include the substituents mentioned above.

In Formula (a), the "saturated heterocyclic group" that is optionally formed by $R^{a6}$ and $R^{a7}$ together with the nitrogen to which they are attached refers to a monocyclic or bicyclic saturated heterocyclic group preferably having 1 to 4 atoms selected from oxygen, nitrogen, and sulfur. Examples thereof include pyrrolidinyl, piperidinyl, piperazinyl, hexamethyleneimino, morpholino, thiomorpholino, homopiperazinyl, tetrahydrofuranyl, and tetrahydropyranyl.

In Formula (a), a preferable combination of $R^{a6}$ and $R^{a7}$ is such that $R^{a6}$ represents hydrogen or optionally substituted $C_{1-6}$ alkyl, and $R^{a7}$ represents hydrogen, optionally substituted $C_{1-6}$ alkyl, optionally substituted $C_{3-7}$ cycloalkyl, optionally substituted $C_{7-12}$ aralkyl, optionally substituted $C_{6-14}$ aromatic hydrocarbon, an optionally substituted monocyclic or bicyclic saturated heterocyclic group having 1 to 4 heteroatoms selected from N, S, and O, or an optionally substituted monocyclic or bicyclic unsaturated heterocyclic group having 1 to 4 heteroatoms selected from N, S and O, or such that $R^{a6}$ and $R^{a7}$, taken together with the nitrogen to which they are attached, form a 5- to 7-membered saturated heterocyclic group. A more preferable combination is such that $R^{a6}$ represents hydrogen, and $R^{a7}$ represents hydrogen, optionally substituted $C_{1-6}$ alkyl, optionally substituted $C_{3-7}$ cycloalkyl, or an optionally substituted $C_{1-4}$ monocyclic or bicyclic saturated heterocyclic group having 1 to 4 heteroatoms selected from N, S, and O. A particularly preferable combination is such that $R^{a6}$ represents hydrogen, and $R^{a7}$ represents optionally substituted $C_{1-6}$ alkyl or optionally substituted $C_{3-7}$ cycloalkyl.

In Formula (a), the "$C_{3-7}$ cycloalkyl" in the "optionally substituted $C_{3-7}$ cycloalkyl" represented by $R^{a8}$ refers to the $C_{3-7}$ cycloalkyl mentioned above, and is preferably cyclohexyl. Examples of substituents for the "optionally substituted $C_{3-7}$ cycloalkyl" represented by $R^{a8}$ include the substituents mentioned above, with hydroxyl being preferable.

In Formula (a), the "aromatic hydrocarbon" in the "optionally substituted aromatic hydrocarbon" represented by $R^{a8}$ refers to the $C_{6-14}$ aromatic hydrocarbon mentioned above, and is preferably phenyl. Examples of substituents in the "optionally substituted aromatic hydrocarbon" represented by $R^{a8}$ include the substituents mentioned above, with hydroxyl being preferable.

$R^{a8}$ is preferably optionally substituted $C_{3-7}$ cycloalkyl or optionally substituted $C_{6-14}$ aromatic hydrocarbon. In Formula (a), the "mono- or dialkylamino" in the "optionally substituted mono- or dialkylamino" represented by $R^{a9}$ refers to the mono- or dialkylamino mentioned above, and is preferably mono- or di($C_{1-6}$ alkyl)amino. Examples of substituents for the "optionally substituted mono- or dialkylamino" represented by $R^{a9}$ include the substituents mentioned above.

$R^{a9}$ is preferably hydrogen, hydroxyl, amino, or mono- or di($C_{1-6}$ alkyl)amino, and particularly preferably hydrogen.

The compound of the present invention is preferably a compound represented by Formula (a) or a salt thereof wherein $X^{a1}$ represents CH or N;

one of $X^{a2}$, $X^{a3}$ and $X^{a4}$ represents N, and the others each represent CH;

one or two of $Y^{a1}$, $Y^{a2}$, $Y^{a3}$, and $Y^{a4}$ represent C—$R^{a4}$, and the others are identical or different and each represents CH or N;

$R^{a1}$ represents an optionally substituted monocyclic or bicyclic unsaturated heterocyclic group having 1 to 4 heteroatoms selected from N, S, and O;

$R^{a2}$ represents $C_{1-6}$ alkyl optionally having halogen or $C_{2-6}$ alkenyl;

$R^{a3}$ represents —CO—$R^{a5}$;

$R^{a4}$s are identical or different and each represents hydrogen, halogen, cyano, optionally substituted $C_{1-6}$ alkyl, $C_{2-6}$ alkenyl, $C_{1-6}$ alkoxy, aromatic hydrocarbon, —N($R^{a6}$)($R^{a7}$), —S—$R^{a8}$, or —CO—$R^{a9}$;

$R^{a5}$ represents amino or mono- or di($C_{1-6}$ alkyl)amino;

$R^{a6}$ and $R^{a7}$ are identical or different and each represent hydrogen, optionally substituted $C_{1-6}$ alkyl, $C_{1-6}$ halogenoalkyl, optionally substituted $C_{3-7}$ cycloalkyl, optionally substituted aralkyl, optionally substituted aromatic hydrocarbon, an optionally substituted saturated heterocyclic group, or an optionally substituted unsaturated heterocyclic group, or $R^{a6}$ and $R^{a7}$, taken together with the nitrogen to which they are attached, form a saturated heterocyclic group;

$R^{a8}$ represents optionally substituted $C_{3-7}$ cycloalkyl or optionally substituted aromatic hydrocarbon; and $R^{a9}$ represents hydrogen, hydroxyl, amino optionally having hydroxyl, or optionally substituted mono- or dialkylamino.

The compound of the present invention is more preferably a compound represented by Formula (a) or a salt thereof wherein $X^{a1}$ represents CH or N;

one of $X^{a2}$, $X^{a3}$, and $X^{a4}$ represents N, and the others each represent CH;

one or two of $Y^{a1}$, $Y^{a2}$, $Y^{a3}$, and $Y^{a4}$ represent C—$R^{a4}$, and the others are identical or different and each represents CH or N;

$R^{a1}$ represents an optionally substituted monocyclic 5- to 6-membered unsaturated heterocyclic group having 1 to 3 heteroatoms selected from N, S, and O, or an optionally substituted bicyclic 9- to 10-membered unsaturated heterocyclic group having 1 to 3 heteroatoms selected from N, S, and O;

$R^{a2}$ represents $C_{1-6}$ alkyl optionally having halogen or $C_{2-6}$ alkenyl;

$R^{a3}$ represents —CO—$R^{a5}$;

$R^{a4}$s are identical or different and each represents hydrogen, halogen, cyano, optionally substituted $C_{1-6}$ alkyl, $C_{2-6}$ alkenyl, $C_{1-6}$ alkoxy, aromatic hydrocarbon, —N($R^{a6}$)($R^{a7}$), —S—$R^{a8}$, or —CO—$R^{a9}$;

$R^{a5}$ is amino, or mono- or di($C_{1-6}$ alkyl)amino;

$R^{a6}$ and $R^{a7}$ are identical or different and each represents hydrogen, optionally substituted $C_{1-6}$ alkyl, $C_{1-6}$ halogenoalkyl, optionally substituted $C_{3-7}$ cycloalkyl, optionally substituted aralkyl, optionally substituted aromatic hydrocarbon, an optionally substituted saturated heterocyclic group, or an optionally substituted unsaturated heterocyclic group, or $R^{a6}$ and $R^{a7}$, taken together with the nitrogen to which they are attached, form a saturated heterocyclic group;

$R^{a8}$ represents optionally substituted $C_{3-7}$ cycloalkyl or optionally substituted aromatic hydrocarbon; and $R^{a9}$ represents hydrogen, hydroxyl, amino optionally having hydroxyl, or optionally substituted mono- or dialkylamino.

The compound of the present invention is even more preferably a compound represented by Formula (a) or a salt thereof wherein $X^{a1}$ represents CH or N;

$X^{a2}$ represents N, and $X^{a3}$ and $X^{a4}$ each represent CH;

one or two of $Y^{a1}$, $Y^{a2}$, $Y^{a3}$, and $Y^{a4}$ represent C—$R^{a4}$, and the others are identical or different and each represents CH or N;

$R^{a1}$ represents an optionally substituted monocyclic 5- to 6-membered unsaturated heterocyclic group having 1 to 3 heteroatoms selected from N, S, and O, or an optionally substituted bicyclic 9- to 10-membered unsaturated heterocyclic group having 1 to 3 heteroatoms selected from N, S, and O;

$R^{a2}$ represents $C_{1-6}$ alkyl optionally having halogen or $C_{2-6}$ alkenyl;

$R^{a3}$ represents —CO—$R^{a5}$;

$R^{a4}$s are identical or different and each represents hydrogen, halogen, cyano, optionally substituted $C_{1-6}$ alkyl, $C_{2-6}$ alkenyl, $C_{1-6}$ alkoxy, aromatic hydrocarbon, —N($R^{a6}$)($R^{a7}$), —S—$R^{a8}$, or —CO—$R^{a9}$;

$R^{a5}$ is amino, or mono- or di($C_{1-6}$ alkyl)amino;

$R^{a6}$ and $R^{a7}$ are identical or different and each represents hydrogen, optionally substituted $C_{1-6}$ alkyl, $C_{1-6}$ halogenoalkyl, optionally substituted $C_{3-7}$ cycloalkyl, optionally substituted aralkyl, optionally substituted aromatic hydrocarbon, an optionally substituted saturated heterocyclic group, or an optionally substituted unsaturated heterocyclic group, or $R^{a6}$ and $R^{a7}$, taken together with the nitrogen to which they are attached, form a saturated heterocyclic group;

$R^{a8}$ represents optionally substituted $C_{3-7}$ cycloalkyl or optionally substituted aromatic hydrocarbon; and $R^{a9}$ represents hydrogen, hydroxyl, amino optionally having hydroxyl, or optionally substituted mono- or dialkylamino.

The compound of the present invention is furthermore preferably a compound represented by Formula (a) or a salt thereof wherein $X^{a1}$ represents CH or N;

$X^{a2}$ represents N, and $X^{a3}$ and $X^{a4}$ each represent CH;

one or two of $Y^{a1}$, $Y^{a2}$, $Y^{a3}$, and $Y^{a4}$ represent C—$R^{a4}$, and the others are identical or different and each represents CH or N;

$R^{a1}$ represents optionally substituted 1H-imidazol-1-yl, optionally substituted pyrazol-4-yl, optionally substituted thiophen-3-yl, optionally substituted furan-2-yl, optionally substituted pyridin-3-yl, optionally substituted pyridin-4-yl, optionally substituted indol-5-yl, optionally substituted 1H-pyrrolo[2,3-b]pyridin-5-yl, optionally substituted benzofuran-2-yl, optionally substituted quinolin-3-yl, or optionally substituted 5,6,7,8-tetrahydroquinolin-3-yl;

$R^{a2}$ represents $C_{1-6}$ alkyl optionally having halogen or $C_{2-6}$ alkenyl;

$R^{a3}$ represents —CO—$R^{a5}$;

$R^{a4}$s are identical or different and each represents hydrogen, halogen, cyano, optionally substituted $C_{1-6}$ alkyl, $C_{2-6}$ alkenyl, $C_{1-6}$ alkoxy, aromatic hydrocarbon, —N($R^{a6}$)($R^{a7}$), —S—$R^{a8}$, or —CO—$R^{a9}$;

$R^{a5}$ represents amino, or mono- or di($C_{1-6}$ alkyl)amino;

$R^{a6}$ and $R^{a7}$ are identical or different and each represents hydrogen, optionally substituted $C_{1-6}$ alkyl, $C_{1-6}$ halogenoalkyl, optionally substituted $C_{3-7}$ cycloalkyl, optionally substituted aralkyl, optionally substituted aromatic hydrocarbon, an optionally substituted saturated heterocyclic group, or an optionally substituted unsaturated heterocyclic group, or $R^{a6}$ and $R^{a7}$, taken together with the nitrogen to which they are attached, form a saturated heterocyclic group;

$R^{a8}$ represents optionally substituted $C_{3-7}$ cycloalkyl or optionally substituted aromatic hydrocarbon; and $R^{a9}$ represents hydrogen, hydroxyl, amino optionally having hydroxyl, or optionally substituted mono- or dialkylamino.

The compound of the present invention is still more preferably a compound represented by Formula (a) or a salt thereof wherein $X^{a1}$ represents CH or N;

$X^{a2}$ represents N, and $X^{a3}$ and $X^{a4}$ each represent CH;

$Y^{a1}$ and $Y^{a3}$ each represent CH, one or two of $Y^2$ and $Y^{a4}$ represent C—$R^{a4}$, and the other represents CH;

$R^{a1}$ represents optionally substituted 1H-imidazol-1-yl, optionally substituted pyrazol-4-yl, optionally substituted thiophen-3-yl, optionally substituted furan-2-yl, optionally substituted pyridin-3-yl, optionally substituted pyridin-4-yl, optionally substituted indol-5-yl, optionally substituted 1H-pyrrolo[2,3-b]pyridin-5-yl, optionally substituted benzofuran-2-yl, optionally substituted quinolin-3-yl, or optionally substituted 5,6,7,8-tetrahydroquinolin-3-yl;

$R^{a2}$ represents $C_{1-6}$ alkyl optionally having halogen or $C_{2-6}$ alkenyl;

$R^{a3}$ represents —CO—$R^{a5}$;

$R^{a4}$ represents halogen, $C_{1-6}$ alkyl optionally having mono- or di($C_{1-6}$ alkyl)amino or a monocyclic 5- to 7-membered saturated heterocyclic group having one or two heteroatoms selected from N, S and O, $C_{1-6}$ alkoxy, —N($R^{a6}$)($R^{a7}$), —S$R^{a8}$, or —CO—$R^{a9}$;

$R^{a5}$ represents amino or mono- or di($C_{1-6}$ alkyl)amino;

$R^{a6}$ represents hydrogen or optionally substituted $C_{1-6}$ alkyl, and $R^{a7}$ represents hydrogen, optionally substituted $C_{1-6}$ alkyl, optionally substituted $C_{3-7}$ cycloalkyl, optionally substituted $C_{7-12}$ aralkyl, optionally substituted $C_{6-14}$ aromatic hydrocarbon, an optionally substituted monocyclic or bicyclic saturated heterocyclic group having 1 to 4 heteroatoms selected from N, S, and O, or an optionally substituted monocyclic or bicyclic unsaturated heterocyclic group having 1 to 4 heteroatoms selected from N, S, and O, or $R^{a6}$ and $R^{a7}$, taken together with the nitrogen to which they are attached, form a 5- to 7-membered saturated heterocyclic group;

$R^{a8}$ represents optionally substituted $C_{3-7}$ cycloalkyl or optionally substituted $C_{6-14}$ aromatic hydrocarbon; and $R^{a9}$ represents hydrogen, hydroxyl, amino, or mono- or di($C_{1-6}$ alkyl)amino.

The following describes the compounds represented by Formula (b).

Examples of substituents for Formula (b) include halogen, hydroxyl, cyano, amino, nitro, oxo, carboxyl, carbamoyl, alkyl, cycloalkyl, alkenyl, alkynyl, alkoxy, acyl, acyloxy, alkoxycarbonyl, saturated heterocyclic group, unsaturated heterocyclic group, aromatic hydrocarbon, halogenoalkyl, aralkyl, unsaturated heterocyclic alkyl group, alkylamino, acylamino, alkoxycarbonylamino, aralkyloxy, aminoacyloxy, unsaturated heterocyclic acyloxy group, alkyl-unsaturated heterocyclic group, and the like. The number of the substituents, if any, is typically 1 to 3.

Examples of halogen included in the substituents include chlorine, bromine, fluorine, and iodine.

The alkyl included in the substituents preferably refers to a straight or branched $C_{1-6}$ alkyl group. Examples thereof include methyl, ethyl, n-propyl, isopropyl, n-butyl, isobutyl, sec-butyl, tert-butyl, pentyl, hexyl, and the like.

The cycloalkyl included in the substituents preferably refers to a $C_{3-7}$ cycloalkyl group. Examples thereof include cyclopropyl, cyclobutyl, cyclopentyl, cyclohexyl, cycloheptyl, and the like.

The alkenyl included in the substituents preferably refers to a $C_{2-6}$ alkenyl group containing a carbon-carbon double bond. Examples thereof include vinyl, allyl, methylvinyl, propenyl, butenyl, pentenyl, hexenyl, and the like.

The alkynyl included in the substituents preferably refers to a $C_{2-6}$ alkynyl group containing a carbon-carbon triple bond. Examples thereof include ethynyl, propargyl, and the like.

The alkoxy included in the substituents preferably refers to a straight or branched $C_{1-6}$ alkoxy group. Examples thereof include methoxy, ethoxy, n-propoxy, isopropoxy, n-butoxy, isobutoxy, tert-butoxy, and the like.

The acyl included in the substituents preferably refers to a $C_{1-6}$ alkanoyl group or a $C_{7-12}$ aroyl group. Examples thereof include formyl, acetyl, propionyl, n-butyryl, isobutyryl, valeryl, isovaleryl, pivaloyl, benzoyl, and the like.

The acyloxy included in the substituents refers to an oxy group that is substituted with the acyl mentioned above, and is preferably an oxy group substituted with a $C_{1-6}$ alkanoyl group or a $C_{7-12}$ aroyl group. Examples thereof include formyloxy, acetoxy, propionyloxy, n-butyryloxy, isobutyryloxy, valeryloxy, isovaleryloxy, pivaloyloxy, benzoyloxy, and the like.

The alkoxycarbonyl included in the substituents refers to a carbonyl group substituted with the alkoxy mentioned above, and is preferably a carbonyl group substituted with a $C_{1-6}$ alkoxy group. Examples thereof include methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, and the like.

The saturated heterocyclic group included in the substituents preferably refers to a 5- to 10-membered monocyclic or bicyclic saturated heterocyclic group having 1 to 4 heteroatoms selected from N, S, and O. Examples thereof include pyrrolidinyl, piperidinyl, piperazinyl, hexamethyleneimino, morpholino, thiomorpholino, homopiperazinyl, tetrahydrofuranyl, tetrahydropyranyl, methylenedioxyphenyl, ethylenedioxyphenyl, dihydrobenzofuranyl, and the like.

The unsaturated heterocyclic group included in the substituents preferably refers to a 5- to 10-membered monocyclic or bicyclic unsaturated heterocyclic group having 1 to 4 heteroatoms selected from N, S, and O. Examples thereof include imidazolyl, thienyl, furyl, pyrrolyl, oxazolyl, isoxazolyl, thiazolyl, isothiazolyl, pyrazolyl, triazolyl, tetrazolyl, pyridyl, pyrazyl, pyrimidinyl, pyridazinyl, indolyl, isoindolyl, indazolyl, benzofuranyl, benzimidazolyl, benzoxazolyl, benzothiazolyl, purinyl, quinolyl, isoquinolyl, quinazolinyl, quinoxalyl, and the like.

The aromatic hydrocarbon included in the substituents preferably refers to a $C_{6-14}$ aromatic hydrocarbon group. Examples thereof include phenyl, naphthyl, and the like.

The halogenoalkyl included in the substituents refers to a group in which one to all of the hydrogen atoms of the alkyl mentioned above is substituted with the halogen mentioned above, and is preferably a group in which one to all of the hydrogen atoms of the straight or branched $C_{1-6}$ alkyl mentioned above is substituted with the halogen mentioned above. Examples thereof include difluoromethyl, trifluoromethyl, and the like.

The aralkyl included in the substituents preferably refers to a straight or branched $C_{1-6}$ alkyl group substituted with a $C_{6-14}$ aromatic hydrocarbon group. Examples thereof include benzyl, phenylethyl, phenylpropyl, naphthylmethyl, naphthylethyl, and the like.

The saturated heterocyclic alkyl included in the substituents refers to the alkyl mentioned above that is substituted with the saturated heterocyclic group mentioned above, and is preferably the straight or branched $C_{1-6}$ alkyl mentioned above substituted with a 5- to 7-membered monocyclic saturated heterocyclic group having 1 or 2 heteroatoms selected from N, S, and O. Examples thereof include morpholinomethyl, piperidinylethyl, and the like.

The alkylamino included in the substituents refers to an amino group that is mono- or disubstituted with the alkyl mentioned above, and is preferably an amino group that is mono- or disubstituted with a straight or branched $C_{1-6}$ alkyl group. Examples thereof include methylamino, ethylamino, diethylamino, methylethylamino, cyclobutylmethylamino, dimethylamino, 2-hydroxyethyl(methyl)aminomethyl, and the like.

The acylamino included in the substituents refers to an amino group that is substituted with the acyl mentioned above, and is preferably an amino group that is substituted with a $C_{1-6}$ alkanoyl group or a $C_{7-12}$ aroyl group. Examples thereof include formylamino, acetylamino, propionylamino, butyrylamino, 2-methylpropionylamino, pivaloylamino, pentanoylamino, 3-methylbutyrylamino, hexanoylamino, and the like.

The alkoxycarbonylamino included in the substituents refers to an amino group that is substituted with the alkoxycarbonyl mentioned above, and is preferably an amino group that is substituted with a carbonyl group to which a $C_{1-6}$ alkoxy group is attached. Examples thereof include methoxycarbonylamino, ethoxycarbonylamino, propoxycarbonylamino, isopropoxycarbonylamino, n-butoxycarbonylamino, isobutoxycarbonylamino, sec-butoxycarbonylamino, tert-butoxycarbonylamino, and the like.

The aralkyloxy included in the substituents refers to an oxy group having the aralkyl mentioned above, and is preferably an oxy group that is substituted with a straight or branched $C_{1-6}$ alkyl group to which a $C_{6-14}$ aromatic hydrocarbon group is attached. Examples thereof include benzyloxy, phenethyloxy, phenylpropyloxy, naphthylmethyloxy, naphthylethyloxy, and the like.

The aminoacyloxy included in the substituents refers to an oxy group substituted with the acyl mentioned above to which an amino group is attached, and is preferably an oxy group substituted with the $C_{1-6}$ alkanoyl mentioned above to which an amino group is attached or the $C_{7-12}$ aroyl mentioned above to which an amino group is attached. Examples thereof include aminoacetoxy, 2-aminopropionyloxy, 2-amino-4-methylpentanoyloxy, and the like.

The saturated heterocyclic acyloxy group included in the substituents refers to an oxy group substituted with the acyl mentioned above to which the saturated heterocyclic group is attached, and is preferably the $C_{1-6}$ alkanoyl mentioned above to which the 5- to 10-membered monocyclic or bicyclic saturated heterocyclic group having 1 to 4 heteroatoms selected from N, S, and O mentioned above is attached, or preferably an oxy group substituted with the $C_{7-12}$ aroyl mentioned above. Examples thereof include morpholinoacetoxy, and the like.

In Formula (b), at least one of $X^{b1}$, $X^{b2}$, $X^{b3}$, and $X^{b4}$ represents N or N-oxide, and the others are identical or different and each represents C—$R^{b2}$. In Formula (b), it is preferable that $X^{b2}$ represents C—$R^{b2}$, at least one of $X^{b1}$, $X^{b3}$, and $X^{b4}$ represents N or N-oxide, and the others each represent CH. Based on these definitions of $X^{b1}$ to $X^{b4}$, examples of the bicyclo skeleton in Formula (b) include the following structures:

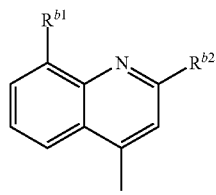
(A-1b)

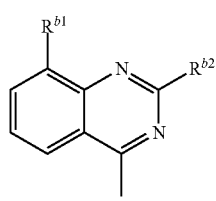
(A-2b)

-continued

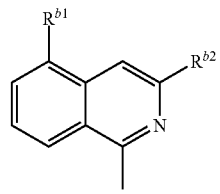
(A-3b)

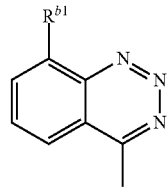
(A-4b)

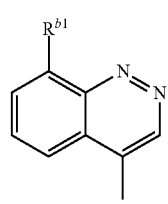
(A-5b)

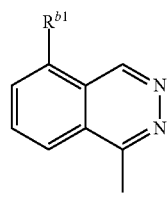
(A-6b)

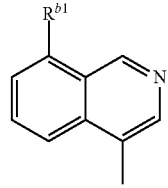
(A-7b)

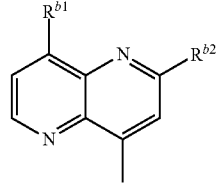
(A-8b)

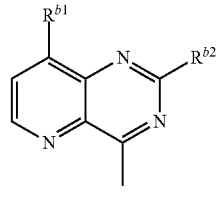
(A-9b)

(A-10b)

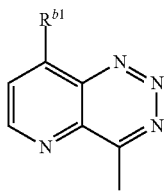
(A-11b)

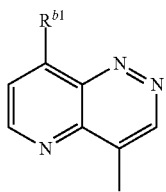
(A-12b)

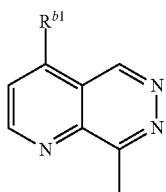
(A-13b)

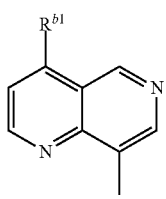
(A-14b)

wherein $R^{b1}$ and $R^{b2}$ are as defined above.

Of these skeletons, (A-1b), (A-2b), (A-3b), (A-8b), (A-9b), (A-10b), and (A-15b) are preferable, and (A-1b), (A-2b), and (A-3b) are particularly preferable.

In Formula (b), the "monocyclic or bicyclic unsaturated heterocyclic group having 1 to 4 heteroatoms selected from N, S, and O" in the "optionally substituted monocyclic or bicyclic unsaturated heterocyclic group having 1 to 4 heteroatoms selected from N, S, and O" represented by $R^{b1}$ is preferably a monocyclic or bicyclic 5- to 10-membered unsaturated heterocyclic group having 1 to 3 heteroatoms selected from N, S, and O, and more preferably a monocyclic 5- to 6-membered unsaturated heterocyclic group having 1 to 3 heteroatoms selected from N, S, and O, or a bicyclic 9- to 10-membered unsaturated heterocyclic group having 1 to 3 heteroatoms selected from N, S, and O. Examples of the unsaturated heterocyclic group include imidazolyl, pyrazolyl, thienyl, furyl, pyrrolyl, oxazolyl, isoxazolyl, thiazolyl, isothiazolyl, pyrazolyl, triazolyl, tetrazolyl, pyridyl, pyrazyl, pyrimidinyl, pyridazinyl, indolyl, isoindolyl, pyrrolopyridyl, indazolyl, methylenedioxyphenyl, ethylenedioxyphenyl, benzofuranyl, dihydrobenzofuranyl, benzimidazolyl, benzoxazolyl, benzothiazolyl, purinyl, quinolyl, tetrahydroquinolyl, isoquinolyl, quinazolinyl, quinoxalinyl, and the like. The unsaturated heterocyclic group is preferably imidazolyl, thiazolyl, oxadiazolyl, thiadiazolyl, pyridyl, pyrazyl, pyrimidinyl, pyridazinyl, pyridopyrazyl, quinolyl, imidazopyridyl, or pyrrolopyridyl, more preferably quinolyl, imidazopyridyl, pyridopyrazyl, pyridyl, imidazolyl, pyrrolopyridyl, or pyrimidinyl, further preferably quinolyl, imidazopyridyl, pyridyl, imidazolyl, or pyrrolopyridyl, and particularly preferably quinolyl, pyridyl, or imidazolyl.

In Formula (b), examples of substituents for the unsaturated heterocyclic group represented by $R^{b1}$ include the substituents mentioned above. The number of the substituents is 1 to 3. The substituent is preferably halogen, amino, optionally substituted $C_{1-6}$ alkyl, optionally substituted $C_{1-6}$ alkoxy, optionally substituted $C_{1-6}$ alkylamino, optionally substituted $C_{1-6}$ acyl, optionally substituted carbamoyl, optionally substituted $C_{1-6}$ acylamino, optionally substituted aromatic hydrocarbon, an optionally substituted unsaturated heterocyclic group, or an optionally substituted saturated heterocyclic group.

The substituent is more preferably halogen; amino; $C_{1-6}$ alkyl optionally having a substituent selected from hydroxyl, amino, $C_{1-6}$ alkoxycarbonylamino, and a saturated heterocyclic group; $C_{1-6}$ alkoxy; $C_{1-6}$ alkylamino optionally having $C_{3-7}$ cycloalkyl; $C_{1-6}$ acyl; carbamoyl optionally having a substituent selected from $C_{1-6}$ alkyl, a saturated heterocyclic group optionally substituted with $C_{1-6}$ alkyl, and aromatic hydrocarbon; $C_{1-6}$ acylamino optionally having hydroxyl; an unsaturated heterocyclic group optionally having a substituent selected from $C_{1-6}$ alkyl and $C_{1-6}$ halogenoalkyl; or aromatic hydrocarbon.

The substituent is even more preferably halogen; amino; $C_{1-6}$ alkyl optionally having hydroxyl; $C_{1-6}$ alkoxy; $C_{1-6}$ alkylamino; $C_{1-6}$ acyl; $C_{1-6}$ acylamino optionally having hydroxyl; an unsaturated heterocyclic group optionally having a substituent selected from $C_{1-6}$ alkyl and $C_{1-6}$ halogenoalkyl; or aromatic hydrocarbon.

The substituent is furthermore preferably $C_{1-6}$ alkyl; $C_{1-6}$ alkylamino; $C_{1-6}$ acyl; $C_{1-6}$ acylamino optionally having hydroxyl; or an unsaturated heterocyclic group optionally having a substituent selected from $C_{1-6}$ alkyl and $C_{1-6}$ halogenoalkyl.

The halogen that may be substituted on the unsaturated heterocyclic ring represented by $R^{b1}$ refers to, for example, the halogen mentioned above, and is preferably bromine.

The "optionally substituted $C_{1-6}$ alkyl" that may be substituted on the unsaturated heterocyclic ring represented by $R^{b1}$ refers to, for example, the $C_{1-6}$ alkyl mentioned above optionally having the substituent mentioned above, and is preferably $C_{1-6}$ alkyl optionally having a substituent selected from hydroxyl, amino, $C_{1-6}$ alkoxycarbonylamino, and a saturated heterocyclic group. More specifically, methyl, ethyl, n-propyl, isopropyl, hydroxymethyl, aminoethyl, tert-butoxycarbonylaminoethyl, morpholinomethyl, or the like is preferable.

The "optionally substituted $C_{1-6}$ alkoxy" that may be substituted on the unsaturated heterocyclic ring represented by $R^{b1}$ refers to, for example, the $C_{1-6}$ alkoxy mentioned above optionally having the substituent mentioned above, and is preferably unsubstituted $C_{1-6}$ alkoxy. More specifically, methoxy or ethoxy is preferable.

The "optionally substituted $C_{1-6}$ alkylamino" that may be substituted on the unsaturated heterocyclic ring represented by $R^{b1}$ refers to, for example, the $C_{1-6}$ alkylamino mentioned above optionally having the substituent mentioned above, and is preferably $C_{1-6}$ alkylamino optionally having $C_{3-7}$ cycloalkyl. More specifically, methylamino, ethylamino, n-propylamino, cyclobutylmethylamino, or the like is preferable.

The "optionally substituted acyl" that may be substituted on the unsaturated heterocyclic ring represented by $R^{b1}$ refers to, for example, the $C_{1-6}$ acyl mentioned above optionally having the substituent mentioned above, and is preferably unsubstituted $C_{1-6}$ acyl. More specifically, formyl, acetyl, propionyl, or the like is preferable.

The "optionally substituted carbamoyl" that may be substituted on the unsaturated heterocyclic ring represented by $R^{b1}$ refers to, for example, the carbamoyl mentioned above optionally having the substituent mentioned above, and is preferably a carbamoyl group optionally having a substituent selected from $C_{1-6}$ alkyl, a saturated heterocyclic group optionally substituted with $C_{1-6}$ alkyl, and aromatic hydrocarbon. More specifically, methylcarbamoyl, ethylcarbamoyl, n-propylcarbamoyl, (1-methylpiperidin-4-yl)carbamoyl, phenylcarbamoyl, or the like is preferable.

The "optionally substituted $C_{1-6}$ acylamino" that may be substituted on the unsaturated heterocyclic ring represented by $R^{b1}$ refers to, for example, the $C_{1-6}$ acylamino mentioned above optionally having the substituent mentioned above, and is preferably $C_{1-6}$ acylamino optionally having hydroxyl. More specifically, acetylamino, 2-hydroxyacetylamino, or propionylamino is preferable.

The "optionally substituted unsaturated heterocyclic group" that may be substituted on the unsaturated heterocyclic ring represented by $R^{b1}$ refers to, for example, the unsaturated heterocyclic group mentioned above optionally having the substituent mentioned above, and is preferably an unsaturated heterocyclic group optionally having a substituent selected from $C_{1-6}$ alkyl and $C_{1-6}$ halogenoalkyl. More specifically, 1-methyl-1H-pyrazol-4-yl, 1-ethyl-1H-pyrazol-4-yl, 1-isopropyl-1H-pyrazol-4-yl, 1-isobutyl-1H-pyrazol-4-yl, 1-difluoromethyl-1H-pyrazol-4-yl, 1-oxidopyridin-3-yl, pyridin-3-yl, pyridin-4-yl, or 6-methylpyridin-3-yl is preferable.

The "optionally substituted aromatic hydrocarbon" that may be substituted on the unsaturated heterocyclic ring represented by $R^{b1}$ refers to, for example, the aromatic hydrocarbon mentioned above optionally having the substituent mentioned above, and is preferably unsubstituted aromatic hydrocarbon. More specifically, phenyl, naphthyl, or the like is preferable.

$R^{b1}$ is preferably an optionally substituted monocyclic or bicyclic 5- to 10-membered unsaturated heterocyclic group having 1 to 3 heteroatoms selected from N, S, and O, and more preferably a monocyclic or bicyclic 5- to 10-membered unsaturated heterocyclic group having 1 to 3 heteroatoms selected from N, S, and O and optionally having a substituent selected from halogen, amino, optionally substituted $C_{1-6}$ alkyl, optionally substituted $C_{1-6}$ alkoxy, optionally substituted $C_{1-6}$ alkylamino, optionally substituted $C_{1-6}$ acyl, optionally substituted $C_{1-6}$ acylamino, optionally substituted carbamoyl, optionally substituted aromatic hydrocarbon, an optionally substituted unsaturated heterocyclic group, and an optionally substituted saturated heterocyclic group.

Of these groups, a monocyclic 5- to 6-membered unsaturated heterocyclic group having 1 to 3 heteroatoms selected from N, S, and O or a bicyclic 9- to 10-membered unsaturated heterocyclic group having 1 to 3 heteroatoms selected from N, S, and O is more preferable, both groups optionally having a substituent selected from halogen; amino; $C_{1-6}$ alkyl optionally having a substituent selected from hydroxyl, amino, $C_{1-6}$ alkoxycarbonylamino, and a saturated heterocyclic group; $C_{1-6}$ alkoxy; $C_{1-6}$ alkylamino optionally having $C_{3-7}$ cycloalkyl; $C_{1-6}$ acyl; carbamoyl optionally having a substituent selected from $C_{1-6}$ alkyl, a saturated heterocyclic group optionally substituted with $C_{1-6}$ alkyl, and aromatic hydrocarbon; $C_{1-6}$ acylamino optionally having hydroxyl; an unsaturated heterocyclic group optionally having a substituent selected from $C_{1-6}$ alkyl and $C_{1-6}$ halogenoalkyl; and aromatic hydrocarbon.

$R^{b1}$ is even more preferably a monocyclic 5- to 6-membered unsaturated heterocyclic group having 1 to 3 heteroatoms selected from N, S, and O, and optionally having a substituent selected from halogen; amino; $C_{1-6}$ alkyl optionally having a substituent selected from hydroxyl, amino, $C_{1-6}$ alkoxycarbonylamino, and a saturated heterocyclic group; $C_{1-6}$ alkoxy; $C_{1-6}$ alkylamino optionally having $C_{3-7}$ cycloalkyl; $C_{1-6}$ acyl; carbamoyl optionally having a substituent selected from $C_{1-6}$ alkyl, a saturated heterocyclic group optionally substituted with $C_{1-6}$ alkyl, and aromatic hydrocarbon; $C_{1-6}$ acylamino optionally having hydroxyl; an unsaturated heterocyclic group optionally having a substituent selected from $C_{1-6}$ alkyl and $C_{1-6}$ halogenoalkyl; and aromatic hydrocarbon, or even more preferably a bicyclic 9- to 10-membered unsaturated heterocyclic group having 1 to 3 heteroatoms selected from N, S, and O and optionally having a substituent selected from $C_{1-6}$ alkyl optionally having a saturated heterocyclic group, and $C_{1-6}$ acyl.

$R^{b1}$ is still more preferably a monocyclic 5- to 6-membered unsaturated heterocyclic group having 1 to 3 heteroatoms selected from N, S, and O, and optionally having a substituent selected from halogen; amino; $C_{1-6}$ alkyl optionally having a substituent selected from hydroxyl, amino, and $C_{1-6}$ alkoxycarbonylamino; $C_{1-6}$ alkoxy; $C_{1-6}$ alkylamino optionally having $C_{3-7}$ cycloalkyl; $C_{1-6}$ acylamino optionally having hydroxyl; an unsaturated heterocyclic group optionally having a substituent selected from $C_{1-6}$ alkyl and $C_{1-6}$ halogenoalkyl; and aromatic hydrocarbon, or still more preferably a bicyclic 9- to 10-membered unsaturated heterocyclic group having 1 to 3 heteroatoms selected from N, S, and O and optionally having a substituent selected from $C_{1-6}$ acyl and $C_{1-6}$ alkyl optionally having a saturated heterocyclic group.

$R^{b1}$ is still even more preferably a monocyclic 5- to 6-membered unsaturated heterocyclic group having 1 to 3 heteroatoms selected from N, S, and O and optionally having a substituent selected from $C_{1-6}$ alkyl; $C_{1-6}$ alkylamino; $C_{1-6}$ acylamino optionally having hydroxyl; and an unsaturated heterocyclic group optionally having a substituent selected from $C_{1-6}$ alkyl and $C_{1-6}$ halogenoalkyl, or still even more preferably a bicyclic 9- to 10-membered unsaturated heterocyclic group having 1 to 3 heteroatoms selected from N, S, and O and optionally having a substituent selected from $C_{1-6}$ alkyl and $C_{1-6}$ acyl.

$R^{b1}$ is further preferably a monocyclic 5- to 6-membered unsaturated heterocyclic group having 1 to 3 heteroatoms selected from N, S, and O or a bicyclic 9- to 10-membered unsaturated heterocyclic group having 1 to 3 heteroatoms selected from N, S, and O, both of which groups optionally having a substituent selected from halogen; amino; $C_{1-6}$ alkyl optionally having a substituent selected from hydroxyl, amino, $C_{1-6}$ alkoxycarbonylamino, and a saturated heterocyclic group; $C_{1-6}$ alkoxy; $C_{1-6}$ alkylamino optionally having $C_{3-7}$ cycloalkyl; $C_{1-6}$ acyl; carbamoyl optionally having a substituent selected from $C_{1-6}$ alkyl, a saturated heterocyclic group optionally substituted with $C_{1-6}$ alkyl, and aromatic hydrocarbon; $C_{1-6}$ acylamino optionally having hydroxyl; an unsaturated heterocyclic group optionally having a substituent selected from $C_{1-6}$ alkyl and $C_{1-6}$ halogenoalkyl; and aromatic hydrocarbon, wherein the monocyclic or bicyclic unsaturated heterocyclic group is preferably imidazolyl, pyrazolyl, thienyl, furyl, pyrrolyl, oxazolyl, isoxazolyl, thiazolyl, isothiazolyl, pyrazolyl, triazolyl, tetrazolyl, pyridyl, pyrazyl, pyrimidinyl, pyridazinyl, indolyl, isoindolyl, pyrrolopyridyl, indazolyl, methylenedioxyphenyl, ethylenedioxyphenyl, benzofuranyl, dihydrobenzofuranyl, benzimidazolyl, benzoxazolyl, benzothiazolyl, purinyl, quinolyl, tetrahydroquinolyl, isoquinolyl, quinazolinyl, or quinoxalyl.

$R^{b1}$ is still more preferably a monocyclic 5- to 6-membered unsaturated heterocyclic group having 1 to 3 heteroatoms selected from N, S, and O and optionally having a substituent selected from halogen; amino; $C_{1-6}$ alkyl optionally having a substituent selected from hydroxyl, amino, $C_{1-6}$ alkoxycarbonylamino, and a saturated heterocyclic group; $C_{1-6}$ alkoxy; $C_{1-6}$ alkylamino optionally having $C_{3-7}$ cycloalkyl; $C_{1-6}$ acyl; carbamoyl optionally having a substituent selected from $C_{1-6}$ alkyl, a saturated heterocyclic group optionally substituted with $C_{1-6}$ alkyl, and aromatic hydrocarbon; $C_{1-6}$ acylamino optionally having hydroxyl; unsaturated heterocyclic group optionally having a substituent selected from $C_{1-6}$ alkyl and $C_{1-6}$ halogenoalkyl; and still more preferably a bicyclic 9- to 10-membered unsaturated heterocyclic group having 1 to 3 heteroatoms selected from N, S, and O and optionally having a substituent selected from $C_{1-6}$ alkyl optionally having a saturated heterocyclic group, and $C_{1-6}$ acyl, wherein the monocyclic or bicyclic unsaturated heterocyclic group is preferably imidazolyl, pyrazolyl, thienyl, furyl, pyrrolyl, oxazolyl, isoxazolyl, thiazolyl, isothiazolyl, pyrazolyl, triazolyl, tetrazolyl, pyridyl, pyrazyl, pyrimidinyl, pyridazinyl, indolyl, isoindolyl, pyrrolopyridyl, indazolyl, methylenedioxyphenyl, ethylenedioxyphenyl, benzofuranyl, dihydrobenzofuranyl, benzimidazolyl, benzoxazolyl, benzothiazolyl, purinyl, quinolyl, tetrahydroquinolyl, isoquinolyl, quinazolinyl, or quinoxalyl.

$R^{b1}$ is even more preferably a monocyclic 5- to 6-membered unsaturated heterocyclic group having 1 to 3 heteroatoms selected from N, S, and O, and optionally having a substituent selected from halogen; amino; $C_{1-6}$ alkyl optionally having a substituent selected from hydroxyl, amino, and $C_{1-6}$ alkoxycarbonylamino; $C_{1-6}$ alkoxy; $C_{1-6}$ alkylamino optionally having $C_{3-7}$ cycloalkyl; $C_{1-6}$ acylamino optionally having hydroxyl; an unsaturated heterocyclic group optionally having a substituent selected from $C_{1-6}$ alkyl and $C_{1-6}$ halogenoalkyl; and aromatic hydrocarbon, or even more preferably a bicyclic 9- to 10-membered unsaturated heterocyclic group having 1 to 3 heteroatoms selected from N, S, and O, and optionally having a substituent selected from $C_{1-6}$ alkyl optionally having a saturated heterocyclic group, and $C_{1-6}$ acyl, wherein the monocyclic or bicyclic unsaturated heterocyclic group is preferably imidazolyl, thiazolyl, oxadiazolyl, thiadiazolyl, pyridyl, pyrazyl, pyrimidinyl, pyridazinyl, pyridopyrazyl, quinolyl, imidazopyridyl, or pyrrolopyridyl.

$R^{b1}$ is further preferably an unsaturated heterocyclic group selected from imidazolyl, thiazolyl, oxadiazolyl, thiadiazolyl, pyridyl, pyrazyl, pyrimidinyl, and pyridazinyl, optionally having a substituent selected from $C_{1-6}$ alkyl; $C_{1-6}$ alkylamino; $C_{1-6}$ acylamino optionally having hydroxyl; and an unsaturated heterocyclic group optionally having a substituent selected from $C_{1-6}$ alkyl and $C_{1-6}$ halogenoalkyl, or further preferably an unsaturated heterocyclic group selected from pyridopyrazyl, quinolyl, imidazopyridyl, and pyrrolopyridyl, optionally having a substituent selected from $C_{1-6}$ alkyl and $C_{1-6}$ acyl.

$R^{b1}$ is particularly preferably imidazolyl or pyridyl optionally having a substituent selected from $C_{1-6}$ alkyl; $C_{1-6}$ alkylamino; $C_{1-6}$ acylamino optionally having hydroxyl; and an unsaturated heterocyclic group optionally having a substituent selected from $C_{1-6}$ alkyl and $C_{1-6}$ halogenoalkyl, or particularly preferably quinolyl optionally having a substituent selected from $C_{1-6}$ alkyl and $C_{1-6}$ acyl.

More specifically, preferable examples of $R^{b1}$ include thiazol-5-yl, 2-phenylthiazol-5-yl, 5-phenyl-1,3,4-oxadiazol-2-yl, 5-phenyl-1,3,4-thiadiazol-2-yl, 4-bromo-1H-imidazol-1-yl, 4-acetyl-1H-imidazol-1-yl, 4-phenyl-1H-imidazol-1-yl, 4-(pyridin-3-yl)-1H-imidazol-1-yl, 4-(pyridin-4-yl)-1H-imidazol-1-yl, 4-(1-oxidopyridin-3-yl)-1H-imidazol-1-yl, 4-(6-methylpyridin-3-yl)-1H-imidazol-1-yl, 4-(1-methyl-1H-pyrazol-4-yl)-1H-imidazol-1-yl, 4-(1-ethyl-1H-pyrazol-4-yl)-1H-imidazol-1-yl, 4-(1-isopropyl-1H-pyrazol-4-yl)-1H-imidazol-1-yl, 4-(1-isobutyl-1H-pyrazol-4-yl)-1H-imidazol-1-yl, 4-(1-difluoromethyl-1H-pyrazol-4-yl)-1H-imidazol-1-yl, 5-(6-ethylamino)pyrazin-2-yl, pyridin-3-yl, 5-aminopyridin-3-yl, 5-(hydroxymethyl)pyridin-3-yl, 5-(2-aminoethyl)pyridin-3-yl, 5-(tert-butoxycarbonylaminoethyl)pyridin-3-yl, 5-(morpholinomethyl)pyridin-3-yl, 5-methoxypyridin-3-yl, 6-methoxypyridin-3-yl, 5-(methylamino)pyridin-3-yl, 5-(propylamino)pyridin-3-yl, 5-(cyclobutylmethylamino)pyridin-3-yl, 5-acetamidopyridin-3-yl, 5-(2-hydroxyacetamido)pyridin-3-yl, 6-methylcarbamoyl-pyridin-3-yl, 4-propylcarbamoyl-pyridin-3-yl, 5-(1-methylpiperidin-4-yl)carbamoyl-pyridin-3-yl, 6-phenylcarbamoyl-pyridin-3-yl, pyrimidin-5-yl, 6-methoxypyridazin-3-yl, quinolin-3-yl, 6-methylquinolin-3-yl, 7-methylquinolin-3-yl, 6-(morpholinomethyl)quinolin-3-yl, 7-formylquinolin-3-yl, 1H-imidazo[4,5-b]pyridin-6-yl, 2-methyl-1H-imidazo[4,5-b]pyridin-6-yl, 2-ethyl-1H-imidazo[4,5-b]pyridin-6-yl, 7-methyl-1H-imidazo[4,5-b]pyridin-6-yl, 1H-pyrrolo[2,3-b]pyridin-5-yl, 1H-pyrrolo[3,2-b]pyridin-6-yl, and pyrido[2,3-b]pyrazin-7-yl. $R^{b1}$ is more preferably 4-(1-methyl-1H-pyrazol-4-yl)-1H-imidazol-1-yl, quinolin-3-yl, 4-(pyridin-3-yl)-1H-imidazol-1-yl, 4-(6-methylpyridin-3-yl)-1H-imidazol-1-yl, 4-(1-difluoromethyl-1H-pyrazol-4-yl)-1H-imidazol-1-yl, 4-(pyridin-4-yl)-1H-imidazol-1-yl, 4-phenyl-1H-imidazol-1-yl, or 4-(1-ethyl-1H-pyrazol-4-yl)-1H-imidazol-1-yl, and particularly preferably 4-(1-methyl-1H-pyrazol-4-yl)-1H-imidazol-1-yl, quinolin-3-yl, or 4-(pyridin-3-yl)-1H-imidazol-1-yl.

In Formula (b), the "optionally substituted $C_{1-6}$ alkyl" represented by $R^{b2}$ refers to, for example, the $C_{1-6}$ alkyl mentioned above optionally having the substituent mentioned above, and is preferably $C_{1-6}$ alkyl optionally having a substituent selected from halogen and a saturated heterocyclic group. More specifically, methyl, ethyl, n-propyl, isopropyl, n-butyl, isobutyl, sec-butyl, tert-butyl, pentyl, hexyl, trifluoromethyl, or morpholinomethyl is preferable.

In Formula (b), the "optionally substituted $C_{3-7}$ cycloalkyl" represented by $R^{b2}$ refers to, for example, the $C_{3-7}$ cycloalkyl mentioned above optionally having the substituent, and is preferably unsubstituted $C_{3-7}$ cycloalkyl. More specifically, cyclopropyl is preferable.

In Formula (b), the "optionally substituted $C_{2-6}$ alkenyl" represented by $R^{b2}$ refers to, for example, the $C_{2-6}$ alkenyl mentioned above optionally having the substituent mentioned above, and is preferably unsubstituted $C_{2-6}$ alkenyl. More specifically, vinyl is preferable.

$R^{b2}$ is preferably hydrogen; $C_{1-6}$ alkyl optionally having a substituent selected from halogen and a saturated heterocyclic group; or $C_{3-7}$ cycloalkyl, and more preferably hydrogen; $C_{1-6}$ alkyl optionally having halogen; or $C_{3-7}$ cycloalkyl.

One or two of $Y^{b1}$, $Y^{b2}$, $Y^{b3}$, and $Y^{b4}$ represent C—$R^{b4}$, and the others are identical or different and each represents CH or N. Of these, it is preferable that $Y^{b4}$ represents C—$R^{b4}$ or N, and $Y^{b1}$ to $Y^{b3}$ each represent CH, or that $Y^{b2}$ to $Y^{b4}$ each represent CH, and $Y^{b1}$ represents C—$R^{b4}$. These preferable embodiments are represented by the following structural formulas:

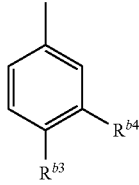

(B-1b)

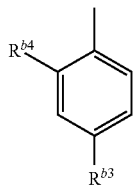

(B-2b)

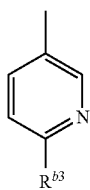

(B-3b)

wherein $R^{b3}$ and $R^{b4}$ are as defined above.

Of these structures, (B-1b) and (B-2b) are more preferable, and (B-1b) is particularly preferable.

In Formula (b), the "halogen" represented by $R^{b3}$ refers to, for example, the halogen mentioned above, and is preferably bromine.

In Formula (b), the "$C_{1-6}$ alkyl" represented by $R^{b3}$ refers to, for example, the alkyl mentioned above, and is preferably methyl.

In Formula (b), the "$C_{1-6}$ alkoxy" represented by $R^{b3}$ refers to, for example, the alkoxy mentioned above, and is preferably methoxy.

$R^{b3}$ is preferably hydrogen, cyano, $C_{1-6}$ alkoxy, or —CO—$R^{b5}$, more preferably cyano or —CO—$R^{b5}$, and further preferably —CO—$R^{b5}$.

In Formula (b), the "optionally substituted $C_{1-6}$ alkylamino" represented by $R^{b5}$ refers to, for example, the $C_{1-6}$ alkylamino mentioned above optionally having the substituent mentioned above, and is preferably $C_{1-6}$ alkylamino optionally having $C_{1-6}$ alkylamino (the alkyl moiety is optionally substituted with hydroxyl). More specifically, 2-hydroxyethylmethylaminomethylamino or dimethylaminomethylamino is preferable.

$R^{b5}$ is more preferably amino or $C_{1-6}$ alkylamino optionally having $C_{1-6}$ alkylamino (the alkyl moiety is optionally substituted with hydroxyl), and particularly preferably amino.

In Formula (b), the "halogen" represented by $R^{b4}$ refers to, for example, the halogen mentioned above, and is preferably chlorine or fluorine.

In Formula (b), the "$C_{1-6}$ alkyl" represented by $R^{b4}$ refers to, for example, the $C_{1-6}$ alkyl mentioned above, and is preferably methyl, ethyl, n-propyl, or isopropyl.

In Formula (b), the "$C_{1-6}$ alkoxy" represented by $R^{b4}$ refers to, for example, the $C_{1-6}$ alkoxy mentioned above, and is preferably methoxy.

$R^{b4}$ is preferably hydrogen, halogen, $C_{1-6}$ alkyl, $C_{1-6}$ alkoxy, or —N($R^{b7}$)($R^{b8}$), more preferably halogen, $C_{1-6}$ alkyl, or —N($R^{b7}$)($R^{b8}$), and particularly preferably —N($R^{b7}$)($R^{b8}$).

In Formula (b), the "optionally substituted $C_{1-6}$ alkylamino" represented by $R^{b6}$ refers to, for example, the $C_{1-6}$ alkylamino mentioned above optionally having the substituent.

$R^{b6}$ is preferably amino or $C_{1-6}$ alkylamino, and particularly preferably amino.

In Formula (b), the "optionally substituted $C_{1-6}$ alkyl" represented by $R^{b7}$ or $R^{b8}$ refers to, for example, the $C_{1-6}$ alkyl mentioned above optionally having the substituent mentioned above, and is preferably $C_{1-6}$ alkyl optionally having a substituent selected from $C_{1-6}$ alkoxy, $C_{3-7}$ cycloalkyl, a saturated heterocyclic group, and an unsaturated heterocyclic group. More specifically, methyl, ethyl, n-propyl, isopropyl, n-butyl, isobutyl, sec-butyl, tert-butyl, cyclopropylmethyl, 2-methoxyethyl, 2-isopropoxyethyl, tetrahydrofuranmethyl, or 2-pyridylethyl is preferable.

In Formula (b), the "optionally substituted $C_{3-7}$ cycloalkyl" represented by $R^{b7}$ or $R^{b8}$ refers to, for example, the $C_{3-7}$ cycloalkyl mentioned above optionally having the substituent mentioned above, and is preferably $C_{3-7}$ cycloalkyl optionally having a substituent selected from hydroxyl, amino, aminoacyloxy, and an unsaturated heterocyclic acyloxy group. More specifically, 4-hydroxycyclohexyl, cycloheptyl, 4-(aminoacetoxy)cyclohexyl, 4-(2-aminopropionyloxy)cyclohexyl, 4-(2-amino-4-methylpentanoyloxy)cyclohexyl, or 4-(morpholinoacetoxy)cyclohexyl is preferable.

In Formula (b), the "optionally substituted aromatic hydrocarbon" represented by $R^{b7}$ or $R^{b8}$ refers to, for example, the $C_{6-14}$ aromatic hydrocarbon mentioned above optionally having the substituent mentioned above.

In Formula (b), the "optionally substituted saturated heterocyclic group" represented by $R^{b7}$ or $R^{b8}$ refers to, for example, the saturated heterocyclic group mentioned above optionally having the substituent mentioned above, and is preferably a saturated heterocyclic group optionally having $C_{1-6}$ alkyl. More specifically, for example, 1-methylpiperidin-4-yl is preferable.

In Formula (b), the "optionally substituted unsaturated heterocyclic group" represented by $R^{b7}$ or $R^{b8}$ refers to, for example, the unsaturated heterocyclic group mentioned above optionally having the substituent mentioned above.

In Formula (b), the "saturated heterocyclic group" that may be formed by $R^{b7}$ and $R^{b8}$ together with the nitrogen to which they are attached refers to a monocyclic or bicyclic saturated heterocyclic group having, preferably, 1 to 4 atoms selected from oxygen, nitrogen, and sulfur. Examples thereof include pyrrolidinyl, piperidinyl, piperazinyl, hexamethyleneimino, morpholino, thiomorpholino, homopiperazinyl, tetrahydrofuranyl, and tetrahydropyranyl.

In Formula (b), a preferable combination of $R^{b7}$ and $R^{b8}$ is such that $R^{b7}$ represents hydrogen, and $R^{b8}$ represents hydrogen, optionally substituted $C_{1-6}$ alkyl, optionally substituted $C_{3-7}$ cycloalkyl, or an optionally substituted monocyclic or bicyclic saturated heterocyclic group having 1 to 4 heteroatoms selected from N, S, and O, a more preferable combination is such that $R^{b7}$ represents hydrogen, and $R^{b8}$ represents hydrogen; $C_{1-6}$ alkyl optionally having a substituent selected from $C_{1-6}$ alkoxy, $C_{3-7}$ cycloalkyl, a saturated heterocyclic group, and an unsaturated heterocyclic group; $C_{3-7}$ cycloalkyl optionally having a substituent selected from hydroxyl, amino, aminoacyloxy, and a saturated heterocyclic acyloxy group; or a monocyclic or bicyclic saturated heterocyclic group having 1 to 4 heteroatoms selected from N, S, and O and optionally having $C_{1-6}$ alkyl, and a further preferable combination is such that $R^{b7}$ represents hydrogen, and $R^{b8}$ represents hydrogen; $C_{1-6}$ alkyl optionally having a substituent selected from $C_{1-6}$ alkoxy, $C_{3-7}$ cycloalkyl, a saturated heterocyclic group, and an unsaturated heterocyclic group; or $C_{3-7}$ cycloalkyl optionally having a substituent selected from hydroxyl, amino, aminoacyloxy, and a saturated heterocyclic acyloxy group.

In Formula (b), the "optionally substituted $C_{3-7}$ cycloalkyl" represented by $R^{b9}$ refers to, for example, the $C_{3-7}$ cycloalkyl mentioned above optionally having the substituent mentioned above.

In Formula (b), the "aromatic hydrocarbon" in the "optionally substituted aromatic hydrocarbon" represented by $R^{b9}$ refers to, for example, the $C_{6-14}$ aromatic hydrocarbon mentioned above optionally having the substituent mentioned above.

$R^{b9}$ is preferably optionally substituted $C_{3-7}$ cycloalkyl or optionally substituted $C_{6-14}$ aromatic hydrocarbon.

The compound of the present invention is preferably a compound represented by Formula (b) wherein $X^{b2}$ represents C—$R^{b2}$, at least one of $X^{b1}$, $X^{b3}$, and $X^{b4}$ represents N or N-oxide, and the others each represent CH, $Y^{b4}$ represents C—$R^{b4}$ or N, and $Y^{b1}$ to $Y^{b3}$ each represent CH, or $Y^{b2}$ to $Y^{b4}$ each represent CH, and $Y^{b1}$ represents C—$R^{b4}$, $R^{b1}$ is an optionally substituted monocyclic or bicyclic unsaturated heterocyclic group having 1 to 4 heteroatoms selected from N, S, and O, $R^{b2}$ represents hydrogen; $C_{1-6}$ alkyl optionally having a substituent selected from halogen and a saturated heterocyclic group; or $C_{3-7}$ cycloalkyl, $R^{b3}$ represents cyano or —CO—$R^{b5}$ wherein $R^{b5}$ is amino or $C_{1-6}$ alkylamino optionally having $C_{1-6}$ alkylamino (the alkyl moiety is optionally substituted with hydroxyl), and $R^{b4}$ represents hydrogen, halogen, $C_{1-6}$ alkyl, $C_{1-6}$ alkoxy, or —N($R^{b7}$)($R^{b8}$) wherein $R^{b7}$ is hydrogen, and $R^{b8}$ is hydrogen; $C_{1-6}$ alkyl optionally having a substituent selected from $C_{1-6}$ alkoxy, $C_{3-7}$ cycloalkyl, a saturated heterocyclic group, and an unsaturated heterocyclic group; $C_{3-7}$ cycloalkyl optionally having a substituent selected from hydroxyl, amino, aminoacyloxy, and a saturated heterocyclic acyloxy group; or a monocyclic or bicyclic saturated heterocyclic group having 1 to 4 heteroatoms selected from N, S, and O and optionally having $C_{1-6}$ alkyl.

The compound of the present invention is more preferably a compound represented by Formula (b) wherein $X^{b2}$ represents C—$R^{b2}$, $X^{b4}$ represents CH, at least one of $X^{b1}$ and $X^{b3}$ represents N or N-oxide, and the other represents CH, $Y^{b4}$ represents C—$R^{b4}$ or N, and $Y^{b1}$ to $Y^{b3}$ each represent CH, or $Y^{b2}$ to $Y^{b4}$ each represent CH, and $Y^{b1}$ represents C—$R^{b4}$, $R^{b1}$ represents an optionally substituted monocyclic or bicyclic unsaturated heterocyclic group having 1 to 4 heteroatoms selected from N, S, and O, $R^{b2}$ represents hydrogen; $C_{1-6}$ alkyl optionally having halogen; or $C_{3-7}$ cycloalkyl, $R^{b3}$ represents —CO—$R^{b5}$ wherein $R^{b5}$ is amino, and $R^{b4}$ represents halogen, $C_{1-6}$ alkyl, or —N($R^{b7}$)($R^{b8}$) wherein $R^{b7}$ is hydrogen, and $R^{b8}$ is hydrogen; $C_{1-6}$ alkyl optionally having a substituent selected from $C_{1-6}$ alkoxy, $C_{3-7}$ cycloalkyl, a saturated heterocyclic group, and an unsaturated heterocyclic group; or $C_{3-7}$ cycloalkyl optionally having a substituent selected from hydroxyl, amino, aminoacyloxy, and a saturated heterocyclic acyloxy group.

The compound of the present invention is particularly preferably a compound represented by Formula (b) wherein $X^{b2}$ represents C—$R^{b2}$, $X^{b4}$ represents CH, at least one of $X^{b1}$ and $X^{b3}$ represents N or N-oxide, and the other represents CH, $Y^{b4}$ represents C—$R^{b4}$ or N, and $Y^{b1}$ to $Y^{b3}$ each represent CH, or $Y^{b2}$ to $Y^{b4}$ each represent CH, and $Y^{b1}$ represents C—$R^{b4}$, $R^{b1}$ is a monocyclic 5- to 6-membered unsaturated heterocyclic group having 1 to 3 heteroatoms selected from N, S, and O and optionally having a substituent selected from $C_{1-6}$ alkyl; $C_{1-6}$ alkylamino; $C_{1-6}$ acylamino optionally having hydroxyl; and an unsaturated heterocyclic group optionally having a substituent selected from $C_{1-6}$ alkyl and $C_{1-6}$ halogenoalkyl, or a bicyclic 9- to 10-membered unsaturated heterocyclic group having 1 to 3 heteroatoms selected from N, S, and O and optionally having a substituent selected from $C_{1-6}$ alkyl and $C_{1-6}$ acyl, $R^{b2}$ represents hydrogen; $C_{1-6}$ alkyl optionally having halogen; or $C_{3-7}$ cycloalkyl, $R^{b3}$ represents —CO—$R^{b5}$ wherein $R^{b5}$ is amino, and $R^{b4}$ represents halogen, $C_{1-6}$ alkyl, or —N($R^{b7}$)($R^{b8}$) wherein $R^{b7}$ is hydrogen, and $R^{b8}$ is hydrogen; $C_{1-6}$ alkyl optionally having a substituent selected from $C_{1-6}$ alkoxy, $C_{3-7}$ cycloalkyl, a saturated heterocyclic group, and an unsaturated heterocyclic group; or $C_{3-7}$ cycloalkyl optionally having a substituent selected from hydroxyl, amino, aminoacyloxy, and a saturated heterocyclic acyloxy group.

The following describes the compounds represented by Formula (c).

Examples of substituents for Formula (c) include halogen, hydroxyl, cyano, amino, nitro, oxo, carboxyl, carbamoyl, alkyl, cycloalkyl, alkenyl, alkynyl, alkoxy, acyl, acyloxy, alkoxycarbonyl, saturated heterocyclic group, unsaturated heterocyclic group, aromatic hydrocarbon, halogenoalkyl, aralkyl, alkylamino, acylamino, aralkyloxy, and the like. The number of the substituents, if any, is typically 1 to 3.

Examples of halogen included in the substituents include chlorine, bromine, fluorine, and iodine.

The alkyl included in the substituents preferably refers to a straight or branched $C_{1-6}$ alkyl group. Examples thereof include methyl, ethyl, n-propyl, isopropyl, n-butyl, isobutyl, sec-butyl, tert-butyl, pentyl, hexyl, and the like.

The cycloalkyl included in the substituents preferably refers to a $C_{3-7}$ cycloalkyl group. Examples thereof include cyclopropyl, cyclobutyl, cyclopentyl, cyclohexyl, cycloheptyl, and the like.

The alkenyl included in the substituents preferably refers to a $C_{2-6}$ alkenyl group containing a carbon-carbon double bond. Examples thereof include vinyl, allyl, methylvinyl, propenyl, butenyl, pentenyl, hexenyl, and the like.

The alkynyl included in the substituents preferably refers to a $C_{2-6}$ alkynyl group containing a carbon-carbon triple bond. Examples thereof include ethynyl, propargyl, and the like.

The alkoxy included in the substituents preferably refers to a straight or branched $C_{1-6}$ alkoxy group. Examples thereof include methoxy, ethoxy, n-propoxy, isopropoxy, n-butoxy, isobutoxy, tert-butoxy, and the like.

The acyl included in the substituents preferably refers to a $C_{1-6}$ alkanoyl group or a $C_{7-12}$ aroyl group. Examples thereof include formyl, acetyl, propionyl, n-butyryl, isobutyryl, valeryl, isovaleryl, pivaloyl, benzoyl, and the like.

The acyloxy included in the substituents refers to an oxy group that is substituted with the acyl mentioned above, and is preferably an oxy group substituted with a $C_{1-6}$ alkanoyl group or a $C_{7-12}$ aroyl group. Examples thereof include formyloxy, acetoxy, propionyloxy, n-butyryloxy, isobutyryloxy, valeryloxy, isovaleryloxy, pivaloyloxy, benzoyloxy, and the like.

The alkoxycarbonyl included in the substituents refers to a carbonyl group substituted with the alkoxy mentioned above, and is preferably a carbonyl group substituted with a $C_{1-6}$ alkoxy group. Examples thereof include methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, and the like.

The saturated heterocyclic group included in the substituents preferably refers to a 5- to 10-membered monocyclic or bicyclic saturated heterocyclic group having 1 to 4 heteroatoms selected from N, S, and O. Examples thereof include pyrrolidinyl, piperidinyl, piperazinyl, hexamethyleneimino, morpholino, thiomorpholino, homopiperazinyl, tetrahydrofuranyl, tetrahydropyranyl, methylenedioxyphenyl, ethylenedioxyphenyl, dihydrobenzofuranyl, and the like.

The unsaturated heterocyclic group included in the substituents preferably refers to a 5- to 10-membered monocyclic or bicyclic unsaturated heterocyclic group having 1 to 4 heteroatoms selected from N, S, and O. Examples thereof include imidazolyl, thienyl, furyl, pyrrolyl, oxazolyl, isoxazolyl, thiazolyl, isothiazolyl, pyrazolyl, triazolyl, tetrazolyl, pyridyl, pyrazyl, pyrimidinyl, pyridazinyl, indolyl, isoindolyl, indazolyl, benzofuranyl, benzimidazolyl, benzoxazolyl, benzothiazolyl, purinyl, quinolyl, isoquinolyl, quinazolinyl, quinoxalyl, and the like.

The aromatic hydrocarbon included in the substituents preferably refers to a $C_{6-14}$ aromatic hydrocarbon group. Examples thereof include phenyl, naphthyl, and the like.

The halogenoalkyl included in the substituents refers to a group in which one to all of the hydrogen atoms of the alkyl mentioned above is substituted with the halogen mentioned above, and is preferably a group in which one to all of the hydrogen atoms of the straight or branched $C_{1-6}$ alkyl mentioned above is substituted with the halogen mentioned above. Examples thereof include difluoromethyl, trifluoromethyl, and the like.

The aralkyl included in the substituents preferably refers to a straight or branched $C_{1-6}$ alkyl group substituted with a $C_{6-14}$ aromatic hydrocarbon group. Examples thereof include benzyl, phenylethyl, phenylpropyl, naphthylmethyl, naphthylethyl, and the like.

The saturated heterocyclic alkyl included in the substituents refers to the alkyl mentioned above that is substituted with the saturated heterocyclic group mentioned above, and is preferably the straight or branched $C_{1-6}$ alkyl mentioned above substituted with a 5- to 7-membered monocyclic unsaturated heterocyclic group having 1 or 2 heteroatoms selected from N, S, and O. Examples thereof include morpholinomethyl, piperidinylethyl, and the like.

The alkylamino included in the substituents refers to an amino group that is mono- or disubstituted with the alkyl mentioned above, and is preferably an amino group that is mono- or disubstituted with a straight or branched $C_{1-6}$ alkyl group. Examples thereof include methylamino, ethylamino, diethylamino, methylethylamino, cyclobutylmethylamino, dimethylamino, 2-hydroxyethyl(methyl)aminomethyl, and the like.

The acylamino included in the substituents refers to an amino group that is substituted with the acyl mentioned above, and is preferably an amino group that is substituted with a $C_{1-6}$ alkanoyl group or a $C_{7-12}$ aroyl group. Examples thereof include formylamino, acetylamino, propionylamino, butyrylamino, 2-methylpropionylamino, pivaloylamino, pentanoylamino, 3-methylbutyrylamino, hexanoylamino, and the like.

The aralkyloxy included in the substituents refers to an oxy group having the aralkyl mentioned above, and is preferably an oxy group that is substituted with a straight or branched $C_{1-6}$ alkyl group to which a $C_{6-14}$ aromatic hydrocarbon group is attached. Examples thereof include benzyloxy, phenethyloxy, phenylpropyloxy, naphthylmethyloxy, naphthylethyloxy, and the like.

In Formula (c), $X^c$ represents CH or N, and preferably N.

In Formula (c), the "monocyclic unsaturated heterocyclic group having 1 to 4 heteroatoms selected from N, S, and O" in the "optionally substituted monocyclic unsaturated heterocyclic group having 1 to 4 heteroatoms selected from N, S, and O" represented by $A^c$ or $B^c$ is preferably a monocyclic 5- to 6-membered unsaturated heterocyclic group having 1 to 3 heteroatoms selected from N, S, and O. Examples of the unsaturated heterocyclic group include imidazolyl, pyrazolyl, thienyl, furyl, pyrrolyl, oxazolyl, oxadiazolyl, isoxazolyl, thiazolyl, isothiazolyl, pyrazolyl, triazolyl, tetrazolyl, pyridyl, pyrazyl, pyrimidinyl, pyridazinyl, triazyl, and the like.

The unsaturated heterocyclic group represented by $A^c$ is preferably a nitrogen-containing 5- to 6-membered ring, such as imidazolyl, pyrazolyl, pyrrolyl, triazolyl, tetrazolyl, pyridyl, pyrazyl, pyrimidinyl, pyridazinyl, and triazyl, and particularly preferably pyrazolyl or pyridyl.

The unsaturated heterocyclic group represented by $B^c$ is preferably a nitrogen-containing 5- to 6-member ring, such as imidazolyl, pyrazolyl, pyrrolyl, triazolyl, tetrazolyl, pyridyl, pyrazyl, pyrimidinyl, pyridazinyl, and triazyl, still more preferably a nitrogen-containing 5-membered ring, such as imidazolyl, pyrazolyl, pyrrolyl, triazolyl, and tetrazolyl, and particularly preferably imidazolyl.

In Formula (c), examples of substituents on the unsaturated heterocyclic group represented by Ac or $B^c$ include the substituents mentioned above. The number of substituents is 1 to 3. The substituent is preferably halogen, hydroxyl, amino, carbamoyl, $C_{1-6}$ alkyl, $C_{1-6}$ halogenoalkyl, $C_{1-6}$ alkoxy, $C_{1-6}$ alkylamino, $C_{1-6}$ acyl, or $C_{1-6}$ acylamino, more preferably, halogen, hydroxyl, amino, carbamoyl, $C_{1-6}$ alkyl, $C_{1-6}$ halogenoalkyl, or $C_{1-6}$ alkoxy, and particularly preferably $C_{1-6}$ alkyl.

Examples of halogen that may be substituted on the unsaturated heterocyclic ring represented by $A^c$ or $B^c$ include the halogen mentioned above.

Examples of $C_{1-6}$ alkyl that may be substituted on the unsaturated heterocyclic ring represented by $A^c$ or $B^c$ include the $C_{1-6}$ alkyl mentioned above. More specifically, methyl, ethyl n-propyl, and isopropyl are preferable, and methyl is particularly preferable.

Examples of $C_{1-6}$ alkoxy that may be substituted on the unsaturated heterocyclic ring represented by $A^c$ or $B^c$ include the $C_{1-6}$ alkoxy mentioned above. More specifically, methoxy and ethoxy are preferable.

Examples of $C_{1-6}$ alkylamino that may be substituted on the unsaturated heterocyclic ring represented by $A^c$ or $B^c$ include the $C_{1-6}$ alkylamino mentioned above. More specifically, methylamino, ethylamino, n-propylamino, cyclobutylmethylamino, and the like are preferable.

Examples of $C_{1-6}$ acyl that may be substituted on the unsaturated heterocyclic ring represented by $A^c$ or $B^c$ include the $C_{1-6}$ acyl mentioned above. More specifically, formyl, acetyl, propionyl, and the like are preferable.

Examples of $C_{1-6}$ acylamino that may be substituted on the unsaturated heterocyclic ring represented by $A^c$ or $B^c$ include the $C_{1-6}$ acylamino mentioned above. More specifically, acetylamino and propionylamino are preferable.

$A^c$ preferably represents an optionally substituted monocyclic 5- to 6-membered unsaturated heterocyclic group having 1 to 3 heteroatoms selected from N, S, and O, still more preferably a monocyclic 5- to 6-membered unsaturated heterocyclic group having 1 to 3 heteroatoms selected from N, S, and O and optionally having a substituent selected from halogen, hydroxyl, amino, carbamoyl, $C_{1-6}$ alkyl, $C_{1-6}$ halogenoalkyl, $C_{1-6}$ alkoxy, $C_{1-6}$ alkylamino, $C_{1-6}$ acyl, and $C_{1-6}$ acylamino, still more preferably a monocyclic 5- to 6-membered unsaturated heterocyclic group having 1 to 3 heteroatoms selected from N, S, and O and optionally having $C_{1-6}$ alkyl, still more preferably a monocyclic 5- to 6-membered unsaturated heterocyclic group having 1 to 3 nitrogen atoms and optionally having $C_{1-6}$ alkyl, still more preferably imidazolyl, pyrazolyl, pyrrolyl, triazolyl, pyrazyl, or pyrimidinyl, each of which optionally having $C_{1-6}$ alkyl, and furthermore preferably pyrazolyl or pyridyl, each of which optionally having $C_{1-6}$ alkyl.

Specific examples of preferable $A^c$ include 1-methyl-1H-pyrazol-4-yl and pyridin-3-yl.

$B^c$ preferably represents an optionally substituted monocyclic 5- to 6-membered unsaturated heterocyclic group having 1 to 3 heteroatoms selected from N, S, and O, still more preferably a monocyclic 5- to 6-membered unsaturated heterocyclic group having 1 to 3 heteroatoms selected from N, S, and O, and optionally having a substituent selected from halogen, hydroxyl, amino, carbamoyl, $C_{1-6}$ alkyl, $C_{1-6}$ halogenoalkyl, $C_{1-6}$ alkoxy, $C_{1-6}$ alkylamino, $C_{1-6}$ acyl, and $C_{1-6}$ acylamino, still more preferably a monocyclic 5- to 6-membered unsaturated heterocyclic group having 1 to 3 heteroatoms selected from N, S, and O, still more preferably a monocyclic 5- to 6-membered unsaturated heterocyclic group having 1 to 3 nitrogen atoms, still more preferably a monocyclic 5-membered unsaturated heterocyclic group having 1 to 3 nitrogen atoms, still more preferably imidazolyl, pyrazolyl, pyrrolyl, or triazolyl, and furthermore preferably imidazolyl.

Specific examples of preferable $B^c$ include 1H-imidazol-1-yl.

In Formula (c), the "optionally substituted $C_{1-6}$ alkyl" represented by $R^{c1}$ refers to, for example, the $C_{1-6}$ alkyl mentioned above that is optionally substituted with the substituent mentioned above, and is preferably $C_{1-6}$ alkyl optionally having halogen. More specifically, methyl, ethyl, n-propyl, isopropyl, n-butyl, isobutyl, sec-butyl, tert-butyl, pentyl, hexyl, difluoromethyl, and trifluoromethyl are preferable.

In Formula (c), the "optionally substituted $C_{3-7}$ cycloalkyl" represented by $R^{c1}$ refers to, for example, the $C_{3-7}$ cycloalkyl mentioned above optionally having the substituent mentioned above, and is preferably unsubstituted $C_{3-7}$ cycloalkyl. More specifically, cyclopropyl, cyclobutyl, cyclopentyl, and cyclohexyl are preferable, and cyclopropyl is more preferable.

In Formula (c), the "optionally substituted $C_{2-6}$ alkenyl" represented by $R^{c1}$ refers to, for example, the $C_{2-6}$ alkenyl mentioned above optionally having the substituent mentioned above, and is preferably unsubstituted $C_{2-6}$ alkenyl. More specifically, vinyl, allyl, and propenyl are preferable, and vinyl is more preferable.

$R^{c1}$ preferably represents hydrogen; $C_{1-6}$ alkyl optionally having halogen; or $C_{3-7}$ cycloalkyl, and particularly preferably hydrogen; or $C_{1-6}$ alkyl optionally having halogen.

One or two of $Y^{c1}$, $Y^{c2}$, $Y^{c3}$, and $Y^{c4}$ represent C—$R^{c3}$ or N, and the others each represent CH. Of these, it is preferable that one of $Y^{c1}$, $Y^{c2}$, $Y^{c3}$, and $Y^{c4}$ represent C—$R^{c3}$ or N, and the others each represent CH, and it is more preferable that one of $Y^{c1}$, $Y^{c2}$, $Y^{c3}$, and $Y^{c4}$ represent C—$R^{c3}$, and the others each represent CH. These preferable embodiments are represented by the following structural formulas:

(B-1c)

(B-2c)

(B-3c)

wherein $R^{c2}$ and $R^{c3}$ are as defined above.

Of these structures, (B-1c) and (B-2c) are more preferable, and (B-1c) is particularly preferable.

In Formula (c), examples of the "halogen" represented by $R^{c2}$ include the halogen mentioned above.

$R^{c2}$ preferably represents hydrogen, cyano, or —CO—$R^{c4}$, more preferably cyano or —CO—$R^{c4}$, and still more preferably CO—$R^{c4}$.

In Formula (c), examples of the $C_{1-6}$ alkylamino represented by $R^{c4}$ include the $C_{1-6}$ alkylamino mentioned above.

$R^{c4}$ more preferably represents hydroxyl or amino, and particularly preferably amino.

In Formula (c), the "halogen" represented by $R^{c3}$ refers to, for example, the halogen mentioned above, and is preferably chlorine.

In Formula (c), the "$C_{1-6}$ alkyl" represented by $R^{c3}$ refers to, for example, the $C_{1-6}$ alkyl mentioned above, and is preferably methyl, ethyl, n-propyl, or isopropyl.

In Formula (c), the "$C_{1-6}$ alkoxy" represented by $R^{c3}$ refers to, for example, the $C_{1-6}$ alkoxy mentioned above, and is preferably methoxy.

$R^{c3}$ preferably represents hydrogen, halogen, $C_{1-6}$ alkyl, $C_{1-6}$ alkoxy, or —N($R^{c6}$)($R^{c7}$), and more preferably halogen, $C_{1-6}$ alkyl, or —N($R^{c6}$)($R^{c7}$), and particularly preferably $C_{1-6}$ alkyl or —N($R^{c6}$)($R^{c7}$).

In Formula (c), examples of the "$C_{1-6}$ alkylamino" represented by $R^{c5}$ include the $C_{1-6}$ alkylamino mentioned above.

$R^{c5}$ is preferably amino or $C_{1-6}$ alkylamino, and particularly preferably amino.

In Formula (c), examples of the "$C_{1-6}$ alkyl" represented by $R^{c6}$ or $R^{c7}$ include the $C_{1-6}$ alkyl mentioned above. More specifically, methyl, ethyl, n-propyl, isopropyl, n-butyl, isobutyl, sec-butyl, and tert-butyl are preferable.

In Formula (c), examples of the "$C_{3-7}$ cycloalkyl" represented by $R^{c6}$ or $R^{c7}$ include the $C_{3-7}$ cycloalkyl mentioned above. More specifically, cyclopropyl, cyclobutyl, and cyclopentyl are preferable.

In Formula (c), examples of the "aromatic hydrocarbon" represented by $R^{c6}$ or $R^{c7}$ include the $C_{6-14}$ aromatic hydrocarbon mentioned above. More specifically, phenyl and naphthyl are preferable.

In Formula (c), examples of the "saturated heterocyclic group" represented by $R^{c6}$ or $R^{c7}$ include the monocyclic or bicyclic 5- to 10-membered saturated heterocyclic group having 1 to 4 heteroatoms selected from N, S, and O mentioned above.

In Formula (c), examples of the "unsaturated heterocyclic group" represented by $R^{c6}$ or $R^{c7}$ include the monocyclic or bicyclic 5- to 10-membered unsaturated heterocyclic group having 1 to 4 heteroatoms selected from N, S, and O mentioned above.

In Formula (c), the "saturated heterocyclic group" that may be formed by $R^{c6}$ and $R^{c7}$ together with the nitrogen to which they are attached refers to a monocyclic or bicyclic saturated heterocyclic group having preferably 1 to 4 atoms selected from oxygen, nitrogen, and sulfur. Examples thereof include pyrrolidinyl, piperidinyl, piperazinyl, hexamethyleneimino, morpholino, thiomorpholino, homopiperazinyl, tetrahydrofuranyl, and tetrahydropyranyl.

$R^{c6}$ and $R^{c7}$ are identical or different and each preferably represents hydrogen, $C_{1-6}$ alkyl, $C_{3-7}$ cycloalkyl optionally having hydroxyl, aromatic hydrocarbon, saturated heterocyclic group, or unsaturated heterocyclic group, more preferably represents hydrogen, $C_{1-6}$ alkyl, or $C_{3-7}$ cycloalkyl optionally having hydroxyl, and particularly preferably represents hydrogen, $C_{1-6}$ alkyl, or $C_{3-7}$ cycloalkyl.

In Formula (c), a preferable combination of $R^{c6}$ and $R^{c7}$ is such that $R^{c6}$ is hydrogen, and $R^{c7}$ is hydrogen, $C_{1-6}$ alkyl, or $C_{3-7}$ cycloalkyl optionally having hydroxyl, and a more preferable combination thereof is such that $R^{c6}$ is hydrogen, and $R^{c7}$ is hydrogen, $C_{1-6}$ alkyl, or $C_{3-7}$ cycloalkyl.

In Formula (c), examples of the "$C_{3-7}$ cycloalkyl" represented by $R^{c8}$ include the $C_{3-7}$ cycloalkyl mentioned above. Examples of substituents for this cycloalkyl include the substituents mentioned above.

In Formula (c), examples of the "aromatic hydrocarbon" represented by $R^{c8}$ include the $C_{6-14}$ aromatic hydrocarbon mentioned above. Examples of substituents for this aromatic hydrocarbon include the substituents mentioned above.

$R^{c8}$ preferably represents $C_{3-7}$ cycloalkyl or $C_{6-14}$ aromatic hydrocarbon.

The compound of the present invention is preferably a compound represented by Formula (c) wherein $X^c$ represents CH or N, $Y^{c4}$ represents C—$R^{c3}$ or N, and $Y^{c1}$ to $Y^{c3}$ each represent CH, or $Y^{c2}$ to $Y^{c4}$ each represent CH, and $Y^{c1}$ represents C—$R^{c3}$, $A^c$ and $B^c$ are identical or different and each represents an optionally substituted monocyclic unsaturated heterocyclic group having 1 to 4 heteroatoms selected from N, S, and O, $R^{c1}$ represents hydrogen; $C_{1-6}$ alkyl optionally having halogen; or $C_{3-7}$ cycloalkyl, $R^{c2}$ represents cyano or —CO—$R^{c4}$ wherein $R^{c4}$ is amino, $R^{c3}$ represents hydrogen, halogen, $C_{1-6}$ alkyl, $C_{1-6}$ alkoxy, or —N($R^{c6}$)($R^{c7}$) wherein $R^{c6}$ and $R^{c7}$ each represent hydrogen, $C_{1-6}$ alkyl, $C_{3-7}$ cycloalkyl optionally having hydroxyl, aromatic hydrocarbon, saturated heterocyclic group, or unsaturated heterocyclic group. The compound of the present invention is more preferably a compound represented by Formula (c) wherein $X^c$ represents CH or N, $Y^{c4}$ represents C—$R^{c3}$ or N, and $Y^{c1}$ to $Y^{c3}$ each represent CH, or $Y^{c2}$ to $Y^{c4}$ each represent CH, and $Y^{c1}$ represents C—$R^{c3}$, $A^c$ and $B^c$ are identical or different and each represents an optionally substituted monocyclic unsaturated heterocyclic group having 1 to 4 heteroatoms selected from N, S, and O, $R^{c1}$ represents hydrogen or $C_{1-6}$ alkyl optionally having halogen, $R^{c2}$ represents —CO—$R^{c4}$ wherein $R^{c4}$ represents amino, and $R^{c3}$ represents halogen, $C_{1-6}$ alkyl, or —N($R^{c6}$)($R^{c7}$) wherein $R^{c6}$ represents hydrogen, and $R^{c7}$ represents hydrogen, $C_{1-6}$ alkyl, or $C_{3-7}$ cycloalkyl.

The compound of the present invention is particularly preferably a compound represented by Formula (c) wherein $X^c$ represents CH or N, $Y^{c4}$ represents C—$R^{c3}$ or N, and $Y^{c1}$ to $Y^{c3}$ each represent CH, or $Y^{c2}$ to $Y^{c4}$ each represent CH, and $Y^{c1}$ represents C—$R^{c3}$, $A^c$ is a monocyclic 5- to 6-membered unsaturated heterocyclic group having 1 to 3 heteroatoms selected from N, S, and O and optionally having $C_{1-6}$ alkyl, $B^c$ is a monocyclic 5- to 6-membered unsaturated heterocyclic group having 1 to 3 heteroatoms selected from N, S, and O, $R^{c1}$ represents hydrogen or $C_{1-6}$ alkyl optionally having halogen, $R^{c2}$ represents —CO—$R^{c4}$ wherein $R^{c4}$ is amino, and $R^{c3}$ represents halogen, $C_{1-6}$ alkyl, or —N($R^{c6}$)($R^{c7}$) wherein $R^{c6}$ represents hydrogen, and $R^{c7}$ represents hydrogen, $C_{1-6}$ alkyl, or $C_{3-7}$ cycloalkyl.

The compound represented by Formula (a) may be produced by the method disclosed in, for example, WO 2011/004610. The compound represented by Formula (b) may be produced by the method disclosed in, for example, WO 2012/093708. The compound represented by Formula (c) may be produced by the method disclosed in, for example, WO 2012/093707.

Of the compounds represented by Formulas (a), (b), and (c), or salts thereof, the therapeutic agent of the present invention preferably contains a compound represented by Formula (a) or a salt thereof. Of these, the therapeutic agent of the present invention particularly preferably contains a compound represented by the following Formula (d) or a salt thereof (the compounds represented by Formula (d) are encompassed in the compounds represented by Formula (a)).

Formula (d):

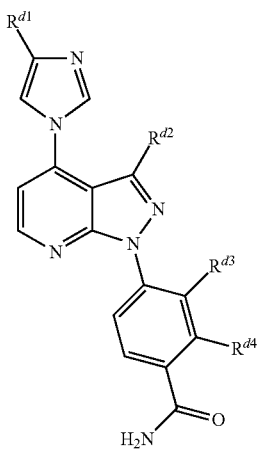

wherein $R^{d1}$ represents 1H-pyrazol-4-yl, 1-methyl-1H-pyrazol-4-yl, 1-ethyl-1H-pyrazol-4-yl, 1-isopropyl-1H-pyrazol-4-yl, pyridin-3-yl, pyridin-4-yl, or pyrimidin-5-yl;
$R^{d2}$ represents methyl, ethyl, n-propyl, isopropyl, n-butyl, isobutyl, sec-butyl, tert-butyl, or trifluoromethyl; and
$R^{d3}$ and $R^{d4}$ are such that $R^{d3}$ represents hydrogen, and $R^{d4}$ represents methyl, ethyl, n-propyl, amino, methylamino ($CH_3NH$—), or ethylamino ($CH_3CH_2NH$—), or that $R^{d4}$ represents hydrogen, and $R^{d3}$ represents methyl, ethyl, n-propyl, amino, methylamino ($CH_3NH$—), or ethylamino ($CH_3CH_2NH$—).
$R^{d1}$ preferably represents 1-methyl-1H-pyrazol-4-yl, 1-ethyl-1H-pyrazol-4-yl, or pyridin-3-yl. $R^{d2}$ preferably represents isopropyl or trifluoromethyl. $R^{d3}$ and $R^{d4}$ are preferably such that $R^{d3}$ represents hydrogen, and $R^{d4}$ represents methylamino or ethylamino, or that $R^{d4}$ represents hydrogen, and $R^{d3}$ represents methyl, ethyl, methylamino, or ethylamino.

The salts of each compound above are not limited as long as they are pharmacologically acceptable salts. Examples thereof include acid addition salts and base addition salts. Examples of acid addition salts include inorganic acid salts, such as hydrochloride, hydrobromate, sulfate, hydroiodide, nitrate, and phosphate; and organic acid salts, such as citrate, oxalate, acetate, formate, propionate, benzoate, trifluoroacetate, maleate, tartrate, methanesulfonate, benzenesulfonate, and p-toluenesulfonate. Examples of base addition salts include inorganic base salts, such as sodium salt, potassium salt, calcium salt, magnesium salt, and ammonium salt; organic base salts, such as triethylammonium salt, triethanolammonium salt, pyridinium salt, and diisopropylammonium salt; and the like. Examples thereof further include amino acid salts, such as basic or acidic amino acids, such as arginine, aspartic acid, and glutamic acid.

The diseases treated by the therapeutic agent of the present invention are not particularly limited, and may be, for example, neurodegenerative diseases, tumors, autoimmune diseases, and viral infections, with tumors being preferable.

Examples of neurodegenerative diseases include, but are not particularly limited to, Alzheimer's disease, prion diseases, Huntington's disease, and amyotrophic lateral sclerosis.

Examples of autoimmune diseases include, but are not particularly limited to, collagen disease and rheumatism.

Examples of tumors include, but are not particularly limited to, epithelial cancers (e.g., respiratory system cancers, digestive system cancers, reproductive system cancers, and endocrine system cancers), sarcomas, hematopoietic cell tumors, central nervous system tumors, peripheral nerve tumors, and the like. There is no particular limitation on the type of organs where the tumor is originated. Specific examples include head and neck cancer, esophageal cancer, gastric cancer, colon cancer, rectal cancer, liver cancer, gallbladder/bile duct cancer, biliary tract cancer, pancreatic cancer, lung cancer, breast cancer, ovarian cancer, uterine cervical cancer, endometrial cancer, renal cancer, vesical cancer, prostate cancer, testicular tumor, osteosarcoma, soft-tissue sarcoma, leukemia, malignant lymphoma, multiple myeloma, skin cancer, brain tumor, mesothelioma, and the like.

The compounds or salts thereof described above may be directly used as the therapeutic agent of the present invention. It is also possible to obtain a pharmaceutical composition by mixing the compounds or salts thereof described above with a pharmaceutically acceptable carrier, if required. The therapeutic agent of the present invention may be formed into various dosage forms according to prevention and treatment purposes. Examples of the dosage form include oral pharmaceutical preparations, injections, suppositories, ointments, patches, and the like. Of these, oral preparations are preferable. Such dosage forms may be formed by methods conventionally known to persons skilled in the art.

As a pharmaceutically acceptable carrier, various conventional organic or inorganic carrier materials used as pharmaceutical preparation materials may be used. More specific examples thereof include an excipient, binder, disintegrant, lubricant, and colorant in solid preparations; and a solvent, solubilizing agent, suspending agent, isotonizing agent, buffer, and soothing agent in liquid preparations. Moreover, pharmaceutical preparation additives, such as antiseptics, antioxidants, colorants, sweeteners, and stabilizers, may also be used, if required.

Oral pharmaceutical preparations (preferably solid oral preparations) are prepared by, for example, adding an excipient, binder, disintegrant, lubricant, colorant, sweetening/flavoring agent, or the like to the compound or a salt thereof described above to produce tablets, coated tablets, granules, powders, capsules, or the like, using an ordinary method.

Injections may be prepared by, for example, adding a pH adjuster, buffer, stabilizer, isotonizing agent, topical anesthetic, or the like, to the compound or a salt thereof described above to produce a subcutaneous injection, an intramuscular injection, or an intravenous injection using an ordinary method.

The amount of the compound or a salt thereof to be contained in the therapeutic agent of the present invention (in particular, in each dosage unit form) varies depending on the condition of the patient or on the dosage form. The desirable amount in one dosage unit form is typically about 0.05 to 1,000 mg in the case of an oral preparation, about 0.01 to 500 mg in the case of an injection, and about 1 to 1,000 mg in the case of a suppository.

The daily dose of a medicine in such a dosage form depends on the condition, body weight, age, gender, or the like, of the patient. For example, the daily dose for an adult (body weight: 50 kg) may be generally about 0.05 to 5,000 mg, and preferably 0.1 to 1,000 mg, and is preferably administered in one dose or in two to three divided doses per day.

As described above, the therapeutic agent of the present invention is used for a patient in which a protein having a mutation in the site corresponding to F138 of HSP90α class A consisting of the amino acid sequence of SEQ ID NO: 1 is expressed in HSP90 family protein. Examples of the protein include the protein according to any one of Items 1 to 11. In particular, the present invention preferably encompasses a therapeutic agent for a patient in which the above protein according to (i), (ii), or (iii) is expressed.

The patient in which the protein is expressed may be screened by a test method of determining a sample derived from a subject resistant to known HSP90 inhibitors, or a test method of determining a subject resistant to known HSP90 inhibitors.

Further, the present invention also encompasses a therapeutic method comprising administering the above compound or a salt thereof, or the above therapeutic agent to a patient in which a protein having a mutation in the site corresponding to F138 of HSP90α class A consisting of the amino acid sequence of SEQ ID NO: 1 is expressed in HSP90 family protein. The present invention further encompasses a therapeutic method comprising selecting a patient in which a protein having a mutation in the site corresponding to F138 of HSP90α class A consisting of the amino acid sequence of SEQ ID NO: 1 is expressed in HSP90 family protein by using the above test method; and administering the compound or a salt thereof, or the therapeutic agent to the selected patient.

Further, the present invention also encompasses a method of applying the above compound or a salt thereof to a protein having a mutation at the site corresponding to F138 of HSP90α class A consisting of the amino acid sequence of SEQ ID NO: 1 in HSP90 family protein, so as to inhibit the activity of the protein.

The present invention also provides a complex comprising:
(1) the protein or a part thereof encompassed in the present invention,
and
(2) a compound bonded to the protein or a part thereof.

The compound may be, for example, a compound screened by the screening method of the present invention described above.

The compound may be, for example, a compound that fills a cavity in the vicinity of at least one amino acid selected from the group consisting of 5 amino acids in sites corresponding to F170, F22, G108, Y139, or W162 of HSP90α class A consisting of the amino acid sequence of SEQ ID NO: 1 in the HSP90 family protein or a part thereof.

The compound may be, for example, a compound that interacts with at least one amino acid selected from the group consisting of 5 amino acids in sites corresponding to F170, F22, G108, Y139, or W162 of HSP90α class A consisting of the amino acid sequence of SEQ ID NO: 1 in the HSP90 family protein or a part thereof.

The compound may be, for example, geldanamycin, 17-AAG, 17-DMAG, ganetespib (STA-9090), radicicol, BIIB021, SNX-2112, SNX-5422, AT13387, IPI-504, IPI-493, KW-2478, DS-2248, XL888, CUDC-305 (Debio0932), PU-H71, NVP-AUY922, HSP990, or MPC-3100.

The compound may be, for example, a compound or a salt thereof represented by Formula (a), (b), (c), or (d).

The compound may be, for example, a substance capable of preventing the protein or a part thereof from binding to geldanamycin.

The complex may be such that the protein or a part thereof has chaperone functions, and the chaperone functions are inhibited by the compound.

EXAMPLES

Synthesis of Test Compound

In accordance with the method disclosed in WO 2011/004610, the following synthesis example compounds (Synthesis Examples 1 to 3) were synthesized.

Synthesis Example 1: 4-{3-isopropyl-4-(4-(1-methyl-1H-pyrazol-4-yl)-1H-imidazol-1-yl)-1H-pyrazolo[3,4-b]pyridin-1-yl}-3-methyl benzamide

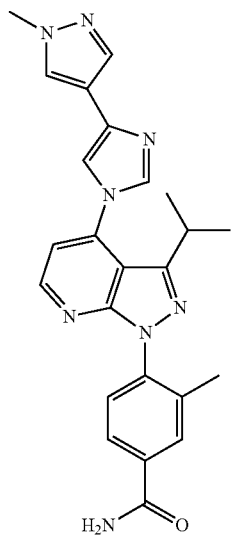 [SMILES: Cc1cc(C(N)=O)ccc1-n1nc(C(C)C)c2c(-n3cnc(-c4cnn(C)c4)c3)ccnc21]

Synthesis Example 2: 3-(ethylamino)-4-{4-(4-(1-methyl-1H-pyrazol-4-yl)-1H-imidazol-1-yl)-3-(trifluoromethyl)-1H-pyrazolo[3,4-b]pyridin-1-yl}benzamide

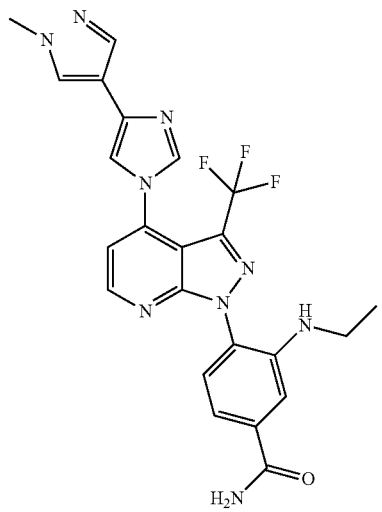 [SMILES: CCNc1cc(C(N)=O)ccc1-n1nc(C(F)(F)F)c2c(-n3cnc(/C(C=N)=C/NC)c3)ccnc21]

Synthesis Example 3: 3-ethyl-4-{3-isopropyl-4-(4-(1-methyl-1H-pyrazol-4-yl)-1H-imidazol-1-yl)-1H-pyrazolo[3,4-b]pyridin-1-yl}benzamide

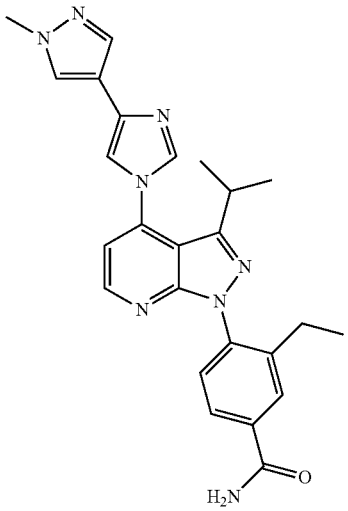 [SMILES: CCc1cc(C(N)=O)ccc1-n1nc(C(C)C)c2c(-n3cnc(-c4cnn(C)c4)c3)ccnc21]

Example 1: Preparation of Wild-Type and Mutant HSP90α Class A Proteins and Measurement of the Binding Activity The cDNA of human HSP90α class A gene (NCBI Reference Sequences registration number: NM_005348; code protein: NP_005339.3) corresponding to the 2nd to 236th amino acids of the human HSP90α class A protein was inserted into pET-19b (Novagen) to construct a plasmid pET-HSP90N (2-236) for expressing an HSP90 N-terminal protein containing an His-tag at its N terminal. Then, a plasmid capable of expressing a mutant HSP90 protein was produced by introducing mutation into the pET-HSP90N (2-236). Specifically, to mutate phenylalanine corresponding to the 138th amino acid of the HSP90α class A protein to leucine, the codon ttt at the corresponding site was mutated to ctg using mutagenic primers (5'-gttggtctgtattctgcttatttggt-tgc-3' SEQ ID NO:13, 5'-agaatacagaccaacaccgaactggcc-3' SEQ ID NO: 14) and a PrimeSTAR Mutagenesis Basal Kit (Takara). In this manner, a plasmid pET-HSP90N (2-236: F138L) was obtained. The amino acid sequence of mutant HSP90α class A N-terminal protein F138L expressed by this plasmid corresponds to the amino acid sequence of SEQ ID NO: 12 in which Xaa is leucine.

In a similar manner, a plasmid pET-HSP90N (2-236: Q23E) was prepared for causing a mutation of the glutamine corresponding to the 23rd amino acid of the HSP90α class A protein to glutamic acid, as well as a plasmid pET-HSP90N (2-236: Y139F) for causing a mutation of the tyrosine corresponding to the 139th amino acid of the HSP90α protein to phenylalanine.

Purified wild-type and mutant HSP90α class A solutions were prepared as follows. Each of the thus-prepared plasmids for expressing wild-type and mutant HSP90α N-terminal proteins was introduced into *Escherichia coli* cells (BL21 (DE3), Stratagene), followed by culturing at 37° C. for 4 hours in the presence of 0.5 mM isopropyl-beta-D-thiogalactopyranoside (Sigma-Aldrich). The collected *Escherichia coli* cells were suspended in a lysis buffer (50 mM Tris-HCl (pH 7.5), 200 mM NaCl), followed by ultrasonic disruption. The disrupted cell solution was subjected to centrifugal separation (40,000×g, 20 minutes), and the supernatant was obtained as a crude extract. This crude extract was fractionated using Ni Sepharose High Performance (GE Healthcare Japan Corporation) chromatography and HiLoad 26/60 Superdex 75 pg (GE Healthcare Japan Corporation), and the fractions in which HSP90α class A N-terminal proteins were concentrated was prepared into 50 mM Tris-HCl (pH 7.5)/20% glycerol solutions as purified HSP90 solutions. The thus-obtained wild-type HSP90α class A N-terminal protein and mutant HSP90α class A N-terminal proteins were respectively used for evaluation as wild-type HSP90 and mutant HSP90s. The purified HSP90 solutions were divided and stored at −80° C. until use.

The binding activity of the wild-type and mutant HSP90s was measured by a fluorescence polarization assay system. Each of the purified HSP90 solutions was diluted with a binding buffer (50 mM Tris-HCl (pH 7.5), 150 mM NaCl, 0.1% Triton-X100, 2 mM DTT, 0.1% BSA), and added to a 384-well plate (#3673, Corning Incorporated) containing test substances. Cy3B-labeled geldanamycin was added thereto to give a concentration of 40 nM, and reacted at room temperature for 2 hours, followed by measurement of fluorescence polarization value mP using a multilabel plate reader (EnVision, Perkin Elmer). Using the fluorescence signal of a test substance-free group (control) as a control, the inhibition rate (%) of Cy3B-labeled geldanamycin binding in terms of the test substance was calculated using the following equation. Each test substance was added to determine the concentration in which the Cy3B-labeled geldanamycin binding was inhibited by 50% of the control (IC50 (nM)), and use it as a relative index of HSP90 binding.

Inhibition rate (%)=$(C-T)/C \times 100$

T: Signal (mP value) in a well to which a test substance was added
C: Signal (mP value) in a well to which a test substance was not added
Table 2 shows the results.

The evaluation results revealed that the synthesis example compounds and known HSP90 inhibitors achieved almost the same IC50 values with respect to the wild-type HSP90, the mutant HSP90Q23E, and the mutant HSP90Y139F. However, with respect to the mutant HSP90F138L, the known HSP90 inhibitors, except for the synthesis example compounds, showed notably higher IC50 values than the IC50 values obtained with respect to the wild-type HSP90 and the other mutants, although the synthesis example compounds showed IC50 values almost the same as those achieved with respect to the wild-type HSP90 and the other mutants (Table 2). This indicates that the known HSP90 inhibitors showed less HSP90 binding activity when a particular site, i.e., F138, was mutated, reducing the inhibitory effect, whereas the synthesis example compounds showed the same HSP90 binding activity even when F138 was mutated, maintaining the inhibitory effect. This was more clearly confirmed by calculating the ratio of the IC50 value of each mutant with respect to the IC50 value of the wild-type (Table 2).

TABLE 2

| Test Substance | IC50 (nM) | | | | Ratio (vs WT) | | |
|---|---|---|---|---|---|---|---|
| | WT | Q23E | F138L | Y139F | Q23E | F138L | Y139F |
| NVP-AUY922 | 26 | 47 | 509 | 44 | 1.8 | 20 | 1.7 |
| 17-AAG | 123 | 209 | >3,000 | 262 | 1.7 | >20 | 2.1 |

TABLE 2-continued

| Test Substance | IC50 (nM) | | | | Ratio (vs WT) | | |
|---|---|---|---|---|---|---|---|
| | WT | Q23E | F138L | Y139F | Q23E | F138L | Y139F |
| BIIB021 | 49 | 58 | >1,000 | 89 | 1.2 | >20 | 1.8 |
| SNX-2112 | 76 | 97 | >1,000 | 57 | 1.3 | >10 | 0.75 |
| Synthesis Example 1 | 977 | 1,182 | 617 | 1,388 | 1.2 | 0.63 | 1.4 |
| Synthesis Example 2 | 600 | 859 | 1,335 | 211 | 1.4 | 2.2 | 0.35 |
| Synthesis Example 3 | 913 | 1,289 | 558 | 955 | 1.4 | 0.61 | 1.0 |

Example 2: Determination of Co-Crystal Structure of Human Wild-Type HSP90α Class A and Synthesis Example 1

The co-crystal structure of Synthesis Example 1 with wild-type HSP90 was obtained in accordance with the following procedures. The human wild-type HSP90α class A protein prepared as described above and Synthesis Example 1 were mixed at a molar ratio of 1:1, followed by purification on a Superdex 200 column pre-equilibrated with 50 mM Tris-HCl (pH 7.5), 200 mM NaCl, and 5 mM DTT. The peak fractions containing the complex were pooled, concentrated to 30 mg/mL, and used in a crystallization test. Crystals were grown at 4° C. using a sitting drop vapor diffusion method under the conditions of 50 mM Tris-HCl, pH 7.5, 0.2 M NaCl, and 15 to 22% of PEG6000. As a result, crystals were obtained after about seven weeks. The space group of the crystals was C2221. The crystals were flash-frozen in liquid nitrogen. The resolution dataset at 1.8 Å was collected using an apparatus (Rigaku R-AXIS IV++ MicroMax 7) within the lab.

Figure 2:
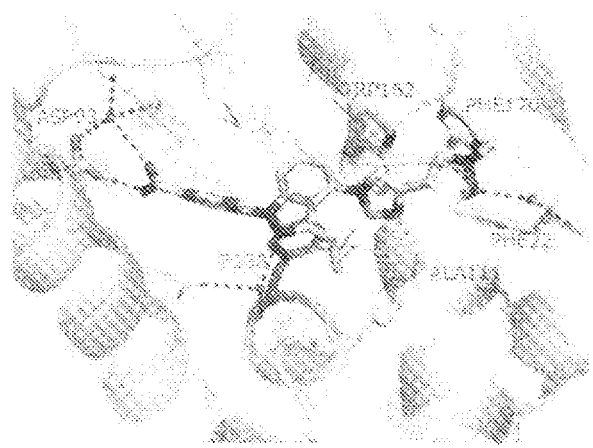
FIG. 2 is a diagram showing the binding mode of Synthesis Example 1 with respect to human wild-type HSP90α class A, clarified by X-ray co-crystal structural analysis (an enlarged view of a part of FIG. 1).
Figure 3:
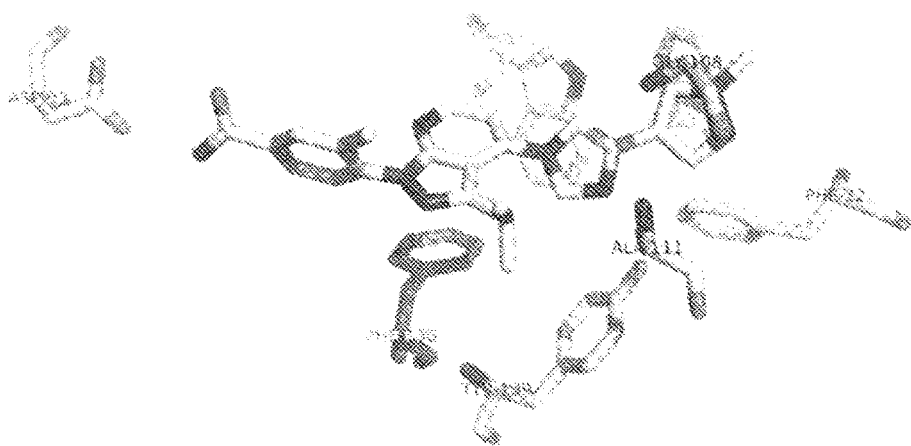
FIG. 3 is a diagram showing the binding mode of Synthesis Example 1 with respect to human wild-type HSP90α class A, clarified by X-ray co-crystal structural analysis (an enlarged view of a part of FIG. 1).
Figure 4:
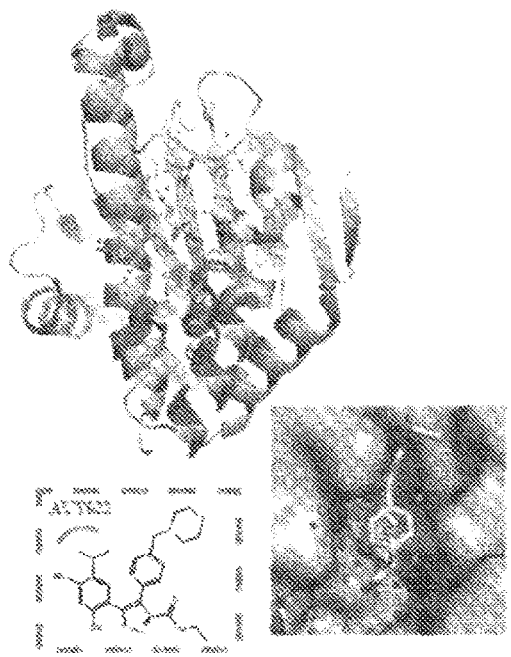
FIG. 4 is a diagram showing the binding mode of a known HSP90 inhibitor (NVP-AUY922), clarified by X-ray co-crystal structural analysis.
Figure 5:
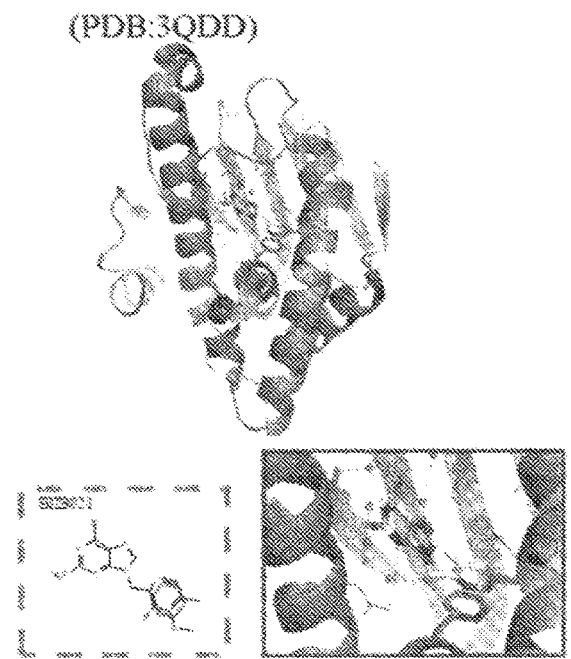
FIG. 5 is a diagram showing the binding mode of a known HSP90 inhibitor (BIIB021), clarified by X-ray co-crystal structural analysis.
Figure 6:
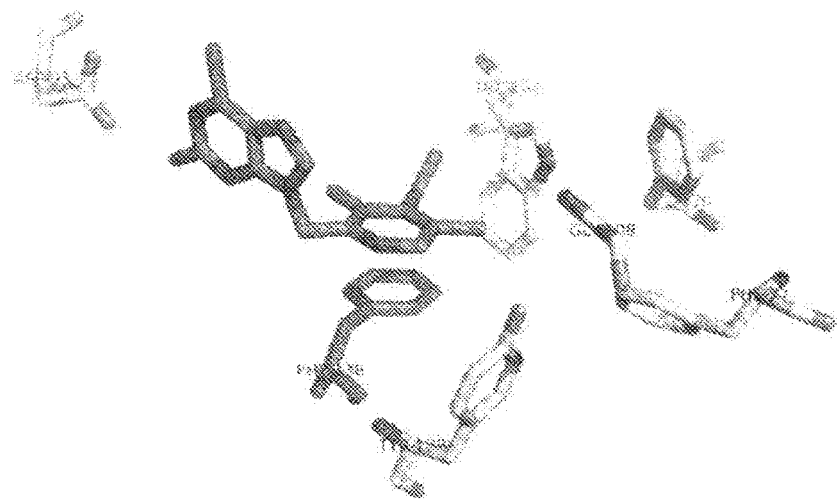
FIG. 6 is a diagram showing the binding mode of a known HSP90 inhibitor (BIIB021) with respect to human wild-type HSP90α class A, clarified by X-ray co-crystal structural analysis (an enlarged view of a part of FIG. 5).
Figure 7:
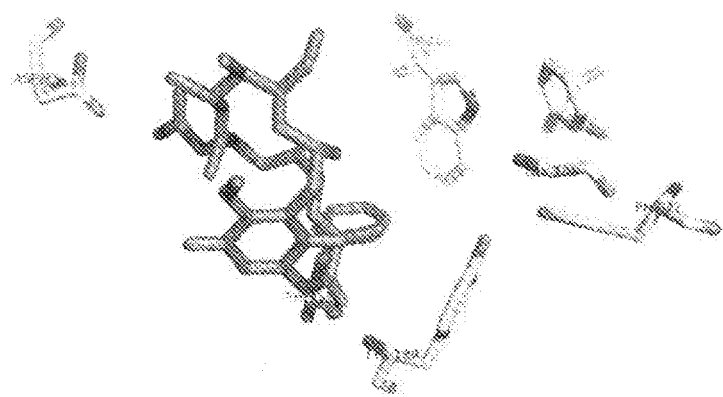
FIG. 7 is a diagram showing the binding mode of a known HSP90 inhibitor (geldanamycin) with respect to human wild-type HSP90α class A, clarified by X-ray co-crystal structural analysis.
Figure 8:
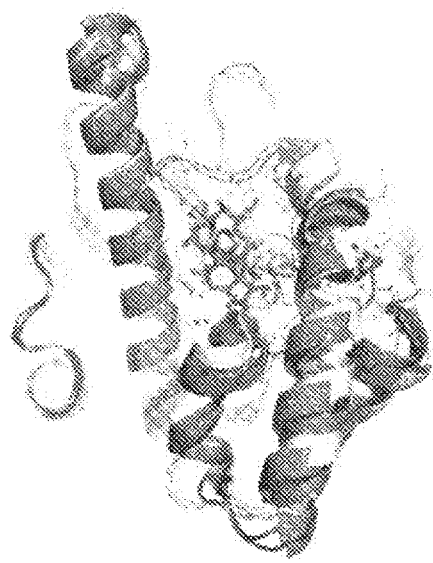
FIG. 8 is a diagram showing the merge of the binding modes of known HSP90 inhibitors (BIIB021 and geldanamycin) and Synthesis Example 1, clarified by X-ray co-crystal structural analysis.

FIGS. 1 to 3 show the binding mode of Synthesis Example 1 with respect to the human wild-type HSP90α class A, clarified by X-ray co-crystal structural analysis. FIGS. 2 and 3 are enlarged views of the binding sites shown in FIG. 1. In FIGS. 2 and 3, D93 (the 93th amino acid (aspartic acid) of the HSP90α class A) is an amino acid residue with which all of the known HSP90 inhibitors mentioned above for reference commonly form a hydrogen bond. FIG. 4 shows the binding mode of a known HSP90 inhibitor. The amino acid shown in red in FIGS. 1 to 8 is F138.

In addition to the space in the vicinity of D93 (ATP pocket), the known HSP90 inhibitors filled the space (2nd pocket) that appeared depending on the compound in an HSP90 conformation-dependent manner in the vicinity of F138. However, it is suggested that Synthesis Example 1 formed a hydrogen bond with D93. Additionally, Synthesis Example 1 filled the spaces formed with F22, A111, W162, F170, and G108 (3rd pocket), in addition to the space in the vicinity of F138. As is clear from FIGS. 1 to 8, the feature of Synthesis Example 1, which filled the 3rd pocket, was not found in the known HSP90 inhibitor group. This suggested that the synthesis example compounds of the Examples, which maintained the activity with respect to the mutant F138L, exhibited reduced dependency on F138 by filling the 3rd pocket. This is assumed to be the reason why the synthesis example compounds showed the inhibitory activity with respect to the F138 mutation, as well.

The invention claimed is:

1. A method for detecting the presence/absence of a mutation in the site corresponding to F138 of HSP90α class A in an HSP90 family protein in a biological sample obtained from a test subject, comprising
   a. obtaining a biological sample from said test subject; and
   b. detecting the presence/absence of a mutation in the site corresponding to F138 of HSP90α class A consisting of the amino acid sequence of SEQ ID NO: 1 in said biological sample.

2. The method according to claim 1, wherein the mutation in the site corresponding to F138 is:
   a mutation of the amino acid corresponding to F138 of HSP90α class A consisting of the amino acid sequence of SEQ ID NO: 1, in human HSP90α class A;
   a mutation of the amino acid corresponding to F133 of HSP90α class B consisting of the amino acid sequence of SEQ ID NO: 2, in human HSP90α class B; or
   a mutation of the amino acid corresponding to F199 of HSP90β consisting of the amino acid sequence of SEQ ID NO: 3, in human HSP90β.

3. The method according to claim 1, wherein the test subject is a tumor patient.

4. The method according to claim 1, wherein said biological sample is blood or tumor cells.

5. The method according to claim 1, wherein said test subject is a mammal.

6. The method according to claim 5, wherein said mammal is a human.

7. A method for treating a patient who is resistant to HSP90 inhibitors, comprising a. obtaining a biological sample from said patient;
b. detecting the presence of a mutation in a site corresponding to F138 of HSP90α class A in said biological sample, wherein said HSP90α class A comprises the amino acid sequence of SEQ ID NO: 1; and
c. administering an effective amount of an HSP90 inhibitor to said patient with a mutation in the site corresponding to F138 of HSP90α class A, wherein said HSP90 inhibitor fills a cavity in the vicinity of at least one amino acid selected from the group consisting of 5 amino acids in sites corresponding to F170, F22, G108, Y139, or W162 of HSP90α class A consisting of the amino acid sequence of SEQ ID NO: 1.

8. The method according to claim 7, wherein the HSP90 inhibitor is selected from the group consisting of geldanamycin, 17-AAG, 17-DMAG, ganetespib (STA-9090), radicicol, BIIB021, SNX-2112, SNX-5422, AT13387, IPI-504, IPI-493, KW-2478, DS-2248, XL888, CUDC-305 (Debio0932), PU-H71, NVP-AUY922, HSP990, and MPC-3100.

9. The method according to claim 7, wherein the mutation in the site corresponding to F138 is:
   a mutation of the amino acid corresponding to F138 of HSP90α class A consisting of the amino acid sequence of SEQ ID NO: 1, in human HSP90α class A;
   a mutation of the amino acid corresponding to F133 of HSP90α class B consisting of the amino acid sequence of SEQ ID NO: 2, in human HSP90α class B; or
   a mutation of the amino acid corresponding to F199 of HSP90β consisting of the amino acid sequence of SEQ ID NO: 3, in human HSP90β.

10. The method according to claim 7, wherein said patient is suffering from a condition selected from the group consisting of a neurodegenerative disorder, tumor, autoimmune disease, and viral infection.

11. A method for treating a patient who is not resistant to HSP90 inhibitors, comprising
   a. obtaining a biological sample from said patient;
   b. detecting the absence of a mutation in a site corresponding to F138 of HSP90α class A in said biological sample, wherein said HSP90α class A comprises the amino acid sequence of SEQ ID NO: 1, and
   c. administering an effective amount of an HSP90 inhibitor to said patient without a mutation in the site corresponding to F138 of HSP90α class A.

\* \* \* \* \*

SEQUENCE LISTING

```
<160> NUMBER OF SEQ ID NOS: 14

<210> SEQ ID NO 1
<211> LENGTH: 732
<212> TYPE: PRT
<213> ORGANISM: Homo sapiens

<400> SEQUENCE: 1

Met Pro Glu Glu Thr Gln Thr Gln Asp Gln Pro Met Glu Glu Glu
1               5                   10                  15

Val Glu Thr Phe Ala Phe Gln Ala Glu Ile Ala Gln Leu Met Ser Leu
            20                  25                  30

Ile Ile Asn Thr Phe Tyr Ser Asn Lys Glu Ile Phe Leu Arg Glu Leu
        35                  40                  45

Ile Ser Asn Ser Ser Asp Ala Leu Asp Lys Ile Arg Tyr Glu Ser Leu
    50                  55                  60

Thr Asp Pro Ser Lys Leu Asp Ser Gly Lys Glu Leu His Ile Asn Leu
65                  70                  75                  80

Ile Pro Asn Lys Gln Asp Arg Thr Leu Thr Ile Val Asp Thr Gly Ile
                85                  90                  95

Gly Met Thr Lys Ala Asp Leu Ile Asn Asn Leu Gly Thr Ile Ala Lys
            100                 105                 110

Ser Gly Thr Lys Ala Phe Met Glu Ala Leu Gln Ala Gly Ala Asp Ile
        115                 120                 125

Ser Met Ile Gly Gln Phe Gly Val Gly Phe Tyr Ser Ala Tyr Leu Val
    130                 135                 140

Ala Glu Lys Val Thr Val Ile Thr Lys His Asn Asp Asp Glu Gln Tyr
```

-continued

```
            145                 150                 155                 160
Ala Trp Glu Ser Ser Ala Gly Gly Ser Phe Thr Val Arg Thr Asp Thr
                    165                 170                 175
Gly Glu Pro Met Gly Arg Gly Thr Lys Val Ile Leu His Leu Lys Glu
                    180                 185                 190
Asp Gln Thr Glu Tyr Leu Glu Arg Arg Ile Lys Glu Ile Val Lys
                    195                 200                 205
Lys His Ser Gln Phe Ile Gly Tyr Pro Ile Thr Leu Phe Val Glu Lys
                    210                 215                 220
Glu Arg Asp Lys Glu Val Ser Asp Asp Glu Ala Glu Glu Lys Glu Asp
225                 230                 235                 240
Lys Glu Glu Glu Lys Glu Lys Glu Glu Lys Glu Ser Glu Asp Lys Pro
                    245                 250                 255
Glu Ile Glu Asp Val Gly Ser Asp Glu Glu Glu Lys Lys Asp Gly
                    260                 265                 270
Asp Lys Lys Lys Lys Lys Ile Lys Glu Lys Tyr Ile Asp Gln Glu
                    275                 280                 285
Glu Leu Asn Lys Thr Lys Pro Ile Trp Thr Arg Asn Pro Asp Asp Ile
                    290                 295                 300
Thr Asn Glu Glu Tyr Gly Glu Phe Tyr Lys Ser Leu Thr Asn Asp Trp
305                 310                 315                 320
Glu Asp His Leu Ala Val Lys His Phe Ser Val Glu Gly Gln Leu Glu
                    325                 330                 335
Phe Arg Ala Leu Leu Phe Val Pro Arg Arg Ala Pro Phe Asp Leu Phe
                    340                 345                 350
Glu Asn Arg Lys Lys Lys Asn Asn Ile Lys Leu Tyr Val Arg Arg Val
                    355                 360                 365
Phe Ile Met Asp Asn Cys Glu Glu Leu Ile Pro Glu Tyr Leu Asn Phe
                    370                 375                 380
Ile Arg Gly Val Val Asp Ser Glu Asp Leu Pro Leu Asn Ile Ser Arg
385                 390                 395                 400
Glu Met Leu Gln Gln Ser Lys Ile Leu Lys Val Ile Arg Lys Asn Leu
                    405                 410                 415
Val Lys Lys Cys Leu Glu Leu Phe Thr Glu Leu Ala Glu Asp Lys Glu
                    420                 425                 430
Asn Tyr Lys Lys Phe Tyr Glu Gln Phe Ser Lys Asn Ile Lys Leu Gly
                    435                 440                 445
Ile His Glu Asp Ser Gln Asn Arg Lys Lys Leu Ser Glu Leu Leu Arg
                    450                 455                 460
Tyr Tyr Thr Ser Ala Ser Gly Asp Glu Met Val Ser Leu Lys Asp Tyr
465                 470                 475                 480
Cys Thr Arg Met Lys Glu Asn Gln Lys His Ile Tyr Tyr Ile Thr Gly
                    485                 490                 495
Glu Thr Lys Asp Gln Val Ala Asn Ser Ala Phe Val Glu Arg Leu Arg
                    500                 505                 510
Lys His Gly Leu Glu Val Ile Tyr Met Ile Glu Pro Ile Asp Glu Tyr
                    515                 520                 525
Cys Val Gln Gln Leu Lys Glu Phe Glu Gly Lys Thr Leu Val Ser Val
                    530                 535                 540
Thr Lys Glu Gly Leu Glu Leu Pro Glu Asp Glu Glu Lys Lys Lys
545                 550                 555                 560
Gln Glu Glu Lys Lys Thr Lys Phe Glu Asn Leu Cys Lys Ile Met Lys
                    565                 570                 575
```

```
Asp Ile Leu Glu Lys Lys Val Glu Lys Val Val Ser Asn Arg Leu
        580                 585                 590

Val Thr Ser Pro Cys Cys Ile Val Thr Ser Thr Tyr Gly Trp Thr Ala
        595                 600                 605

Asn Met Glu Arg Ile Met Lys Ala Gln Ala Leu Arg Asp Asn Ser Thr
610                 615                 620

Met Gly Tyr Met Ala Ala Lys Lys His Leu Glu Ile Asn Pro Asp His
625                 630                 635                 640

Ser Ile Ile Glu Thr Leu Arg Gln Lys Ala Glu Ala Asp Lys Asn Asp
                645                 650                 655

Lys Ser Val Lys Asp Leu Val Ile Leu Leu Tyr Glu Thr Ala Leu Leu
                660                 665                 670

Ser Ser Gly Phe Ser Leu Glu Asp Pro Gln Thr His Ala Asn Arg Ile
                675                 680                 685

Tyr Arg Met Ile Lys Leu Gly Leu Gly Ile Asp Glu Asp Asp Pro Thr
                690                 695                 700

Ala Asp Asp Thr Ser Ala Ala Val Thr Glu Glu Met Pro Pro Leu Glu
705                 710                 715                 720

Gly Asp Asp Asp Thr Ser Arg Met Glu Glu Val Asp
                725                 730

<210> SEQ ID NO 2
<211> LENGTH: 724
<212> TYPE: PRT
<213> ORGANISM: Homo sapiens

<400> SEQUENCE: 2

Met Pro Glu Glu Val His His Gly Glu Glu Val Glu Thr Phe Ala
1               5                   10                  15

Phe Gln Ala Glu Ile Ala Gln Leu Met Ser Leu Ile Ile Asn Thr Phe
                20                  25                  30

Tyr Ser Asn Lys Glu Ile Phe Leu Arg Glu Leu Ile Ser Asn Ala Ser
                35                  40                  45

Asp Ala Leu Asp Lys Ile Arg Tyr Glu Ser Leu Thr Asp Pro Ser Lys
        50                  55                  60

Leu Asp Ser Gly Lys Glu Leu Lys Ile Asp Ile Ile Pro Asn Pro Gln
65                  70                  75                  80

Glu Arg Thr Leu Thr Leu Val Asp Thr Gly Ile Gly Met Thr Lys Ala
                85                  90                  95

Asp Leu Ile Asn Asn Leu Gly Thr Ile Ala Lys Ser Gly Thr Lys Ala
                100                 105                 110

Phe Met Glu Ala Leu Gln Ala Gly Ala Asp Ile Ser Met Ile Gly Gln
                115                 120                 125

Phe Gly Val Gly Phe Tyr Ser Ala Tyr Leu Val Ala Glu Lys Val Val
        130                 135                 140

Val Ile Thr Lys His Asn Asp Asp Glu Gln Tyr Ala Trp Glu Ser Ser
145                 150                 155                 160

Ala Gly Gly Ser Phe Thr Val Arg Ala Asp His Gly Glu Pro Ile Gly
                165                 170                 175

Arg Gly Thr Lys Val Ile Leu His Leu Lys Glu Asp Gln Thr Glu Tyr
                180                 185                 190

Leu Glu Glu Arg Arg Val Lys Glu Val Val Lys Lys His Ser Gln Phe
                195                 200                 205

Ile Gly Tyr Pro Ile Thr Leu Tyr Leu Glu Lys Glu Arg Glu Lys Glu
```

```
                  210               215                   220
Ile Ser Asp Asp Glu Ala Glu Glu Lys Gly Glu Lys Glu Glu
225                 230                   235                 240

Asp Lys Asp Asp Glu Glu Lys Pro Lys Ile Glu Asp Val Gly Ser Asp
                    245                   250                 255

Glu Glu Asp Asp Ser Gly Lys Asp Lys Lys Lys Thr Lys Lys Ile
                260               265                   270

Lys Glu Lys Tyr Ile Asp Gln Glu Leu Asn Lys Thr Lys Pro Ile
            275                   280                   285

Trp Thr Arg Asn Pro Asp Asp Ile Thr Gln Glu Glu Tyr Gly Glu Phe
        290                   295                   300

Tyr Lys Ser Leu Thr Asn Asp Trp Glu Asp His Leu Ala Val Lys His
305                 310                   315                 320

Phe Ser Val Glu Gly Gln Leu Glu Phe Arg Ala Leu Leu Phe Ile Pro
                    325                   330                 335

Arg Arg Ala Pro Phe Asp Leu Phe Glu Asn Lys Lys Lys Asn Asn
                340                   345                   350

Ile Lys Leu Tyr Val Arg Arg Val Phe Ile Met Asp Ser Cys Asp Glu
            355                   360                   365

Leu Ile Pro Glu Tyr Leu Asn Phe Ile Arg Gly Val Val Asp Ser Glu
370                   375                   380

Asp Leu Pro Leu Asn Ile Ser Arg Glu Met Leu Gln Gln Ser Lys Ile
385                   390                   395                 400

Leu Lys Val Ile Arg Lys Asn Ile Val Lys Lys Cys Leu Glu Leu Phe
                    405                   410                 415

Ser Glu Leu Ala Glu Asp Lys Glu Asn Tyr Lys Lys Phe Tyr Glu Ala
                420                   425                   430

Phe Ser Lys Asn Leu Lys Leu Gly Ile His Glu Asp Ser Thr Asn Arg
            435                   440                   445

Arg Arg Leu Ser Glu Leu Leu Arg Tyr His Thr Ser Gln Ser Gly Asp
450                   455                   460

Glu Met Thr Ser Leu Ser Glu Tyr Val Ser Arg Met Lys Glu Thr Gln
465                   470                   475                 480

Lys Ser Ile Tyr Tyr Ile Thr Gly Glu Ser Lys Glu Gln Val Ala Asn
                    485                   490                 495

Ser Ala Phe Val Glu Arg Val Arg Lys Arg Gly Phe Glu Val Val Tyr
                500                   505                   510

Met Thr Glu Pro Ile Asp Glu Tyr Cys Val Gln Gln Leu Lys Glu Phe
            515                   520                   525

Asp Gly Lys Ser Leu Val Ser Val Thr Lys Glu Gly Leu Glu Leu Pro
530                   535                   540

Glu Asp Glu Glu Glu Lys Lys Met Glu Ser Lys Ala Lys Phe
545                 550                   555                 560

Glu Asn Leu Cys Lys Leu Met Lys Glu Ile Leu Asp Lys Lys Val Glu
                565                   570                   575

Lys Val Thr Ile Ser Asn Arg Leu Val Ser Ser Pro Cys Cys Ile Val
                580                   585                   590

Thr Ser Thr Tyr Gly Trp Thr Ala Asn Met Glu Arg Ile Met Lys Ala
            595                   600                   605

Gln Ala Leu Arg Asp Asn Ser Thr Met Gly Tyr Met Met Ala Lys Lys
    610                   615                   620

His Leu Glu Ile Asn Pro Asp His Pro Ile Val Glu Thr Leu Arg Gln
625                   630                   635                 640
```

```
Lys Ala Glu Ala Asp Lys Asn Asp Lys Ala Val Lys Asp Leu Val Val
                645                 650                 655

Leu Leu Phe Glu Thr Ala Leu Leu Ser Ser Gly Phe Ser Leu Glu Asp
            660                 665                 670

Pro Gln Thr His Ser Asn Arg Ile Tyr Arg Met Ile Lys Leu Gly Leu
        675                 680                 685

Gly Ile Asp Glu Asp Glu Val Ala Ala Glu Pro Asn Ala Ala Val
    690                 695                 700

Pro Asp Glu Ile Pro Pro Leu Glu Gly Asp Glu Asp Ala Ser Arg Met
705                 710                 715                 720

Glu Glu Val Asp

<210> SEQ ID NO 3
<211> LENGTH: 803
<212> TYPE: PRT
<213> ORGANISM: Homo sapiens

<400> SEQUENCE: 3

Met Arg Ala Leu Trp Val Leu Gly Leu Cys Cys Val Leu Leu Thr Phe
1               5                   10                  15

Gly Ser Val Arg Ala Asp Asp Glu Val Asp Val Asp Gly Thr Val Glu
            20                  25                  30

Glu Asp Leu Gly Lys Ser Arg Glu Gly Ser Arg Thr Asp Asp Glu Val
        35                  40                  45

Val Gln Arg Glu Glu Glu Ala Ile Gln Leu Asp Gly Leu Asn Ala Ser
    50                  55                  60

Gln Ile Arg Glu Leu Arg Glu Lys Ser Glu Lys Phe Ala Phe Gln Ala
65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
            100                 105                 110

Asp Lys Ile Arg Leu Ile Ser Leu Thr Asp Glu Asn Ala Leu Ser Gly
        115                 120                 125

Asn Glu Glu Leu Thr Val Lys Ile Lys Cys Asp Lys Glu Lys Asn Leu
    130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190

Gly Gln Phe Gly Val Gly Phe Tyr Ser Ala Phe Leu Val Ala Asp Lys
        195                 200                 205

Val Ile Val Thr Ser Lys His Asn Asn Asp Thr Gln His Ile Trp Glu
    210                 215                 220

Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255

Asp Tyr Leu Glu Leu Asp Thr Ile Lys Asn Leu Val Lys Lys Tyr Ser
            260                 265                 270

Gln Phe Ile Asn Phe Pro Ile Tyr Val Trp Ser Ser Lys Thr Glu Thr
        275                 280                 285
```

```
Val Glu Glu Pro Met Glu Glu Glu Ala Ala Lys Glu Glu Lys Glu
    290             295                 300
Glu Ser Asp Asp Glu Ala Ala Val Glu Glu Glu Glu Glu Lys Lys
305             310                 315                 320
Pro Lys Thr Lys Lys Val Glu Lys Thr Val Trp Asp Trp Glu Leu Met
                325                 330                 335
Asn Asp Ile Lys Pro Ile Trp Gln Arg Pro Ser Lys Glu Val Glu Glu
                340                 345                 350
Asp Glu Tyr Lys Ala Phe Tyr Lys Ser Phe Ser Lys Glu Ser Asp Asp
            355                 360                 365
Pro Met Ala Tyr Ile His Phe Thr Ala Glu Gly Glu Val Thr Phe Lys
    370                 375                 380
Ser Ile Leu Phe Val Pro Thr Ser Ala Pro Arg Gly Leu Phe Asp Glu
385                 390                 395                 400
Tyr Gly Ser Lys Lys Ser Asp Tyr Ile Lys Leu Tyr Val Arg Arg Val
                405                 410                 415
Phe Ile Thr Asp Asp Phe His Asp Met Met Pro Lys Tyr Leu Asn Phe
                420                 425                 430
Val Lys Gly Val Val Asp Ser Asp Asp Leu Pro Leu Asn Val Ser Arg
        435                 440                 445
Glu Thr Leu Gln Gln His Lys Leu Leu Lys Val Ile Arg Lys Lys Leu
    450                 455                 460
Val Arg Lys Thr Leu Asp Met Ile Lys Lys Ile Ala Asp Asp Lys Tyr
465                 470                 475                 480
Asn Asp Thr Phe Trp Lys Glu Phe Gly Thr Asn Ile Lys Leu Gly Val
                485                 490                 495
Ile Glu Asp His Ser Asn Arg Thr Arg Leu Ala Lys Leu Leu Arg Phe
            500                 505                 510
Gln Ser Ser His His Pro Thr Asp Ile Thr Ser Leu Asp Gln Tyr Val
    515                 520                 525
Glu Arg Met Lys Glu Lys Gln Asp Lys Ile Tyr Phe Met Ala Gly Ser
    530                 535                 540
Ser Arg Lys Glu Ala Glu Ser Ser Pro Phe Val Glu Arg Leu Leu Lys
545                 550                 555                 560
Lys Gly Tyr Glu Val Ile Tyr Leu Thr Glu Pro Val Asp Glu Tyr Cys
                565                 570                 575
Ile Gln Ala Leu Pro Glu Phe Asp Gly Lys Arg Phe Gln Asn Val Ala
                580                 585                 590
Lys Glu Gly Val Lys Phe Asp Glu Ser Glu Lys Thr Lys Glu Ser Arg
            595                 600                 605
Glu Ala Val Glu Lys Glu Phe Glu Pro Leu Leu Asn Trp Met Lys Asp
    610                 615                 620
Lys Ala Leu Lys Asp Lys Ile Glu Lys Ala Val Val Ser Gln Arg Leu
625                 630                 635                 640
Thr Glu Ser Pro Cys Ala Leu Val Ala Ser Gln Tyr Gly Trp Ser Gly
                645                 650                 655
Asn Met Glu Arg Ile Met Lys Ala Gln Ala Tyr Gln Thr Gly Lys Asp
                660                 665                 670
Ile Ser Thr Asn Tyr Tyr Ala Ser Gln Lys Lys Thr Phe Glu Ile Asn
            675                 680                 685
Pro Arg His Pro Leu Ile Arg Asp Met Leu Arg Arg Ile Lys Glu Asp
    690                 695                 700
```

```
Glu Asp Asp Lys Thr Val Leu Asp Leu Ala Val Val Leu Phe Glu Thr
705                 710                 715                 720

Ala Thr Leu Arg Ser Gly Tyr Leu Leu Pro Asp Thr Lys Ala Tyr Gly
            725                 730                 735

Asp Arg Ile Glu Arg Met Leu Arg Leu Ser Leu Asn Ile Asp Pro Asp
            740                 745                 750

Ala Lys Val Glu Glu Pro Glu Glu Pro Glu Glu Thr Ala Glu
            755                 760                 765

Asp Thr Thr Glu Asp Thr Glu Gln Asp Glu Asp Glu Met Asp Val
    770                 775                 780

Gly Thr Asp Glu Glu Glu Thr Ala Lys Glu Ser Thr Ala Glu Lys
785                 790                 795                 800

Asp Glu Leu
```

<210> SEQ ID NO 4
<211> LENGTH: 235
<212> TYPE: PRT
<213> ORGANISM: Homo sapiens

<400> SEQUENCE: 4

```
Pro Glu Glu Thr Gln Thr Gln Asp Gln Pro Met Glu Glu Glu Val
1               5                   10                  15

Glu Thr Phe Ala Phe Gln Ala Glu Ile Ala Gln Leu Met Ser Leu Ile
            20                  25                  30

Ile Asn Thr Phe Tyr Ser Asn Lys Glu Ile Phe Leu Arg Glu Leu Ile
        35                  40                  45

Ser Asn Ser Ser Asp Ala Leu Asp Lys Ile Arg Tyr Glu Ser Leu Thr
50                  55                  60

Asp Pro Ser Lys Leu Asp Ser Gly Lys Glu Leu His Ile Asn Leu Ile
65                  70                  75                  80

Pro Asn Lys Gln Asp Arg Thr Leu Thr Ile Val Asp Thr Gly Ile Gly
            85                  90                  95

Met Thr Lys Ala Asp Leu Ile Asn Asn Leu Gly Thr Ile Ala Lys Ser
            100                 105                 110

Gly Thr Lys Ala Phe Met Glu Ala Leu Gln Ala Gly Ala Asp Ile Ser
            115                 120                 125

Met Ile Gly Gln Phe Gly Val Gly Phe Tyr Ser Ala Tyr Leu Val Ala
130                 135                 140

Glu Lys Val Thr Val Ile Thr Lys His Asn Asp Asp Glu Gln Tyr Ala
145                 150                 155                 160

Trp Glu Ser Ser Ala Gly Gly Ser Phe Thr Val Arg Thr Asp Thr Gly
            165                 170                 175

Glu Pro Met Gly Arg Gly Thr Lys Val Ile Leu His Leu Lys Glu Asp
            180                 185                 190

Gln Thr Glu Tyr Leu Glu Glu Arg Arg Ile Lys Glu Ile Val Lys Lys
        195                 200                 205

His Ser Gln Phe Ile Gly Tyr Pro Ile Thr Leu Phe Val Glu Lys Glu
    210                 215                 220

Arg Asp Lys Glu Val Ser Asp Asp Glu Ala Glu
225                 230                 235
```

<210> SEQ ID NO 5
<211> LENGTH: 2199
<212> TYPE: DNA
<213> ORGANISM: Homo sapiens

<400> SEQUENCE: 5

```
atgcctgagg aaacccagac ccaagaccaa ccgatggagg aggaggaggt tgagacgttc    60
gcctttcagg cagaaattgc ccagttgatg tcattgatca tcaatacttt ctactcgaac   120
aaagagatct ttctgagaga gctcatttca aattcatcag atgcattgga caaaatccgg   180
tatgaaagct tgacagatcc cagtaaatta gactctggga agagctgca tattaacctt    240
ataccgaaca acaagatcg aactctcact attgtggata ctggaattgg aatgaccaag    300
gctgacttga tcaataacct tggtactatc gccaagtctg ggaccaaagc gttcatggaa   360
gctttgcagg ctggtgcaga tatctctatg attggccagt tcggtgttgg ttttattct    420
gcttatttgg ttgctgagaa agtaactgtg atcaccaaac ataacgatga tgagcagtac   480
gcttgggagt cctcagcagg gggatcattc acagtgagga cagacacagg tgaacctatg   540
ggtcgtggaa caaaagttat cctacacctg aaagaagacc aaactgagta cttggaggaa   600
cgaagaataa aggagattgt gaagaaacat tctcagtta ttggatatcc cattactctt    660
tttgtggaga aggaacgtga taagaagta agcgatgatg aggctgaaga aaggaagac    720
aaagaagaag aaaagaaaa agaagagaaa gagtcggaag acaaacctga aattgaagat    780
gttggttctg atgaggaaga agaaaagaag gatggtgaca agaagaagaa gaagaagatt   840
aaggaaaagt acatcgatca agaagagctc aacaaaacaa agcccatctg gaccagaaat   900
cccgacgata ttactaatga ggagtacgga gaattctata agagcttgac caatgactgg   960
gaagatcact tggcagtgaa gcatttttca gttgaaggac agttggaatt cagagccctt  1020
ctatttgtcc cacgacgtgc tcctttgat ctgtttgaaa cagaaagaa aaagaacaac    1080
atcaaattgt atgtacgcag agttttcatc atggataact gtgaggagct aatccctgaa  1140
tatctgaact tcattagagg ggtggtagac tcggaggatc tccctctaaa catatcccgt  1200
gagatgttgc aacaaagcaa aattttgaaa gttatcagga gaatttggt caaaaaatgc   1260
ttagaactct ttactgaact ggcggaagat aagagaact caagaaatt ctatgagcag    1320
ttctctaaaa acataaagct tggaatacac gaagactctc aaaatcggaa gaagctttca   1380
gagctgttaa ggtactacac atctgcctct ggtgatgaga tggtttctct caaggactac  1440
tgcaccagaa tgaaggagaa ccagaaacat atctattata tcacaggtga gaccaaggac  1500
caggtagcta actcagcctt tgtggaacgt cttcggaaac atggcttaga agtgatctat  1560
atgattgagc ccattgatga gtactgtgtc caacagctga aggaatttga ggggaagact  1620
ttagtgtcag tcaccaaaga aggcctggaa cttccagagg atgaagaaga gaaaagaag   1680
caggaagaga aaaaaacaaa gtttgagaac ctctgcaaaa tcatgaaaga catattggag  1740
aaaaaagttg aaaggtggt tgtgtcaaac cgattggtga catctccatg ctgtattgtc   1800
acaagcacat atggctggac agcaaacatg gagagaatca tgaaagctca gccctaaga   1860
gacaactcaa caatgggtta catggcagca aagaaacacc tggagataaa ccctgaccat  1920
tccattattg agaccttaag gcaaaaggca gaggctgata gaacgacaa gtctgtgaag   1980
gatctggtca tcttgcttta tgaaactgcg ctcctgtctt ctggcttcag tctggaagat  2040
ccccagacac atgctaacag gatctacagg atgatcaaac ttggtctggg tattgatgaa  2100
gatgacccta ctgctgatga taccagtgct gctgtaactg aagaaatgcc acccttgaa   2160
ggagatgacg acacatcacg catggaagaa gtagactaa                          2199
```

<210> SEQ ID NO 6
<211> LENGTH: 2175

<212> TYPE: DNA
<213> ORGANISM: Homo sapiens

<400> SEQUENCE: 6

| | | | | | |
|---|---|---|---|---|---|
| atgcctgagg | aagtgcacca | tggagaggag | gaggtggaga | cttttgcctt | tcaggcagaa | 60 |
| attgcccaac | tcatgtccct | catcatcaat | accttctatt | ccaacaagga | gattttcctt | 120 |
| cgggagttga | tctctaatgc | ttctgatgcc | ttggacaaga | ttcgctatga | gagcctgaca | 180 |
| gacccttcga | agttggacag | tggtaaagag | ctgaaaattg | acatcatccc | caaccctcag | 240 |
| gaacgtaccc | tgactttggt | agacacaggc | attggcatga | ccaaagctga | tctcataaat | 300 |
| aatttgggaa | ccattgccaa | gtctggtact | aaagcattca | tggaggctct | tcaggctggt | 360 |
| gcagacatct | ccatgattgg | gcagtttggt | gttggctttt | attctgccta | cttggtggca | 420 |
| gagaaagtgg | ttgtgatcac | aaagcacaac | gatgatgaac | agtatgcttg | ggagtcttct | 480 |
| gctggaggtt | ccttcactgt | gcgtgctgac | catggtgagc | ccattggcag | gggtaccaaa | 540 |
| gtgatcctcc | atcttaaaga | agatcagaca | gagtacctag | aagagaggcg | ggtcaaagaa | 600 |
| gtagtgaaga | agcattctca | gttcataggc | tatcccatca | cccttcattt | ggagaaggaa | 660 |
| cgagagaagg | aaattagtga | tgatgaggca | gaggaagaga | aggtgagaa | agaagaggaa | 720 |
| gataaagatg | atgaagaaaa | acccaagatc | gaagatgtgg | gttcagatga | ggaggatgac | 780 |
| agcggtaagg | ataagaagaa | gaaaactaag | aagatcaaag | agaaatacat | tgatcaggaa | 840 |
| gaactaaaca | agaccaagcc | tatttggacc | agaaaccctg | atgacatcac | ccaagaggag | 900 |
| tatggagaat | tctacaagag | cctcactaat | gactgggaag | accacttggc | agtcaagcac | 960 |
| ttttctgtag | aaggtcagtt | ggaattcagg | gcattgctat | ttattcctcg | tcgggctccc | 1020 |
| tttgaccttt | ttgagaacaa | gaagaaaaag | aacaacatca | aactctatgt | ccgccgtgtg | 1080 |
| ttcatcatgg | acagctgtga | tgagttgata | ccagagtatc | tcaattttat | ccgtggtgtg | 1140 |
| gttgactctg | aggatctgcc | cctgaacatc | tcccgagaaa | tgctccagca | gagcaaaatc | 1200 |
| ttgaaagtca | ttcgcaaaaa | cattgttaag | aagtgccttg | agctcttctc | tgagctggca | 1260 |
| gaagacaagg | agaattacaa | gaaattctat | gaggcattct | ctaaaaatct | caagcttgga | 1320 |
| atccacgaag | actccactaa | ccgccgccgc | ctgtctgagc | tgctgcgcta | tcatacctcc | 1380 |
| cagtctggag | atgagatgac | atctctgtca | gagtatgttt | ctcgcatgaa | ggagacacag | 1440 |
| aagtccatct | attacatcac | tggtgagagc | aaagagcagg | tggccaactc | agcttttgtg | 1500 |
| gagcgagtgc | ggaaacgggg | cttcgaggtg | gtatatatga | ccgagcccat | tgacgagtac | 1560 |
| tgtgtgcagc | agctcaagga | atttgatggg | aagagcctgg | tctcagttac | caaggagggt | 1620 |
| ctggagctgc | ctgaggatga | ggaggagaag | aagaagatgg | aagagagcaa | ggcaaagttt | 1680 |
| gagaacctct | gcaagctcat | gaaagaaatc | ttagataaga | aggttgagaa | ggtgacaatc | 1740 |
| tccaatagac | ttgtgtcttc | accttgctgc | attgtgacca | gcacctacgg | ctggacagcc | 1800 |
| aatatggagc | ggatcatgaa | agcccaggca | cttcgggaca | actccaccat | gggctatatg | 1860 |
| atggccaaaa | agcacctgga | gatcaaccct | gaccacccca | ttgtggagac | gctgcggcag | 1920 |
| aaggctgagg | ccgacaagaa | tgataaggca | gttaaggacc | tggtggtgct | gctgtttgaa | 1980 |
| accgccctgc | tatcttctgg | cttttccctt | gaggatcccc | agacccactc | caaccgcatc | 2040 |
| tatcgcatga | tcaagctagg | tctaggtatt | gatgaagatg | aagtggcagc | agaggaaccc | 2100 |
| aatgctgcag | ttcctgatga | gatccccct | ctcgagggcg | atgaggatgc | gtctcgcatg | 2160 |
| gaagaagtcg | attag | | | | | 2175 |

<210> SEQ ID NO 7
<211> LENGTH: 2412
<212> TYPE: DNA
<213> ORGANISM: Homo sapiens

<400> SEQUENCE: 7

| | | | | | | |
|---|---|---|---|---|---|---|
| atgagggccc | tgtgggtgct | gggcctctgc | tgcgtcctgc | tgaccttcgg | gtcggtcaga | 60 |
| gctgacgatg | aagttgatgt | ggatggtaca | gtagaagagg | atctgggtaa | aagtagagaa | 120 |
| ggatcaagga | cggatgatga | agtagtacag | agagaggaag | aagctattca | gttggatgga | 180 |
| ttaaatgcat | cacaaataag | agaacttaga | gagaagtcgg | aaaagtttgc | cttccaagcc | 240 |
| gaagttaaca | gaatgatgaa | acttatcatc | aattcattgt | ataaaaataa | agagattttc | 300 |
| ctgagagaac | tgatttcaaa | tgcttctgat | gctttagata | agataaggct | aatatcactg | 360 |
| actgatgaaa | atgctctttc | tggaaatgag | gaactaacag | tcaaaattaa | gtgtgataag | 420 |
| gagaagaacc | tgctgcatgt | cacagacacc | ggtgtaggaa | tgaccagaga | agagttggtt | 480 |
| aaaaaccttg | gtaccatagc | caaatctggg | acaagcgagt | ttttaaacaa | aatgactgaa | 540 |
| gcacaggaag | atggccagtc | aacttctgaa | ttgattggcc | agtttggtgt | cggtttctat | 600 |
| tccgccttcc | ttgtagcaga | taaggttatt | gtcacttcaa | acacaacaa | cgatacccag | 660 |
| cacatctggg | agtctgactc | caatgaattt | tctgtaattg | ctgacccaag | aggaaacact | 720 |
| ctaggacggg | gaacgacaat | taccttgtc | ttaaaagaag | aagcatctga | ttaccttgaa | 780 |
| ttggatacaa | ttaaaaatct | cgtcaaaaaa | tattcacagt | tcataaactt | tcctatttat | 840 |
| gtatggagca | gcaagactga | aactgttgag | gagcccatgg | aggaagaaga | agcagccaaa | 900 |
| gaagagaaag | aagaatctga | tgatgaagct | gcagtagagg | aagaagaaga | agaaaagaaa | 960 |
| ccaaagacta | aaaagttga | aaaaactgtc | tgggactggg | aacttatgaa | tgatatcaaa | 1020 |
| ccaatatggc | agagaccatc | aaaagaagta | gaagaagatg | aatacaaagc | tttctacaaa | 1080 |
| tcattttcaa | aggaaagtga | tgaccccatg | gcttatattc | actttactgc | tgaaggggaa | 1140 |
| gttaccttca | aatcaatttt | atttgtaccc | acatctgctc | cacgtggtct | gtttgacgaa | 1200 |
| tatggatcta | aaaagagcga | ttacattaag | ctctatgtgc | gccgtgtatt | catcacagac | 1260 |
| gacttccatg | atatgatgcc | taaataccta | aattttgtca | gggtgtggt | ggactcagat | 1320 |
| gatctcccct | tgaatgtttc | ccgcgagact | cttcagcaac | ataaactgct | taaggtgatt | 1380 |
| aggaagaagc | ttgttcgtaa | aacgctggac | atgatcaaga | agattgctga | tgataaatac | 1440 |
| aatgatactt | tttggaaaga | atttggtacc | aacatcaagc | ttggtgtgat | tgaagaccac | 1500 |
| tcgaatcgaa | cacgtcttgc | taaacttctt | aggttccagt | cttctcatca | tccaactgac | 1560 |
| attactagcc | tagaccagta | tgtggaaaga | atgaaggaaa | aacaagacaa | aatctacttc | 1620 |
| atggctgggt | ccagcagaaa | agaggctgaa | tcttctccat | tgttgagcg | acttctgaaa | 1680 |
| aagggctatg | aagttattta | cctcacagaa | cctgtggatg | aatactgtat | tcaggccctt | 1740 |
| cccgaatttg | atgggaagag | gttccagaat | gttgccaaga | aggagtgaa | gttcgatgaa | 1800 |
| agtgagaaaa | ctaaggagag | tcgtgaagca | gttgagaaag | aatttgagcc | tctgctgaat | 1860 |
| tggatgaaaa | taaagccct | taaggacaag | attgaaaagg | ctgtggtgtc | tcagcgcctg | 1920 |
| acagaatctc | cgtgtgcttt | ggtggccagc | cagtacggat | ggtctggcaa | catggagaga | 1980 |
| atcatgaaag | cacaagcgta | ccaaacgggc | aaggacatct | ctacaaatta | ctatgcgagt | 2040 |
| cagaagaaaa | catttgaaat | taatcccaga | cacccgctga | tcagagacat | gcttcgacga | 2100 |
| attaaggaag | atgaagatga | taaaacagtt | ttggatcttg | ctgtggtttt | gtttgaaaca | 2160 |

-continued

```
gcaacgcttc ggtcagggta tcttttacca gacactaaag catatggaga tagaatagaa    2220
agaatgcttc gcctcagttt gaacattgac cctgatgcaa aggtggaaga agagcccgaa    2280
gaagaacctg aagagacagc agaagacaca acagaagaca cagagcaaga cgaagatgaa    2340
gaaatggatg tgggaacaga tgaagaagaa gaaacagcaa aggaatctac agctgaaaaa    2400
gatgaattgt aa                                                       2412
```

<210> SEQ ID NO 8
<211> LENGTH: 705
<212> TYPE: DNA
<213> ORGANISM: Homo sapiens

<400> SEQUENCE: 8

```
cctgaggaaa cccagaccca agaccaaccg atggaggagg aggaggttga gacgttcgcc     60
tttcaggcag aaattgccca gttgatgtca ttgatcatca atacttttcta ctcgaacaaa    120 gagatctttc tgagagagct catttcaaat tcatcagatg cattggacaa aatccggtat    180
gaaagcttga cagatcccag taaattagac tctgggaaag agctgcatat taaccttata    240
ccgaacaaac aagatcgaac tctcactatt gtggatactg gaattggaat gaccaaggct    300
gacttgatca ataaccttgg tactatcgcc aagtctggga ccaaagcgtt catggaagct    360
ttgcaggctg gtgcagatat ctctatgatt ggccagttcg gtgttggttt ttattctgct    420
tatttggttg ctgagaaagt aactgtgatc accaaacata cgatgatga gcagtacgct    480 tgggagtcct cagcaggggg atcattcaca gtgaggacag acacaggtga acctatgggt    540
cgtggaacaa aagttatcct acacctgaaa gaagaccaaa ctgagtactt ggaggaacga    600
agaataaagg agattgtgaa gaaacattct cagtttattg gatatcccat tactcttttt    660
gtggagaagg aacgtgataa agaagtaagc gatgatgagg ctgaa                    705
```

<210> SEQ ID NO 9
<211> LENGTH: 732
<212> TYPE: PRT
<213> ORGANISM: Homo sapiens
<220> FEATURE:
<221> NAME/KEY: misc_feature
<222> LOCATION: (138)..(138)
<223> OTHER INFORMATION: Xaa represents Ala, Arg, Asn, Asp, Cys, Gln,
      Glu, Gly, His, Ile, Leu, Val, Lys, Met, Pro, Ser, Thr, Trp or Tyr.

<400> SEQUENCE: 9

```
Met Pro Glu Glu Thr Gln Thr Gln Asp Gln Pro Met Glu Glu Glu Glu
1               5                   10                  15

Val Glu Thr Phe Ala Phe Gln Ala Glu Ile Ala Gln Leu Met Ser Leu
            20                  25                  30

Ile Ile Asn Thr Phe Tyr Ser Asn Lys Glu Ile Phe Leu Arg Glu Leu
        35                  40                  45

Ile Ser Asn Ser Ser Asp Ala Leu Asp Lys Ile Arg Tyr Glu Ser Leu
    50                  55                  60

Thr Asp Pro Ser Lys Leu Asp Ser Gly Lys Glu Leu His Ile Asn Leu
65                  70                  75                  80

Ile Pro Asn Lys Gln Asp Arg Thr Leu Thr Ile Val Asp Thr Gly Ile
                85                  90                  95

Gly Met Thr Lys Ala Asp Leu Ile Asn Asn Leu Gly Thr Ile Ala Lys
            100                 105                 110

Ser Gly Thr Lys Ala Phe Met Glu Ala Leu Gln Ala Gly Ala Asp Ile
        115                 120                 125
```

```
Ser Met Ile Gly Gln Phe Gly Val Gly Xaa Tyr Ser Ala Tyr Leu Val
    130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
                180                 185                 190

Asp Gln Thr Glu Tyr Leu Glu Glu Arg Arg Ile Lys Glu Ile Val Lys
                195                 200                 205

Lys His Ser Gln Phe Ile Gly Tyr Pro Ile Thr Leu Phe Val Glu Lys
210                 215                 220

Glu Arg Asp Lys Glu Val Ser Asp Asp Glu Ala Glu Glu Lys Glu Asp
225                 230                 235                 240

Lys Glu Glu Glu Lys Glu Lys Glu Glu Lys Glu Ser Glu Asp Lys Pro
                245                 250                 255

Glu Ile Glu Asp Val Gly Ser Asp Glu Glu Glu Lys Lys Asp Gly
                260                 265                 270

Asp Lys Lys Lys Lys Lys Ile Lys Glu Lys Tyr Ile Asp Gln Glu
    275                 280                 285

Glu Leu Asn Lys Thr Lys Pro Ile Trp Thr Arg Asn Pro Asp Asp Ile
    290                 295                 300

Thr Asn Glu Glu Tyr Gly Glu Phe Tyr Lys Ser Leu Thr Asn Asp Trp
305                 310                 315                 320

Glu Asp His Leu Ala Val Lys His Phe Ser Val Glu Gly Gln Leu Glu
                325                 330                 335

Phe Arg Ala Leu Leu Phe Val Pro Arg Arg Ala Pro Phe Asp Leu Phe
                340                 345                 350

Glu Asn Arg Lys Lys Lys Asn Asn Ile Lys Leu Tyr Val Arg Arg Val
                355                 360                 365

Phe Ile Met Asp Asn Cys Glu Glu Leu Ile Pro Glu Tyr Leu Asn Phe
370                 375                 380

Ile Arg Gly Val Val Asp Ser Glu Asp Leu Pro Leu Asn Ile Ser Arg
385                 390                 395                 400

Glu Met Leu Gln Gln Ser Lys Ile Leu Lys Val Ile Arg Lys Asn Leu
                405                 410                 415

Val Lys Lys Cys Leu Glu Leu Phe Thr Glu Leu Ala Glu Asp Lys Glu
                420                 425                 430

Asn Tyr Lys Lys Phe Tyr Glu Gln Phe Ser Lys Asn Ile Lys Leu Gly
                435                 440                 445

Ile His Glu Asp Ser Gln Asn Arg Lys Lys Leu Ser Glu Leu Leu Arg
450                 455                 460

Tyr Tyr Thr Ser Ala Ser Gly Asp Glu Met Val Ser Leu Lys Asp Tyr
465                 470                 475                 480

Cys Thr Arg Met Lys Glu Asn Gln Lys His Ile Tyr Tyr Ile Thr Gly
                485                 490                 495

Glu Thr Lys Asp Gln Val Ala Asn Ser Ala Phe Val Glu Arg Leu Arg
                500                 505                 510

Lys His Gly Leu Glu Val Ile Tyr Met Ile Glu Pro Ile Asp Glu Tyr
                515                 520                 525

Cys Val Gln Gln Leu Lys Glu Phe Glu Gly Lys Thr Leu Val Ser Val
530                 535                 540
```

```
Thr Lys Glu Gly Leu Glu Leu Pro Glu Asp Glu Glu Lys Lys Lys
545                 550                 555                 560

Gln Glu Glu Lys Lys Thr Lys Phe Glu Asn Leu Cys Lys Ile Met Lys
                565                 570                 575

Asp Ile Leu Glu Lys Lys Val Glu Lys Val Val Ser Asn Arg Leu
            580                 585                 590

Val Thr Ser Pro Cys Cys Ile Val Thr Ser Thr Tyr Gly Trp Thr Ala
            595                 600                 605

Asn Met Glu Arg Ile Met Lys Ala Gln Ala Leu Arg Asp Asn Ser Thr
    610                 615                 620

Met Gly Tyr Met Ala Ala Lys Lys His Leu Glu Ile Asn Pro Asp His
625                 630                 635                 640

Ser Ile Ile Glu Thr Leu Arg Gln Lys Ala Glu Ala Asp Lys Asn Asp
                645                 650                 655

Lys Ser Val Lys Asp Leu Val Ile Leu Leu Tyr Glu Thr Ala Leu Leu
            660                 665                 670

Ser Ser Gly Phe Ser Leu Glu Asp Pro Gln Thr His Ala Asn Arg Ile
    675                 680                 685

Tyr Arg Met Ile Lys Leu Gly Leu Gly Ile Asp Glu Asp Pro Thr
690                 695                 700

Ala Asp Asp Thr Ser Ala Ala Val Thr Glu Glu Met Pro Pro Leu Glu
705                 710                 715                 720

Gly Asp Asp Asp Thr Ser Arg Met Glu Glu Val Asp
            725                 730

<210> SEQ ID NO 10
<211> LENGTH: 724
<212> TYPE: PRT
<213> ORGANISM: Homo sapiens
<220> FEATURE:
<221> NAME/KEY: misc_feature
<222> LOCATION: (133)..(133)
<223> OTHER INFORMATION: Xaa represents Ala, Arg, Asn, Asp, Cys, Gln,
      Glu, Gly, His, Ile, Leu, Val, Lys, Met, Pro, Ser, Thr, Trp or Tyr.

<400> SEQUENCE: 10

Met Pro Glu Glu Val His His Gly Glu Glu Val Glu Thr Phe Ala
1               5                   10                  15

Phe Gln Ala Glu Ile Ala Gln Leu Met Ser Leu Ile Ile Asn Thr Phe
                20                  25                  30

Tyr Ser Asn Lys Glu Ile Phe Leu Arg Glu Leu Ile Ser Asn Ala Ser
            35                  40                  45

Asp Ala Leu Asp Lys Ile Arg Tyr Glu Ser Leu Thr Asp Pro Ser Lys
    50                  55                  60

Leu Asp Ser Gly Lys Glu Leu Lys Ile Asp Ile Ile Pro Asn Pro Gln
65                  70                  75                  80

Glu Arg Thr Leu Thr Leu Val Asp Thr Gly Ile Gly Met Thr Lys Ala
                85                  90                  95

Asp Leu Ile Asn Asn Leu Gly Thr Ile Ala Lys Ser Gly Thr Lys Ala
            100                 105                 110

Phe Met Glu Ala Leu Gln Ala Gly Ala Asp Ile Ser Met Ile Gly Gln
    115                 120                 125

Phe Gly Val Gly Xaa Tyr Ser Ala Tyr Leu Val Ala Glu Lys Val Val
130                 135                 140

Val Ile Thr Lys His Asn Asp Asp Glu Gln Tyr Ala Trp Glu Ser Ser
145                 150                 155                 160
```

-continued

```
Ala Gly Gly Ser Phe Thr Val Arg Ala Asp His Gly Glu Pro Ile Gly
            165                 170                 175

Arg Gly Thr Lys Val Ile Leu His Leu Lys Glu Asp Gln Thr Glu Tyr
            180                 185                 190

Leu Glu Glu Arg Arg Val Lys Glu Val Lys Lys His Ser Gln Phe
            195                 200                 205

Ile Gly Tyr Pro Ile Thr Leu Tyr Leu Glu Lys Glu Arg Glu Lys Glu
            210                 215                 220

Ile Ser Asp Asp Glu Ala Glu Glu Lys Gly Glu Lys Glu Glu
225                 230                 235                 240

Asp Lys Asp Asp Glu Glu Lys Pro Lys Ile Glu Asp Val Gly Ser Asp
            245                 250                 255

Glu Glu Asp Asp Ser Gly Lys Asp Lys Lys Lys Thr Lys Lys Ile
            260                 265                 270

Lys Glu Lys Tyr Ile Asp Gln Glu Glu Leu Asn Lys Thr Lys Pro Ile
            275                 280                 285

Trp Thr Arg Asn Pro Asp Ile Thr Gln Glu Glu Tyr Gly Glu Phe
            290                 295                 300

Tyr Lys Ser Leu Thr Asn Asp Trp Glu Asp His Leu Ala Val Lys His
305                 310                 315                 320

Phe Ser Val Glu Gly Gln Leu Glu Phe Arg Ala Leu Leu Phe Ile Pro
            325                 330                 335

Arg Arg Ala Pro Phe Asp Leu Phe Glu Asn Lys Lys Lys Asn Asn
            340                 345                 350

Ile Lys Leu Tyr Val Arg Arg Val Phe Ile Met Asp Ser Cys Asp Glu
            355                 360                 365

Leu Ile Pro Glu Tyr Leu Asn Phe Ile Arg Gly Val Val Asp Ser Glu
            370                 375                 380

Asp Leu Pro Leu Asn Ile Ser Arg Glu Met Leu Gln Gln Ser Lys Ile
385                 390                 395                 400

Leu Lys Val Ile Arg Lys Asn Ile Val Lys Lys Cys Leu Glu Leu Phe
            405                 410                 415

Ser Glu Leu Ala Glu Asp Lys Glu Asn Tyr Lys Lys Phe Tyr Glu Ala
            420                 425                 430

Phe Ser Lys Asn Leu Lys Leu Gly Ile His Glu Asp Ser Thr Asn Arg
            435                 440                 445

Arg Arg Leu Ser Glu Leu Leu Arg Tyr His Thr Ser Gln Ser Gly Asp
            450                 455                 460

Glu Met Thr Ser Leu Ser Glu Tyr Val Ser Arg Met Lys Glu Thr Gln
465                 470                 475                 480

Lys Ser Ile Tyr Tyr Ile Thr Gly Glu Ser Lys Glu Gln Val Ala Asn
            485                 490                 495

Ser Ala Phe Val Glu Arg Val Arg Lys Arg Gly Phe Glu Val Val Tyr
            500                 505                 510

Met Thr Glu Pro Ile Asp Glu Tyr Cys Val Gln Gln Leu Lys Glu Phe
            515                 520                 525

Asp Gly Lys Ser Leu Val Ser Val Thr Lys Glu Gly Leu Glu Leu Pro
            530                 535                 540

Glu Asp Glu Glu Glu Lys Lys Met Glu Glu Ser Lys Ala Lys Phe
545                 550                 555                 560

Glu Asn Leu Cys Lys Leu Met Lys Glu Ile Leu Asp Lys Lys Val Glu
            565                 570                 575

Lys Val Thr Ile Ser Asn Arg Leu Val Ser Ser Pro Cys Cys Ile Val
```

```
                580              585              590
Thr Ser Thr Tyr Gly Trp Thr Ala Asn Met Glu Arg Ile Met Lys Ala
            595              600              605

Gln Ala Leu Arg Asp Asn Ser Thr Met Gly Tyr Met Met Ala Lys Lys
            610              615              620

His Leu Glu Ile Asn Pro Asp His Pro Ile Val Glu Thr Leu Arg Gln
625              630              635              640

Lys Ala Glu Ala Asp Lys Asn Asp Lys Ala Val Lys Asp Leu Val Val
            645              650              655

Leu Leu Phe Glu Thr Ala Leu Leu Ser Ser Gly Phe Ser Leu Glu Asp
            660              665              670

Pro Gln Thr His Ser Asn Arg Ile Tyr Arg Met Ile Lys Leu Gly Leu
            675              680              685

Gly Ile Asp Glu Asp Glu Val Ala Ala Glu Pro Asn Ala Ala Val
            690              695              700

Pro Asp Glu Ile Pro Pro Leu Glu Gly Asp Glu Asp Ala Ser Arg Met
705              710              715              720

Glu Glu Val Asp

<210> SEQ ID NO 11
<211> LENGTH: 803
<212> TYPE: PRT
<213> ORGANISM: Homo sapiens
<220> FEATURE:
<221> NAME/KEY: misc_feature
<222> LOCATION: (199)..(199)
<223> OTHER INFORMATION: Xaa represents Ala, Arg, Asn, Asp, Cys, Gln,
      Glu, Gly, His, Ile, Leu, Val, Lys, Met, Pro, Ser, Thr, Trp or Tyr.

<400> SEQUENCE: 11

Met Arg Ala Leu Trp Val Leu Gly Leu Cys Cys Val Leu Leu Thr Phe
1               5                  10                  15

Gly Ser Val Arg Ala Asp Asp Glu Val Asp Val Asp Gly Thr Val Glu
            20                  25                  30

Glu Asp Leu Gly Lys Ser Arg Glu Gly Ser Arg Thr Asp Asp Glu Val
        35                  40                  45

Val Gln Arg Glu Glu Glu Ala Ile Gln Leu Asp Gly Leu Asn Ala Ser
    50                  55                  60

Gln Ile Arg Glu Leu Arg Glu Lys Ser Glu Lys Phe Ala Phe Gln Ala
65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
            100                 105                 110

Asp Lys Ile Arg Leu Ile Ser Leu Thr Asp Glu Asn Ala Leu Ser Gly
        115                 120                 125

Asn Glu Glu Leu Thr Val Lys Ile Lys Cys Asp Lys Glu Lys Asn Leu
    130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190

Gly Gln Phe Gly Val Gly Xaa Tyr Ser Ala Phe Leu Val Ala Asp Lys
        195                 200                 205
```

-continued

```
Val Ile Val Thr Ser Lys His Asn Asn Asp Thr Gln His Ile Trp Glu
    210                 215                 220

Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255

Asp Tyr Leu Glu Leu Asp Thr Ile Lys Asn Leu Val Lys Lys Tyr Ser
                260                 265                 270

Gln Phe Ile Asn Phe Pro Ile Tyr Val Trp Ser Ser Lys Thr Glu Thr
            275                 280                 285

Val Glu Glu Pro Met Glu Glu Glu Ala Ala Lys Glu Glu Lys Glu
        290                 295                 300

Glu Ser Asp Asp Glu Ala Ala Val Glu Glu Glu Glu Glu Lys Lys
305                 310                 315                 320

Pro Lys Thr Lys Lys Val Glu Lys Thr Val Trp Asp Trp Glu Leu Met
                325                 330                 335

Asn Asp Ile Lys Pro Ile Trp Gln Arg Pro Ser Lys Glu Val Glu Glu
                340                 345                 350

Asp Glu Tyr Lys Ala Phe Tyr Lys Ser Phe Ser Lys Glu Ser Asp Asp
                355                 360                 365

Pro Met Ala Tyr Ile His Phe Thr Ala Glu Gly Glu Val Thr Phe Lys
        370                 375                 380

Ser Ile Leu Phe Val Pro Thr Ser Ala Pro Arg Gly Leu Phe Asp Glu
385                 390                 395                 400

Tyr Gly Ser Lys Lys Ser Asp Tyr Ile Lys Leu Tyr Val Arg Arg Val
                405                 410                 415

Phe Ile Thr Asp Asp Phe His Asp Met Met Pro Lys Tyr Leu Asn Phe
                420                 425                 430

Val Lys Gly Val Val Asp Ser Asp Asp Leu Pro Leu Asn Val Ser Arg
            435                 440                 445

Glu Thr Leu Gln Gln His Lys Leu Leu Lys Val Ile Arg Lys Lys Leu
        450                 455                 460

Val Arg Lys Thr Leu Asp Met Ile Lys Lys Ile Ala Asp Asp Lys Tyr
465                 470                 475                 480

Asn Asp Thr Phe Trp Lys Glu Phe Gly Thr Asn Ile Lys Leu Gly Val
                485                 490                 495

Ile Glu Asp His Ser Asn Arg Thr Arg Leu Ala Lys Leu Leu Arg Phe
            500                 505                 510

Gln Ser Ser His His Pro Thr Asp Ile Thr Ser Leu Asp Gln Tyr Val
        515                 520                 525

Glu Arg Met Lys Glu Lys Gln Asp Lys Ile Tyr Phe Met Ala Gly Ser
        530                 535                 540

Ser Arg Lys Glu Ala Glu Ser Ser Pro Phe Val Glu Arg Leu Leu Lys
545                 550                 555                 560

Lys Gly Tyr Glu Val Ile Tyr Leu Thr Glu Pro Val Asp Glu Tyr Cys
                565                 570                 575

Ile Gln Ala Leu Pro Glu Phe Asp Gly Lys Arg Phe Gln Asn Val Ala
            580                 585                 590

Lys Glu Gly Val Lys Phe Asp Glu Ser Glu Lys Thr Lys Glu Ser Arg
            595                 600                 605

Glu Ala Val Glu Lys Glu Phe Glu Pro Leu Leu Asn Trp Met Lys Asp
610                 615                 620
```

```
Lys Ala Leu Lys Asp Lys Ile Glu Lys Ala Val Val Ser Gln Arg Leu
625                 630                 635                 640

Thr Glu Ser Pro Cys Ala Leu Val Ala Ser Gln Tyr Gly Trp Ser Gly
            645                 650                 655

Asn Met Glu Arg Ile Met Lys Ala Gln Ala Tyr Gln Thr Gly Lys Asp
            660                 665                 670

Ile Ser Thr Asn Tyr Tyr Ala Ser Gln Lys Lys Thr Phe Glu Ile Asn
        675                 680                 685

Pro Arg His Pro Leu Ile Arg Asp Met Leu Arg Arg Ile Lys Glu Asp
690                 695                 700

Glu Asp Lys Thr Val Leu Asp Leu Ala Val Val Leu Phe Glu Thr
705                 710                 715                 720

Ala Thr Leu Arg Ser Gly Tyr Leu Leu Pro Asp Thr Lys Ala Tyr Gly
            725                 730                 735

Asp Arg Ile Glu Arg Met Leu Arg Leu Ser Leu Asn Ile Asp Pro Asp
            740                 745                 750

Ala Lys Val Glu Glu Pro Glu Glu Pro Glu Glu Thr Ala Glu
        755                 760                 765

Asp Thr Thr Glu Asp Thr Glu Gln Asp Glu Asp Glu Glu Met Asp Val
770                 775                 780

Gly Thr Asp Glu Glu Glu Glu Thr Ala Lys Glu Ser Thr Ala Glu Lys
785                 790                 795                 800

Asp Glu Leu

<210> SEQ ID NO 12
<211> LENGTH: 235
<212> TYPE: PRT
<213> ORGANISM: Homo sapiens
<220> FEATURE:
<221> NAME/KEY: misc_feature
<222> LOCATION: (137)..(137)
<223> OTHER INFORMATION: Xaa represents Ala, Arg, Asn, Asp, Cys, Gln,
      Glu, Gly, His, Ile, Leu, Val, Lys, Met, Pro, Ser, Thr, Trp or Tyr.

<400> SEQUENCE: 12

Pro Glu Glu Thr Gln Thr Gln Asp Gln Pro Met Glu Glu Glu Glu Val
1               5                   10                  15

Glu Thr Phe Ala Phe Gln Ala Glu Ile Ala Gln Leu Met Ser Leu Ile
            20                  25                  30

Ile Asn Thr Phe Tyr Ser Asn Lys Glu Ile Phe Leu Arg Glu Leu Ile
        35                  40                  45

Ser Asn Ser Ser Asp Ala Leu Asp Lys Ile Arg Tyr Glu Ser Leu Thr
50                  55                  60

Asp Pro Ser Lys Leu Asp Ser Gly Lys Glu Leu His Ile Asn Leu Ile
65                  70                  75                  80

Pro Asn Lys Gln Asp Arg Thr Leu Thr Ile Val Asp Thr Gly Ile Gly
            85                  90                  95

Met Thr Lys Ala Asp Leu Ile Asn Asn Leu Gly Thr Ile Ala Lys Ser
            100                 105                 110

Gly Thr Lys Ala Phe Met Glu Ala Leu Gln Ala Gly Ala Asp Ile Ser
            115                 120                 125

Met Ile Gly Gln Phe Gly Val Gly Xaa Tyr Ser Ala Tyr Leu Val Ala
        130                 135                 140

Glu Lys Val Thr Val Ile Thr Lys His Asn Asp Asp Glu Gln Tyr Ala
145                 150                 155                 160

Trp Glu Ser Ser Ala Gly Gly Ser Phe Thr Val Arg Thr Asp Thr Gly
```

-continued

```
                   165                 170                 175
Glu Pro Met Gly Arg Gly Thr Lys Val Ile Leu His Leu Lys Glu Asp
            180                 185                 190

Gln Thr Glu Tyr Leu Glu Glu Arg Arg Ile Lys Glu Ile Val Lys Lys
        195                 200                 205

His Ser Gln Phe Ile Gly Tyr Pro Ile Thr Leu Phe Val Glu Lys Glu
    210                 215                 220

Arg Asp Lys Glu Val Ser Asp Glu Ala Glu
225                 230                 235

<210> SEQ ID NO 13
<211> LENGTH: 29
<212> TYPE: DNA
<213> ORGANISM: Artificial
<220> FEATURE:
<223> OTHER INFORMATION: Primer

<400> SEQUENCE: 13
gttggtctgt attctgctta tttggttgc                                29

<210> SEQ ID NO 14
<211> LENGTH: 27
<212> TYPE: DNA
<213> ORGANISM: Artificial
<220> FEATURE:
<223> OTHER INFORMATION: Primer

<400> SEQUENCE: 14
agaatacaga ccaacaccga actggcc                                  27
```